(12) United States Patent
Trieu et al.

(10) Patent No.: US 9,964,551 B2
(45) Date of Patent: May 8, 2018

(54) ANTIBODY-BASED AFFINITY REAGENTS FOR BINDING PACLITAXEL

(71) Applicant: Autotelic LLC, City of Industry, CA (US)

(72) Inventors: Vuong Trieu, Agoura Hills, CA (US); Chulho Park, San Diego, CA (US)

(73) Assignee: AUTOTELIC, LLC, City of Industry, CA (US)

( * ) Notice: Subject to any disclaimer, the term of this patent is extended or adjusted under 35 U.S.C. 154(b) by 0 days. days.

(21) Appl. No.: 15/289,016

(22) Filed: Oct. 7, 2016

(65) Prior Publication Data

US 2017/0102401 A1    Apr. 13, 2017

Related U.S. Application Data

(60) Provisional application No. 62/238,667, filed on Oct. 7, 2015.

(51) Int. Cl.
*G01N 33/94* (2006.01)
*C07K 16/44* (2006.01)

(52) U.S. Cl.
CPC .............. *G01N 33/94* (2013.01); *C07K 16/44* (2013.01); *C07K 2317/565* (2013.01)

(58) Field of Classification Search
CPC .......................... G01N 33/94; C07K 2317/565
USPC ........................................... 424/133.1, 137.1
See application file for complete search history.

(56) References Cited

U.S. PATENT DOCUMENTS

| | | | |
|---|---|---|---|
| 5,670,663 A * | 9/1997 | Durzan ................. | A61K 36/13 549/332 |
| 5,955,621 A | 9/1999 | Durzan et al. | |
| 6,528,301 B1 | 3/2003 | Breme et al. | |
| 2010/0166746 A1 | 7/2010 | Chowdhury et al. | |
| 2012/0034711 A1 | 2/2012 | Li et al. | |
| 2014/0017812 A1 | 1/2014 | Smith et al. | |
| 2015/0285827 A1* | 10/2015 | Lee ........................ | G01N 33/94 436/501 |

FOREIGN PATENT DOCUMENTS

| | | |
|---|---|---|
| WO | 2012/166795 A1 | 12/2012 |
| WO | 2015/154091 A1 | 10/2015 |
| WO | WO 2015154091 A1 * | 10/2015 |

OTHER PUBLICATIONS

Kingston et al. J. Nat. Prod. 53:1-12 (1990)).*
Grothaus et al. (J. Nat. Prod. 58(7):1003-1014 (1995)).*
Bignami, G.S., and S.L. Mooberry, "Monoclonal Antibodies to Taxanes That Neutralize the Biological Activity of Paclitaxel," Cancer Letters 126(2):127-133, Apr. 1998.
Chao, Z., et al., "Development of an Indirect Competitive Enzyme-Linked Immunosorbent Assay (icELISA) Using Highly Specific Monoclonal Antibody Against Paclitaxel," Journal of Natural Medicines 67(3):512-518, Jul. 2013.
Invitation to Pay Additional Fees and Where Applicable, Protest Fee, mailed Jan. 11, 2017, issued in International Application No. PCT/US2016/056085, filed Oct. 7, 2016, 2 pages.
International Search Report and Written Opinion dated Mar. 20, 2017, issued in corresponding International Application No. PCT/US16/56085, filed Oct. 7, 2016, 12 pages.
Lee, C., et al., "Point of Care PK Quantitation Device for Pharmacokinetic Guided Dosing of Paclitaxel as a Companion Diagnostic Device," Poster B-389 from TDM/Toxicology/DAU Poster Session of Jul. 30, 2014, Clinical Chemistry 60(10, Suppl.):S245, Oct. 2014.

* cited by examiner

*Primary Examiner* — Lynn A Bristol
(74) *Attorney, Agent, or Firm* — Christensen O'Connor Johnson Kindness PLLC

(57) ABSTRACT

Optimized affinity reagent compositions for binding paclitaxel, such as antibodies, antibody fragments, and antibody derivatives, related methods of use, and related kits, are provided herein. Affinity reagents that comprise one or more complementary determining regions (CDRs) optimized from anti-paclitaxel antibodies antibody 8A10 and 3C6 are specifically provided. The disclosed affinity reagents are useful for binding and detecting paclitaxel in a sample, such as for determining or optimizing future doses of paclitaxel in a subject that was previously administered with paclitaxel.

13 Claims, 18 Drawing Sheets

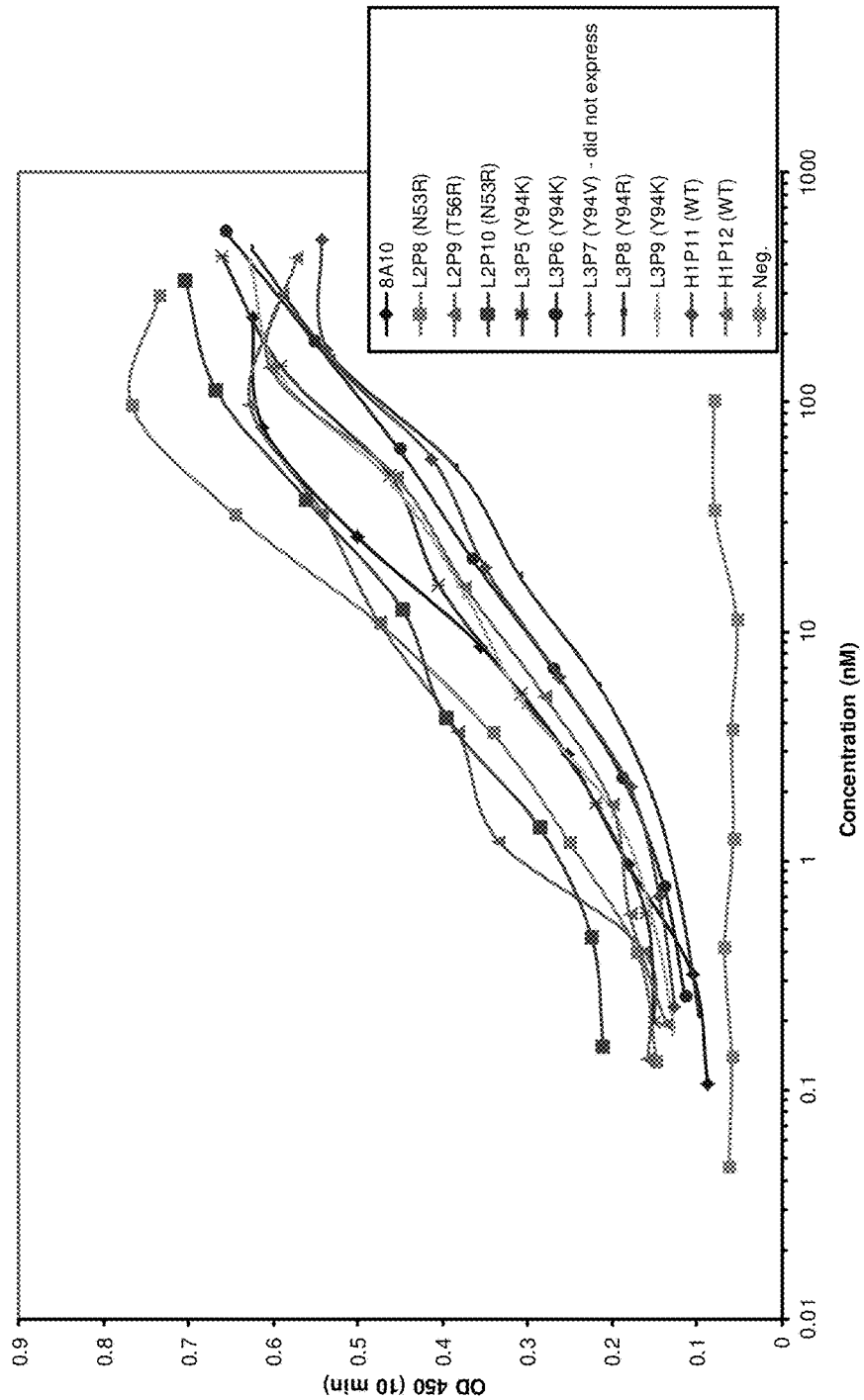

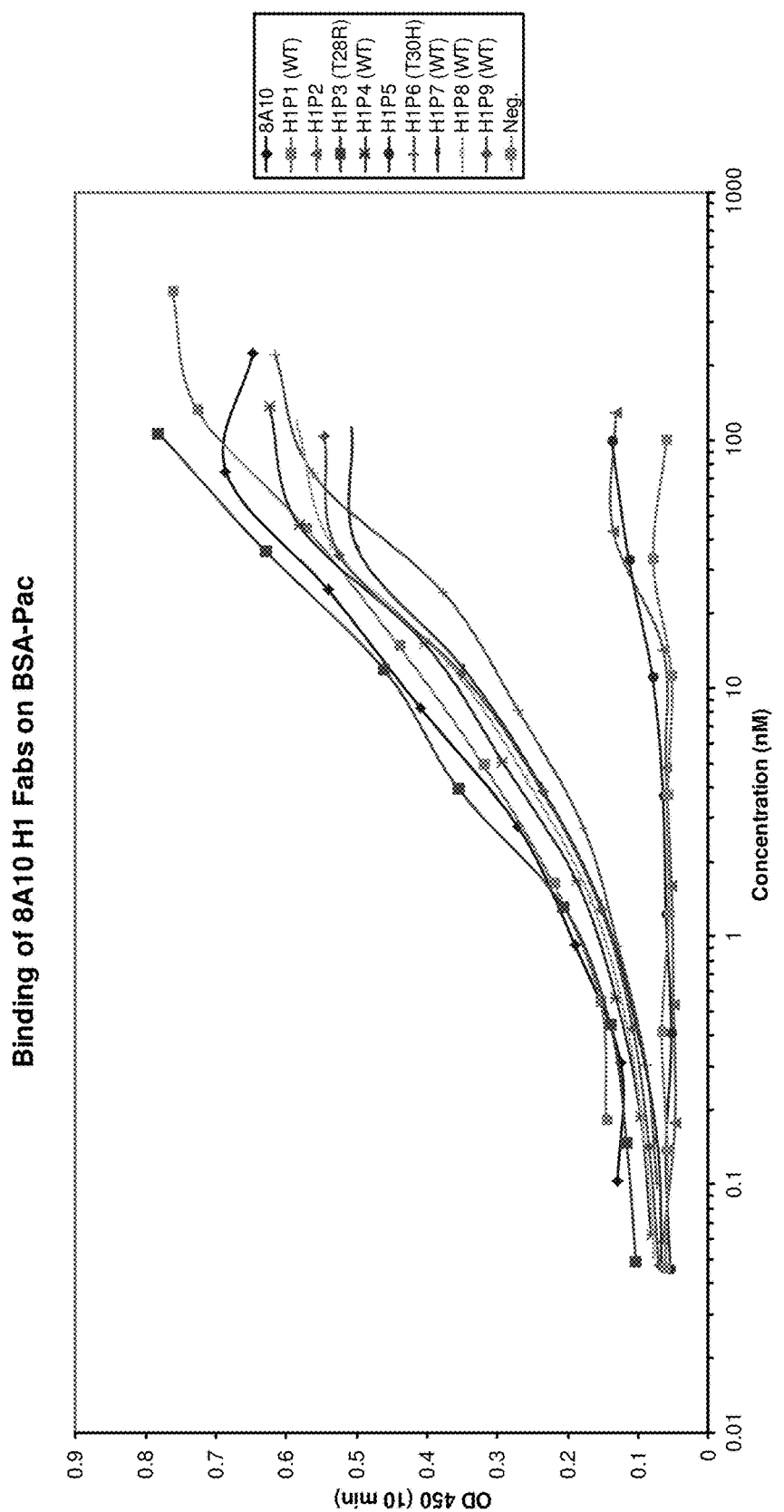

Amino acid sequence alignment of variable regions obtained from the 8A10 Combinatorial Library

VL ALIGNMENT

| | | |
|---|---|---|
| 8A10_VL | (8) | DIVMTQSQKFMSTTLGERVSITCKPSQ̲VGS̲VTWWQQKPGQSPKLLIYSAS̲NRYTGVPDRFTGSGSGTDFTLTISNVQSEDLADYFCQQYSSYPYTFGGGTKLEIK |
| 8A10_CP2_VL_ | (190) | DIVMTQSQKFMSTTLGERVSITCKPSQ̲VGS̲VTWWQQKPGQSPKLLIYSAS̲NRYTGVPDRFTGSGSGTDFTLTISNVQSEDLADYFCQQYSSYPYTFGGGTKLEIK |
| 8A10_CP3_VL_ | (191) | DIVMTQSQKFMSTTLGERVSITCKPSQ̲VGS̲VTWWQQKPGQSPKLLIYSAS̲NRYTGVPDRFTGSGSGTDFTLTISNVQSEDLADYFCQQYSSYPYTFGGGTKLEIK |
| 8A10_CP4_VL_ | (192) | DIVMTQSQKFMSTTLGERVSITCKPSQ̲VGS̲VTWWQQKPGQSPKLLIYSAS̲NRYTGVPDRFTGSGSGTDFTLTISNVQSEDLADYFCQQYSSYPYTFGGGTKLEIK |
| 8A10_CP5_VL_ | (193) | DIVMTQSQKFMSTTLGERVSITCKPSQ̲VGS̲VTWWQQKPGQSPKLLIYSAS̲NRYTGVPDRFTGSGSGTDFTLTISNVQSEDLADYFCQQYSSYPYTFGGGTKLEIK |
| 8A10_CP6_VL_ | (194) | DIVMTQSQKFMSTTLGERVSITCKPSQ̲VGS̲VTWWQQKPGQSPKLLIYSAS̲NRYTGVPDRFTGSGSGTDFTLTISNVQSEDLADYFCQQYSSYPYTFGGGTKLEIK |
| 8A10_CP7_VL_ | (195) | DIVMTQSQKFMSTTLGERVSITCKPSQ̲VGS̲VTWWQQKPGQSPKLLIYSAS̲NRYTGVPDRFTGSGSGTDFTLTISNVQSEDLADYFCQQYSSYPYTFGGGTKLEIK |
| 8A10_CP8_VL_ | (196) | DIVMTQSQKFMSTTLGERVSITCKPSQ̲VGS̲VTWWQQKPGQSPKLLIYSAS̲NRYTGVPDRFTGSGSGTDFTLTISNVQSEDLADYFCQQYSSYPYTFGGGTKLEIK |
| 8A10_CP9_VL_ | (197) | DIVMTQSQKFMSTTLGERVSITCKPSQ̲VGS̲VTWWQQKPGQSPKLLIYSAS̲NRYTGVPDRFTGSGSGTDFTLTISNVQSEDLADYFCQQYSSYPYTFGGGTKLEIK |

VH ALIGNMENT

| | | |
|---|---|---|
| 8A10_VH | (10) | EVQLQQSGPELVKPGASVKISCKASGYTFTDSTMNWVKQSHGKSLEWIGEIPNNGGTNYNQKFKGKATLTVDKSSSTAYMELRSLTSEDSAVYYCARGVWGQGTTLTVSS |
| 8A10_CP2_VH_ | (198) | EVQLQQSGPELVKPGASVKISCKASGYTFTDSTMNWVKQSHGKSLEWIGEIPNNGGTNYNQKFKGKATLTVDKSSSTAYMELRSLTSEDSAVYYCARGVWGQGTTLTVSS |
| 8A10_CP3_VH_ | (199) | EVQLQQSGPELVKPGASVKISCKASGYTFTDSTMNWVKQSHGKSLEWIGEIPNNGGTNYNQKFKGKATLTVDKSSSTAYMELRSLTSEDSAVYYCARGVWGQGTTLTVSS |
| 8A10_CP4_VH_ | (200) | EVQLQQSGPELVKPGASVKISCKASGYTFTDSTMNWVKQSHGKSLEWIGEIPNNGGTNYNQKFKGKATLTVDKSSSTAYMELRSLTSEDSAVYYCARGVWGQGTTLTVSS |
| 8A10_CP5_VH_ | (201) | EVQLQQSGPELVKPGASVKISCKASGYTFTDSTMNWVKQSHGKSLEWIGEIPNNGGTNYNQKFKGKATLTVDKSSSTAYMELRSLTSEDSAVYYCARGVWGQGTTLTVSS |
| 8A10_CP6_VH_ | (202) | EVQLQQSGPELVKPGASVKISCKASGYTFTDSTMNWVKQSHGKSLEWIGEIPNNGGTNYNQKFKGKATLTVDKSSSTAYMELRSLTSEDSAVYYCARGVWGQGTTLTVSS |
| 8A10_CP7_VH_ | (203) | EVQLQQSGPELVKPGASVKISCKASGYTFTDSTMNWVKQSHGKSLEWIGEIPNNGGTNYNQKFKGKATLTVDKSSSTAYMELRSLTSEDSAVYYCARGVWGQGTTLTVSS |
| 8A10_CP8_VH_ | (204) | EVQLQQSGPELVKPGASVKISCKASGYTFTDSTMNWVKQSHGKSLEWIGEIPNNGGTNYNQKFKGKATLTVDKSSSTAYMELRSLTSEDSAVYYCARGVWGQGTTLTVSS |
| 8A10_CP9_VH_ | (205) | EVQLQQSGPELVKPGASVKISCKASGYTFTDSTMNWVKQSHGKSLEWIGEIPNNGGTNYNQKFKGKATLTVDKSSSTAYMELRSLTSEDSAVYYCARGVWGQGTTLTVSS |

Amino acid sequence alignment of variable regions obtained from the 3C6 light chain CDR libararies

FIG. 10

Amino acid sequence alignment of variable regions obtained from the 3C6 light chain CDR libararies

SEQUENCE LISTING

```
<160> NUMBER OF SEQ ID NOS: 248

<210> SEQ ID NO 1
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: Wherein X at position 3 is S or V
<220> FEATURE:
<221> NAME/KEY: MISC_FEATURE
<222> LOCATION: (5)..(5)
<223> OTHER INFORMATION: Wherein X at position 5 is N, T, D, M, R, or K
<220> FEATURE:
<221> NAME/KEY: MISC_FEATURE
```

```
<222> LOCATION: (7)..(7)
<223> OTHER INFORMATION: Wherein X at position 7 is G or F
<220> FEATURE:
<221> NAME/KEY: MISC_FEATURE
<222> LOCATION: (9)..(9)
<223> OTHER INFORMATION: Wherein X at position 9 is A, P, or R
<220> FEATURE:
<221> NAME/KEY: MISC_FEATURE
<222> LOCATION: (11)..(11)
<223> OTHER INFORMATION: Wherein X at position 11 is T, N, or A

<400> SEQUENCE: 1

Lys Pro Xaa Gln Xaa Val Xaa Ser Xaa Val Xaa
1               5                   10

<210> SEQ ID NO 2
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Wherein X at position 1 is S or Y
<220> FEATURE:
<221> NAME/KEY: MISC_FEATURE
<222> LOCATION: (2)..(2)
<223> OTHER INFORMATION: Wherein X at position 2 is A, H, or T
<220> FEATURE:
<221> NAME/KEY: MISC_FEATURE
<222> LOCATION: (3)..(3)
<223> OTHER INFORMATION: Wherein X at position 3 is S or T
<220> FEATURE:
<221> NAME/KEY: MISC_FEATURE
<222> LOCATION: (4)..(4)
<223> OTHER INFORMATION: Wherein X at position 4 is N or R
<220> FEATURE:
<221> NAME/KEY: MISC_FEATURE
<222> LOCATION: (7)..(7)
<223> OTHER INFORMATION: Wherein X at position 7 is T, M, or R

<400> SEQUENCE: 2

Xaa Xaa Xaa Xaa Arg Tyr Xaa
1               5

<210> SEQ ID NO 3
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: Wherein X at position 4 is S or P
<220> FEATURE:
<221> NAME/KEY: MISC_FEATURE
<222> LOCATION: (6)..(6)
<223> OTHER INFORMATION: Wherein X at position 6 is Y, K, R, or V
<220> FEATURE:
<221> NAME/KEY: MISC_FEATURE
<222> LOCATION: (9)..(9)
<223> OTHER INFORMATION: Wherein X at position 9 is T or R

<400> SEQUENCE: 3

Gln Gln Tyr Xaa Ser Xaa Pro Tyr Xaa
1               5

<210> SEQ ID NO 4
<211> LENGTH: 10
<212> TYPE: PRT
<213> ORGANISM: Artificial Sequence
```

-continued

```
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Wherein X at position 2 is Y or S
<220> FEATURE:
<221> NAME/KEY: MISC_FEATURE
<222> LOCATION: (3)..(3)
<223> OTHER INFORMATION: Wherein X at position 3 is T or R
<220> FEATURE:
<221> NAME/KEY: MISC_FEATURE
<222> LOCATION: (5)..(5)
<223> OTHER INFORMATION: Wherein X at position 5 is T, S, or H
<220> FEATURE:
<221> NAME/KEY: MISC_FEATURE
<222> LOCATION: (7)..(7)
<223> OTHER INFORMATION: Wherein X at position 7 is S or Y
<220> FEATURE:
<221> NAME/KEY: MISC_FEATURE
<222> LOCATION: (8)..(8)
<223> OTHER INFORMATION: Wherein X at position 8 is T or R
<220> FEATURE:
<221> NAME/KEY: MISC_FEATURE
<222> LOCATION: (9)..(9)
<223> OTHER INFORMATION: Wherein X at position 9 is M or T
<220> FEATURE:
<221> NAME/KEY: MISC_FEATURE
<222> LOCATION: (10)..(10)
<223> OTHER INFORMATION: Wherein X at position 10 is N or K

<400> SEQUENCE: 4

Gly Xaa Xaa Phe Xaa Asp Xaa Xaa Xaa Xaa
1               5                   10

<210> SEQ ID NO 5
<211> LENGTH: 17
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Wherein X at position 1 is E or K
<220> FEATURE:
<221> NAME/KEY: MISC_FEATURE
<222> LOCATION: (3)..(3)
<223> OTHER INFORMATION: Wherein X at position 3 is D, F, W, or A
<220> FEATURE:
<221> NAME/KEY: MISC_FEATURE
<222> LOCATION: (5)..(5)
<223> OTHER INFORMATION: Wherein X at position 5 is N, T, M, S, K, W, or
      R
<220> FEATURE:
<221> NAME/KEY: MISC_FEATURE
<222> LOCATION: (6)..(6)
<223> OTHER INFORMATION: Wherein X at position 6 is N, S, D, or R
<220> FEATURE:
<221> NAME/KEY: MISC_FEATURE
<222> LOCATION: (7)..(7)
<223> OTHER INFORMATION: Wherein X at position 7 is G or L
<220> FEATURE:
<221> NAME/KEY: MISC_FEATURE
<222> LOCATION: (8)..(8)
<223> OTHER INFORMATION: Wherein X at position 8 is G, W, or R
<220> FEATURE:
<221> NAME/KEY: MISC_FEATURE
<222> LOCATION: (9)..(9)
<223> OTHER INFORMATION: Wherein X at position 9 is T or A
<220> FEATURE:
<221> NAME/KEY: MISC_FEATURE
<222> LOCATION: (10)..(10)
<223> OTHER INFORMATION: Wherein X at position 10 is N, R, or A
<220> FEATURE:
<221> NAME/KEY: MISC_FEATURE
<222> LOCATION: (11)..(11)
```

```
<223> OTHER INFORMATION: Wherein X at position 11 is Y or T
<220> FEATURE:
<221> NAME/KEY: MISC_FEATURE
<222> LOCATION: (14)..(14)
<223> OTHER INFORMATION: Wherein X at position 14 is K or N
<220> FEATURE:
<221> NAME/KEY: MISC_FEATURE
<222> LOCATION: (16)..(16)
<223> OTHER INFORMATION: Wherein X at position 16 is K or S
<220> FEATURE:
<221> NAME/KEY: MISC_FEATURE
<222> LOCATION: (17)..(17)
<223> OTHER INFORMATION: Wherein X at position 17 is G or L

<400> SEQUENCE: 5

Xaa Ile Xaa Pro Xaa Xaa Xaa Xaa Xaa Xaa Xaa Asn Gln Xaa Phe Xaa
1               5                   10                  15

Xaa

<210> SEQ ID NO 6
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: Wherein X at position 3 is G, L, or P
<220> FEATURE:
<221> NAME/KEY: MISC_FEATURE
<222> LOCATION: (4)..(4)
<223> OTHER INFORMATION: Wherein X at position 4 is V, P or S

<400> SEQUENCE: 6

Ala Arg Xaa Xaa Trp Gly
1               5

<210> SEQ ID NO 7
<211> LENGTH: 323
<212> TYPE: DNA
<213> ORGANISM: Artificial Sequence
<220> FEATURE:
<223> OTHER INFORMATION: Synthetic

<400> SEQUENCE: 7
gacattgtga tgacccagtc tcaaaaattc atgtccataa cactaggaga gagggtcagc      60
atcacctgca agcccagtca gaatgtgggt tctgctgtaa cctggtggca acagaaacca     120
ggacaatctc ctaaactact gatttactca gcttccaatc ggtatactgg agtccctgat     180
cgcttcacag gcagtggatc tgggacagat ttcactctca ccattagtaa tgtgcagtct     240
gaagacctgg cagattattt ctgtcaacaa tatagcagct atccgtacac gttcggaggg     300
gggaccaagc tggaaataaa acg                                             323

<210> SEQ ID NO 8
<211> LENGTH: 106
<212> TYPE: PRT
<213> ORGANISM: Artificial Sequence
<220> FEATURE:
<223> OTHER INFORMATION: Synthetic

<400> SEQUENCE: 8

Asp Ile Val Met Thr Gln Ser Gln Lys Phe Met Ser Ile Thr Leu Gly
1               5                   10                  15

Glu Arg Val Ser Ile Thr Cys Lys Pro Ser Gln Asn Val Gly Ser Ala
            20                  25                  30
```

Val Thr Trp Trp Gln Gln Lys Pro Gly Gln Ser Pro Lys Leu Leu Ile
            35                  40                  45

Tyr Ser Ala Ser Asn Arg Tyr Thr Gly Val Pro Asp Arg Phe Thr Gly
        50                  55                  60

Ser Gly Ser Gly Thr Asp Phe Thr Leu Thr Ile Ser Asn Val Gln Ser
65                  70                  75                  80

Glu Asp Leu Ala Asp Tyr Phe Cys Gln Gln Tyr Ser Ser Tyr Pro Tyr
                85                  90                  95

Thr Phe Gly Gly Thr Lys Leu Glu Ile Lys
            100                 105

<210> SEQ ID NO 9
<211> LENGTH: 333
<212> TYPE: DNA
<213> ORGANISM: Artificial Sequence
<220> FEATURE:
<223> OTHER INFORMATION: Synthetic

<400> SEQUENCE: 9
gaggtccagc tgcaacaatc tggacctgaa ctggtgaagc ctggggcttc agtgaagatt      60
tcctgtaagg cttctggata cacgttcact gactccacca tgaactgggt gaagcagagc     120
catggaaaga gccttgagtg gattggagag attgatccta acaatggtgg tactaactac     180
aatcagaagt tcaagggcaa ggccacattg actgtagaca gtcctccag cacagcctat      240 atggagctcc gcagcctgac atctgaggac tctgcagtct attactgtgc aagaggggtc     300
tggggccaag gcaccactct cacagtctcc tca                                  333

<210> SEQ ID NO 10
<211> LENGTH: 111
<212> TYPE: PRT
<213> ORGANISM: Artificial Sequence
<220> FEATURE:
<223> OTHER INFORMATION: Synthetic

<400> SEQUENCE: 10

Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Thr Phe Thr Asp Ser
            20                  25                  30

Thr Met Asn Trp Val Lys Gln Ser His Gly Lys Ser Leu Glu Trp Ile
        35                  40                  45

Gly Glu Ile Asp Pro Asn Asn Gly Gly Thr Asn Tyr Asn Gln Lys Phe
    50                  55                  60

Lys Gly Lys Ala Thr Leu Thr Val Asp Lys Ser Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Arg Gly Val Trp Gly Gln Gly Thr Thr Leu Thr Val Ser Ser
            100                 105                 110

<210> SEQ ID NO 11
<211> LENGTH: 11
<212> TYPE: PRT
<213> ORGANISM: Artificial Sequence
<220> FEATURE:
<223> OTHER INFORMATION: Synthetic

<400> SEQUENCE: 11

Lys Pro Ser Gln Asn Val Gly Ser Ala Val Thr
1               5                   10

<210> SEQ ID NO 12
<211> LENGTH: 11
<212> TYPE: PRT
<213> ORGANISM: Artificial Sequence
<220> FEATURE:
<223> OTHER INFORMATION: Synthetic

<400> SEQUENCE: 12

Lys Pro Ser Gln Asn Val Phe Ser Ala Val Thr
1               5                   10

<210> SEQ ID NO 13
<211> LENGTH: 11
<212> TYPE: PRT
<213> ORGANISM: Artificial Sequence
<220> FEATURE:
<223> OTHER INFORMATION: Synthetic

<400> SEQUENCE: 13

Lys Pro Ser Gln Thr Val Gly Ser Ala Val Thr
1               5                   10

<210> SEQ ID NO 14
<211> LENGTH: 11
<212> TYPE: PRT
<213> ORGANISM: Artificial Sequence
<220> FEATURE:
<223> OTHER INFORMATION: Synthetic

<400> SEQUENCE: 14

Lys Pro Val Gln Asn Val Gly Ser Ala Val Thr
1               5                   10

<210> SEQ ID NO 15
<211> LENGTH: 11
<212> TYPE: PRT
<213> ORGANISM: Artificial Sequence
<220> FEATURE:
<223> OTHER INFORMATION: Synthetic

<400> SEQUENCE: 15

Lys Pro Ser Gln Asn Val Phe Ser Ala Val Thr
1               5                   10

<210> SEQ ID NO 16
<211> LENGTH: 11
<212> TYPE: PRT
<213> ORGANISM: Artificial Sequence
<220> FEATURE:
<223> OTHER INFORMATION: Synthetic

<400> SEQUENCE: 16

Lys Pro Ser Gln Asp Val Gly Ser Ala Val Thr
1               5                   10

<210> SEQ ID NO 17
<211> LENGTH: 11
<212> TYPE: PRT
<213> ORGANISM: Artificial Sequence
<220> FEATURE:
<223> OTHER INFORMATION: Synthetic

<400> SEQUENCE: 17

Lys Pro Ser Gln Asn Val Phe Ser Ala Val Thr

```
<210> SEQ ID NO 18
<211> LENGTH: 11
<212> TYPE: PRT
<213> ORGANISM: Artificial Sequence
<220> FEATURE:
<223> OTHER INFORMATION: Synthetic

<400> SEQUENCE: 18

Lys Pro Ser Gln Met Val Gly Ser Ala Val Thr
1               5                   10

<210> SEQ ID NO 19
<211> LENGTH: 11
<212> TYPE: PRT
<213> ORGANISM: Artificial Sequence
<220> FEATURE:
<223> OTHER INFORMATION: Synthetic

<400> SEQUENCE: 19

Lys Pro Ser Gln Asn Val Gly Ser Pro Val Asn
1               5                   10

<210> SEQ ID NO 20
<211> LENGTH: 11
<212> TYPE: PRT
<213> ORGANISM: Artificial Sequence
<220> FEATURE:
<223> OTHER INFORMATION: Synthetic

<400> SEQUENCE: 20

Lys Pro Ser Gln Arg Val Gly Ser Ala Val Thr
1               5                   10

<210> SEQ ID NO 21
<211> LENGTH: 11
<212> TYPE: PRT
<213> ORGANISM: Artificial Sequence
<220> FEATURE:
<223> OTHER INFORMATION: Synthetic

<400> SEQUENCE: 21

Lys Pro Ser Gln Arg Val Gly Ser Ala Val Thr
1               5                   10

<210> SEQ ID NO 22
<211> LENGTH: 11
<212> TYPE: PRT
<213> ORGANISM: Artificial Sequence
<220> FEATURE:
<223> OTHER INFORMATION: Synthetic

<400> SEQUENCE: 22

Lys Pro Ser Gln Lys Val Gly Ser Ala Val Thr
1               5                   10

<210> SEQ ID NO 23
<211> LENGTH: 11
<212> TYPE: PRT
<213> ORGANISM: Artificial Sequence
<220> FEATURE:
<223> OTHER INFORMATION: Synthetic

<400> SEQUENCE: 23

Lys Pro Ser Gln Asn Val Gly Ser Arg Val Thr
1               5                   10
```

<210> SEQ ID NO 24
<211> LENGTH: 11
<212> TYPE: PRT
<213> ORGANISM: Artificial Sequence
<220> FEATURE:
<223> OTHER INFORMATION: Synthetic

<400> SEQUENCE: 24

Lys Pro Ser Gln Lys Val Gly Ser Ala Val Thr
1               5                   10

<210> SEQ ID NO 25
<211> LENGTH: 11
<212> TYPE: PRT
<213> ORGANISM: Artificial Sequence
<220> FEATURE:
<223> OTHER INFORMATION: Synthetic

<400> SEQUENCE: 25

Lys Pro Ser Gln Asn Val Gly Ser Ala Val Asn
1               5                   10

<210> SEQ ID NO 26
<211> LENGTH: 11
<212> TYPE: PRT
<213> ORGANISM: Artificial Sequence
<220> FEATURE:
<223> OTHER INFORMATION: Synthetic

<400> SEQUENCE: 26

Lys Pro Ser Gln Asn Val Gly Ser Ala Val Ala
1               5                   10

<210> SEQ ID NO 27
<211> LENGTH: 11
<212> TYPE: PRT
<213> ORGANISM: Artificial Sequence
<220> FEATURE:
<223> OTHER INFORMATION: Synthetic

<400> SEQUENCE: 27

Lys Pro Ser Gln Asn Val Gly Ser Arg Val Thr
1               5                   10

<210> SEQ ID NO 28
<211> LENGTH: 11
<212> TYPE: PRT
<213> ORGANISM: Artificial Sequence
<220> FEATURE:
<223> OTHER INFORMATION: Synthetic

<400> SEQUENCE: 28

Lys Pro Ser Gln Asn Val Gly Ser Arg Val Thr
1               5                   10

<210> SEQ ID NO 29
<211> LENGTH: 11
<212> TYPE: PRT
<213> ORGANISM: Artificial Sequence
<220> FEATURE:
<223> OTHER INFORMATION: Synthetic

<400> SEQUENCE: 29

Lys Pro Val Gln Asn Val Gly Ser Ala Val Thr
1               5                   10

```
<210> SEQ ID NO 30
<211> LENGTH: 11
<212> TYPE: PRT
<213> ORGANISM: Artificial Sequence
<220> FEATURE:
<223> OTHER INFORMATION: Synthetic

<400> SEQUENCE: 30

Lys Pro Ser Gln Lys Val Gly Ser Ala Val Thr
1               5                   10

<210> SEQ ID NO 31
<211> LENGTH: 7
<212> TYPE: PRT
<213> ORGANISM: Artificial Sequence
<220> FEATURE:
<223> OTHER INFORMATION: Synthetic

<400> SEQUENCE: 31

Ser Ala Ser Asn Arg Tyr Thr
1               5

<210> SEQ ID NO 32
<211> LENGTH: 7
<212> TYPE: PRT
<213> ORGANISM: Artificial Sequence
<220> FEATURE:
<223> OTHER INFORMATION: Synthetic

<400> SEQUENCE: 32

Ser Ala Thr Asn Arg Tyr Thr
1               5

<210> SEQ ID NO 33
<211> LENGTH: 7
<212> TYPE: PRT
<213> ORGANISM: Artificial Sequence
<220> FEATURE:
<223> OTHER INFORMATION: Synthetic

<400> SEQUENCE: 33

Ser Ala Ser Asn Arg Tyr Met
1               5

<210> SEQ ID NO 34
<211> LENGTH: 7
<212> TYPE: PRT
<213> ORGANISM: Artificial Sequence
<220> FEATURE:
<223> OTHER INFORMATION: Synthetic

<400> SEQUENCE: 34

Tyr Ala Ser Asn Arg Tyr Thr
1               5

<210> SEQ ID NO 35
<211> LENGTH: 7
<212> TYPE: PRT
<213> ORGANISM: Artificial Sequence
<220> FEATURE:
<223> OTHER INFORMATION: Synthetic

<400> SEQUENCE: 35

Ser His Ser Asn Arg Tyr Thr
1               5
```

```
<210> SEQ ID NO 36
<211> LENGTH: 7
<212> TYPE: PRT
<213> ORGANISM: Artificial Sequence
<220> FEATURE:
<223> OTHER INFORMATION: Synthetic

<400> SEQUENCE: 36

Ser Thr Ser Asn Arg Tyr Thr
1               5

<210> SEQ ID NO 37
<211> LENGTH: 7
<212> TYPE: PRT
<213> ORGANISM: Artificial Sequence
<220> FEATURE:
<223> OTHER INFORMATION: Synthetic

<400> SEQUENCE: 37

Ser Ala Thr Asn Arg Tyr Thr
1               5

<210> SEQ ID NO 38
<211> LENGTH: 7
<212> TYPE: PRT
<213> ORGANISM: Artificial Sequence
<220> FEATURE:
<223> OTHER INFORMATION: Synthetic

<400> SEQUENCE: 38

Ser Thr Ser Asn Arg Tyr Thr
1               5

<210> SEQ ID NO 39
<211> LENGTH: 7
<212> TYPE: PRT
<213> ORGANISM: Artificial Sequence
<220> FEATURE:
<223> OTHER INFORMATION: Synthetic

<400> SEQUENCE: 39

Ser Ala Ser Arg Arg Tyr Thr
1               5

<210> SEQ ID NO 40
<211> LENGTH: 7
<212> TYPE: PRT
<213> ORGANISM: Artificial Sequence
<220> FEATURE:
<223> OTHER INFORMATION: Synthetic

<400> SEQUENCE: 40

Ser Ala Ser Arg Arg Tyr Thr
1               5

<210> SEQ ID NO 41
<211> LENGTH: 7
<212> TYPE: PRT
<213> ORGANISM: Artificial Sequence
<220> FEATURE:
<223> OTHER INFORMATION: Synthetic

<400> SEQUENCE: 41

Ser Ala Ser Arg Arg Tyr Thr
1               5

<210> SEQ ID NO 42
```

```
<211> LENGTH: 7
<212> TYPE: PRT
<213> ORGANISM: Artificial Sequence
<220> FEATURE:
<223> OTHER INFORMATION: Synthetic

<400> SEQUENCE: 42

Ser Ala Ser Arg Arg Tyr Thr
1               5

<210> SEQ ID NO 43
<211> LENGTH: 7
<212> TYPE: PRT
<213> ORGANISM: Artificial Sequence
<220> FEATURE:
<223> OTHER INFORMATION: Synthetic

<400> SEQUENCE: 43

Ser Ala Ser Asn Arg Tyr Arg
1               5

<210> SEQ ID NO 44
<211> LENGTH: 7
<212> TYPE: PRT
<213> ORGANISM: Artificial Sequence
<220> FEATURE:
<223> OTHER INFORMATION: Synthetic

<400> SEQUENCE: 44

Ser Ala Ser Arg Arg Tyr Thr
1               5

<210> SEQ ID NO 45
<211> LENGTH: 9
<212> TYPE: PRT
<213> ORGANISM: Artificial Sequence
<220> FEATURE:
<223> OTHER INFORMATION: Synthetic

<400> SEQUENCE: 45

Gln Gln Tyr Ser Ser Tyr Pro Tyr Thr
1               5

<210> SEQ ID NO 46
<211> LENGTH: 9
<212> TYPE: PRT
<213> ORGANISM: Artificial Sequence
<220> FEATURE:
<223> OTHER INFORMATION: Synthetic

<400> SEQUENCE: 46

Gln Gln Tyr Ser Ser Lys Pro Tyr Thr
1               5

<210> SEQ ID NO 47
<211> LENGTH: 9
<212> TYPE: PRT
<213> ORGANISM: Artificial Sequence
<220> FEATURE:
<223> OTHER INFORMATION: Synthetic

<400> SEQUENCE: 47

Gln Gln Tyr Pro Ser Tyr Pro Tyr Thr
1               5

<210> SEQ ID NO 48
<211> LENGTH: 9
```

```
<212> TYPE: PRT
<213> ORGANISM: Artificial Sequence
<220> FEATURE:
<223> OTHER INFORMATION: Synthetic

<400> SEQUENCE: 48

Gln Gln Tyr Ser Ser Tyr Pro Tyr Arg
1               5

<210> SEQ ID NO 49
<211> LENGTH: 9
<212> TYPE: PRT
<213> ORGANISM: Artificial Sequence
<220> FEATURE:
<223> OTHER INFORMATION: Synthetic

<400> SEQUENCE: 49

Gln Gln Tyr Ser Ser Arg Pro Tyr Thr
1               5

<210> SEQ ID NO 50
<211> LENGTH: 9
<212> TYPE: PRT
<213> ORGANISM: Artificial Sequence
<220> FEATURE:
<223> OTHER INFORMATION: Synthetic

<400> SEQUENCE: 50

Gln Gln Tyr Ser Ser Arg Pro Tyr Thr
1               5

<210> SEQ ID NO 51
<211> LENGTH: 9
<212> TYPE: PRT
<213> ORGANISM: Artificial Sequence
<220> FEATURE:
<223> OTHER INFORMATION: Synthetic

<400> SEQUENCE: 51

Gln Gln Tyr Ser Ser Arg Pro Tyr Thr
1               5

<210> SEQ ID NO 52
<211> LENGTH: 9
<212> TYPE: PRT
<213> ORGANISM: Artificial Sequence
<220> FEATURE:
<223> OTHER INFORMATION: Synthetic

<400> SEQUENCE: 52

Gln Gln Tyr Ser Ser Arg Pro Tyr Thr
1               5

<210> SEQ ID NO 53
<211> LENGTH: 9
<212> TYPE: PRT
<213> ORGANISM: Artificial Sequence
<220> FEATURE:
<223> OTHER INFORMATION: Synthetic

<400> SEQUENCE: 53

Gln Gln Tyr Ser Ser Lys Pro Tyr Thr
1               5

<210> SEQ ID NO 54
<211> LENGTH: 9
<212> TYPE: PRT
```

```
<213> ORGANISM: Artificial Sequence
<220> FEATURE:
<223> OTHER INFORMATION: Synthetic

<400> SEQUENCE: 54

Gln Gln Tyr Ser Ser Lys Pro Tyr Thr
1               5

<210> SEQ ID NO 55
<211> LENGTH: 9
<212> TYPE: PRT
<213> ORGANISM: Artificial Sequence
<220> FEATURE:
<223> OTHER INFORMATION: Synthetic

<400> SEQUENCE: 55

Gln Gln Tyr Ser Ser Val Pro Tyr Thr
1               5

<210> SEQ ID NO 56
<211> LENGTH: 9
<212> TYPE: PRT
<213> ORGANISM: Artificial Sequence
<220> FEATURE:
<223> OTHER INFORMATION: Synthetic

<400> SEQUENCE: 56

Gln Gln Tyr Ser Ser Arg Pro Tyr Thr
1               5

<210> SEQ ID NO 57
<211> LENGTH: 9
<212> TYPE: PRT
<213> ORGANISM: Artificial Sequence
<220> FEATURE:
<223> OTHER INFORMATION: Synthetic

<400> SEQUENCE: 57

Gln Gln Tyr Ser Ser Lys Pro Tyr Thr
1               5

<210> SEQ ID NO 58
<211> LENGTH: 10
<212> TYPE: PRT
<213> ORGANISM: Artificial Sequence
<220> FEATURE:
<223> OTHER INFORMATION: Synthetic

<400> SEQUENCE: 58

Gly Tyr Thr Phe Thr Asp Ser Thr Met Asn
1               5                   10

<210> SEQ ID NO 59
<211> LENGTH: 10
<212> TYPE: PRT
<213> ORGANISM: Artificial Sequence
<220> FEATURE:
<223> OTHER INFORMATION: Synthetic

<400> SEQUENCE: 59

Gly Tyr Thr Phe Thr Asp Tyr Thr Met Asn
1               5                   10

<210> SEQ ID NO 60
<211> LENGTH: 10
<212> TYPE: PRT
<213> ORGANISM: Artificial Sequence
```

```
<220> FEATURE:
<223> OTHER INFORMATION: Synthetic

<400> SEQUENCE: 60

Gly Ser Thr Phe Thr Asp Ser Thr Met Asn
1               5                   10

<210> SEQ ID NO 61
<211> LENGTH: 10
<212> TYPE: PRT
<213> ORGANISM: Artificial Sequence
<220> FEATURE:
<223> OTHER INFORMATION: Synthetic

<400> SEQUENCE: 61

Gly Tyr Thr Phe Thr Asp Ser Thr Thr Asn
1               5                   10

<210> SEQ ID NO 62
<211> LENGTH: 10
<212> TYPE: PRT
<213> ORGANISM: Artificial Sequence
<220> FEATURE:
<223> OTHER INFORMATION: Synthetic

<400> SEQUENCE: 62

Gly Tyr Thr Phe Ser Asp Ser Thr Met Asn
1               5                   10

<210> SEQ ID NO 63
<211> LENGTH: 10
<212> TYPE: PRT
<213> ORGANISM: Artificial Sequence
<220> FEATURE:
<223> OTHER INFORMATION: Synthetic

<400> SEQUENCE: 63

Gly Tyr Thr Phe Thr Asp Ser Thr Met Lys
1               5                   10

<210> SEQ ID NO 64
<211> LENGTH: 10
<212> TYPE: PRT
<213> ORGANISM: Artificial Sequence
<220> FEATURE:
<223> OTHER INFORMATION: Synthetic

<400> SEQUENCE: 64

Gly Tyr Arg Phe Thr Asp Ser Thr Met Asn
1               5                   10

<210> SEQ ID NO 65
<211> LENGTH: 10
<212> TYPE: PRT
<213> ORGANISM: Artificial Sequence
<220> FEATURE:
<223> OTHER INFORMATION: Synthetic

<400> SEQUENCE: 65

Gly Tyr Thr Phe His Asp Ser Thr Met Asn
1               5                   10

<210> SEQ ID NO 66
<211> LENGTH: 10
<212> TYPE: PRT
<213> ORGANISM: Artificial Sequence
<220> FEATURE:
```

<223> OTHER INFORMATION: Synthetic

<400> SEQUENCE: 66

Gly Tyr Arg Phe Thr Asp Ser Thr Met Asn
1               5                   10

<210> SEQ ID NO 67
<211> LENGTH: 10
<212> TYPE: PRT
<213> ORGANISM: Artificial Sequence
<220> FEATURE:
<223> OTHER INFORMATION: Synthetic

<400> SEQUENCE: 67

Gly Tyr Thr Phe Thr Asp Ser Arg Met Asn
1               5                   10

<210> SEQ ID NO 68
<211> LENGTH: 17
<212> TYPE: PRT
<213> ORGANISM: Artificial Sequence
<220> FEATURE:
<223> OTHER INFORMATION: Synthetic

<400> SEQUENCE: 68

Glu Ile Asp Pro Asn Asn Gly Gly Thr Asn Tyr Asn Gln Lys Phe Lys
1               5                   10                  15
Gly

<210> SEQ ID NO 69
<211> LENGTH: 8
<212> TYPE: PRT
<213> ORGANISM: Artificial Sequence
<220> FEATURE:
<223> OTHER INFORMATION: Synthetic

<400> SEQUENCE: 69

Glu Ile Asp Pro Asn Asn Gly Gly
1               5

<210> SEQ ID NO 70
<211> LENGTH: 8
<212> TYPE: PRT
<213> ORGANISM: Artificial Sequence
<220> FEATURE:
<223> OTHER INFORMATION: Synthetic

<400> SEQUENCE: 70

Glu Ile Asp Pro Thr Asn Gly Gly
1               5

<210> SEQ ID NO 71
<211> LENGTH: 8
<212> TYPE: PRT
<213> ORGANISM: Artificial Sequence
<220> FEATURE:
<223> OTHER INFORMATION: Synthetic

<400> SEQUENCE: 71

Glu Ile Asp Pro Asn Asn Leu Gly
1               5

<210> SEQ ID NO 72
<211> LENGTH: 8
<212> TYPE: PRT
<213> ORGANISM: Artificial Sequence

```
<220> FEATURE:
<223> OTHER INFORMATION: Synthetic

<400> SEQUENCE: 72

Glu Ile Asp Pro Asn Asn Gly Trp
1               5

<210> SEQ ID NO 73
<211> LENGTH: 8
<212> TYPE: PRT
<213> ORGANISM: Artificial Sequence
<220> FEATURE:
<223> OTHER INFORMATION: Synthetic

<400> SEQUENCE: 73

Glu Ile Asp Pro Asn Ser Gly Gly
1               5

<210> SEQ ID NO 74
<211> LENGTH: 8
<212> TYPE: PRT
<213> ORGANISM: Artificial Sequence
<220> FEATURE:
<223> OTHER INFORMATION: Synthetic

<400> SEQUENCE: 74

Lys Ile Asp Pro Asn Asn Gly Gly
1               5

<210> SEQ ID NO 75
<211> LENGTH: 8
<212> TYPE: PRT
<213> ORGANISM: Artificial Sequence
<220> FEATURE:
<223> OTHER INFORMATION: Synthetic

<400> SEQUENCE: 75

Glu Ile Asp Pro Met Asn Gly Gly
1               5

<210> SEQ ID NO 76
<211> LENGTH: 8
<212> TYPE: PRT
<213> ORGANISM: Artificial Sequence
<220> FEATURE:
<223> OTHER INFORMATION: Synthetic

<400> SEQUENCE: 76

Glu Ile Asp Pro Asn Asp Gly Gly
1               5

<210> SEQ ID NO 77
<211> LENGTH: 8
<212> TYPE: PRT
<213> ORGANISM: Artificial Sequence
<220> FEATURE:
<223> OTHER INFORMATION: Synthetic

<400> SEQUENCE: 77

Glu Ile Asp Pro Ser Asn Gly Gly
1               5

<210> SEQ ID NO 78
<211> LENGTH: 8
<212> TYPE: PRT
<213> ORGANISM: Artificial Sequence
<220> FEATURE:
```

<223> OTHER INFORMATION: Synthetic

<400> SEQUENCE: 78

Glu Ile Asp Pro Lys Asn Gly Gly
1               5

<210> SEQ ID NO 79
<211> LENGTH: 8
<212> TYPE: PRT
<213> ORGANISM: Artificial Sequence
<220> FEATURE:
<223> OTHER INFORMATION: Synthetic

<400> SEQUENCE: 79

Glu Ile Asp Pro Trp Asn Gly Gly
1               5

<210> SEQ ID NO 80
<211> LENGTH: 8
<212> TYPE: PRT
<213> ORGANISM: Artificial Sequence
<220> FEATURE:
<223> OTHER INFORMATION: Synthetic

<400> SEQUENCE: 80

Glu Ile Asp Pro Arg Asn Gly Gly
1               5

<210> SEQ ID NO 81
<211> LENGTH: 8
<212> TYPE: PRT
<213> ORGANISM: Artificial Sequence
<220> FEATURE:
<223> OTHER INFORMATION: Synthetic

<400> SEQUENCE: 81

Glu Ile Asp Pro Asn Asn Gly Arg
1               5

<210> SEQ ID NO 82
<211> LENGTH: 8
<212> TYPE: PRT
<213> ORGANISM: Artificial Sequence
<220> FEATURE:
<223> OTHER INFORMATION: Synthetic

<400> SEQUENCE: 82

Glu Ile Asp Pro Arg Asn Gly Gly
1               5

<210> SEQ ID NO 83
<211> LENGTH: 8
<212> TYPE: PRT
<213> ORGANISM: Artificial Sequence
<220> FEATURE:
<223> OTHER INFORMATION: Synthetic

<400> SEQUENCE: 83

Glu Ile Asp Pro Trp Asn Gly Gly
1               5

<210> SEQ ID NO 84
<211> LENGTH: 8
<212> TYPE: PRT
<213> ORGANISM: Artificial Sequence
<220> FEATURE:
<223> OTHER INFORMATION: Synthetic

```
<400> SEQUENCE: 84

Glu Ile Phe Pro Asn Asn Gly Gly
1               5

<210> SEQ ID NO 85
<211> LENGTH: 8
<212> TYPE: PRT
<213> ORGANISM: Artificial Sequence
<220> FEATURE:
<223> OTHER INFORMATION: Synthetic

<400> SEQUENCE: 85

Glu Ile Phe Pro Asn Asn Gly Gly
1               5

<210> SEQ ID NO 86
<211> LENGTH: 8
<212> TYPE: PRT
<213> ORGANISM: Artificial Sequence
<220> FEATURE:
<223> OTHER INFORMATION: Synthetic

<400> SEQUENCE: 86

Glu Ile Trp Pro Asn Asn Gly Gly
1               5

<210> SEQ ID NO 87
<211> LENGTH: 8
<212> TYPE: PRT
<213> ORGANISM: Artificial Sequence
<220> FEATURE:
<223> OTHER INFORMATION: Synthetic

<400> SEQUENCE: 87

Glu Ile Ala Pro Asn Asn Gly Gly
1               5

<210> SEQ ID NO 88
<211> LENGTH: 8
<212> TYPE: PRT
<213> ORGANISM: Artificial Sequence
<220> FEATURE:
<223> OTHER INFORMATION: Synthetic

<400> SEQUENCE: 88

Glu Ile Asp Pro Asn Arg Gly Gly
1               5

<210> SEQ ID NO 89
<211> LENGTH: 8
<212> TYPE: PRT
<213> ORGANISM: Artificial Sequence
<220> FEATURE:
<223> OTHER INFORMATION: Synthetic

<400> SEQUENCE: 89

Glu Ile Trp Pro Asn Asn Gly Gly
1               5

<210> SEQ ID NO 90
<211> LENGTH: 8
<212> TYPE: PRT
<213> ORGANISM: Artificial Sequence
<220> FEATURE:
<223> OTHER INFORMATION: Synthetic
```

```
<400> SEQUENCE: 90

Glu Ile Asp Pro Asn Asn Gly Trp
1               5

<210> SEQ ID NO 91
<211> LENGTH: 9
<212> TYPE: PRT
<213> ORGANISM: Artificial Sequence
<220> FEATURE:
<223> OTHER INFORMATION: Synthetic

<400> SEQUENCE: 91

Thr Asn Tyr Asn Gln Lys Phe Lys Gly
1               5

<210> SEQ ID NO 92
<211> LENGTH: 9
<212> TYPE: PRT
<213> ORGANISM: Artificial Sequence
<220> FEATURE:
<223> OTHER INFORMATION: Synthetic

<400> SEQUENCE: 92

Thr Arg Tyr Asn Gln Lys Phe Lys Gly
1               5

<210> SEQ ID NO 93
<211> LENGTH: 9
<212> TYPE: PRT
<213> ORGANISM: Artificial Sequence
<220> FEATURE:
<223> OTHER INFORMATION: Synthetic

<400> SEQUENCE: 93

Thr Asn Thr Asn Gln Lys Phe Lys Gly
1               5

<210> SEQ ID NO 94
<211> LENGTH: 9
<212> TYPE: PRT
<213> ORGANISM: Artificial Sequence
<220> FEATURE:
<223> OTHER INFORMATION: Synthetic

<400> SEQUENCE: 94

Ala Asn Tyr Asn Gln Lys Phe Lys Gly
1               5

<210> SEQ ID NO 95
<211> LENGTH: 9
<212> TYPE: PRT
<213> ORGANISM: Artificial Sequence
<220> FEATURE:
<223> OTHER INFORMATION: Synthetic

<400> SEQUENCE: 95

Thr Asn Tyr Asn Gln Lys Phe Ser Gly
1               5

<210> SEQ ID NO 96
<211> LENGTH: 9
<212> TYPE: PRT
<213> ORGANISM: Artificial Sequence
<220> FEATURE:
<223> OTHER INFORMATION: Synthetic

<400> SEQUENCE: 96
```

Thr Asn Tyr Asn Gln Asn Phe Lys Gly
1               5

<210> SEQ ID NO 97
<211> LENGTH: 9
<212> TYPE: PRT
<213> ORGANISM: Artificial Sequence
<220> FEATURE:
<223> OTHER INFORMATION: Synthetic

<400> SEQUENCE: 97

Thr Ala Tyr Asn Gln Lys Phe Lys Gly
1               5

<210> SEQ ID NO 98
<211> LENGTH: 9
<212> TYPE: PRT
<213> ORGANISM: Artificial Sequence
<220> FEATURE:
<223> OTHER INFORMATION: Synthetic

<400> SEQUENCE: 98

Thr Asn Tyr Asn Gln Lys Phe Lys Leu
1               5

<210> SEQ ID NO 99
<211> LENGTH: 6
<212> TYPE: PRT
<213> ORGANISM: Artificial Sequence
<220> FEATURE:
<223> OTHER INFORMATION: Synthetic

<400> SEQUENCE: 99

Ala Arg Gly Val Trp Gly
1               5

<210> SEQ ID NO 100
<211> LENGTH: 6
<212> TYPE: PRT
<213> ORGANISM: Artificial Sequence
<220> FEATURE:
<223> OTHER INFORMATION: Synthetic

<400> SEQUENCE: 100

Ala Ala Arg Val Trp Gly
1               5

<210> SEQ ID NO 101
<211> LENGTH: 6
<212> TYPE: PRT
<213> ORGANISM: Artificial Sequence
<220> FEATURE:
<223> OTHER INFORMATION: Synthetic

<400> SEQUENCE: 101

Ala Arg Gly Pro Trp Gly
1               5

<210> SEQ ID NO 102
<211> LENGTH: 6
<212> TYPE: PRT
<213> ORGANISM: Artificial Sequence
<220> FEATURE:
<223> OTHER INFORMATION: Synthetic

<400> SEQUENCE: 102

Ala Arg Pro Val Trp Gly
1               5

<210> SEQ ID NO 103
<211> LENGTH: 6
<212> TYPE: PRT
<213> ORGANISM: Artificial Sequence
<220> FEATURE:
<223> OTHER INFORMATION: Synthetic

<400> SEQUENCE: 103

Ala Arg Gly Ser Trp Gly
1               5

<210> SEQ ID NO 104
<211> LENGTH: 11
<212> TYPE: PRT
<213> ORGANISM: Artificial Sequence
<220> FEATURE:
<223> OTHER INFORMATION: Synthetic

<400> SEQUENCE: 104

Lys Pro Ser Gln Lys Val Gly Ser Arg Val Thr
1               5                   10

<210> SEQ ID NO 105
<211> LENGTH: 11
<212> TYPE: PRT
<213> ORGANISM: Artificial Sequence
<220> FEATURE:
<223> OTHER INFORMATION: Synthetic

<400> SEQUENCE: 105

Lys Pro Ser Gln Arg Val Gly Ser Arg Val Thr
1               5                   10

<210> SEQ ID NO 106
<211> LENGTH: 11
<212> TYPE: PRT
<213> ORGANISM: Artificial Sequence
<220> FEATURE:
<223> OTHER INFORMATION: Synthetic

<400> SEQUENCE: 106

Lys Pro Ser Gln Lys Val Gly Ser Ala Val Thr
1               5                   10

<210> SEQ ID NO 107
<211> LENGTH: 11
<212> TYPE: PRT
<213> ORGANISM: Artificial Sequence
<220> FEATURE:
<223> OTHER INFORMATION: Synthetic

<400> SEQUENCE: 107

Lys Pro Ser Gln Lys Val Gly Ser Ala Val Thr
1               5                   10

<210> SEQ ID NO 108
<211> LENGTH: 11
<212> TYPE: PRT
<213> ORGANISM: Artificial Sequence
<220> FEATURE:
<223> OTHER INFORMATION: Synthetic

<400> SEQUENCE: 108

Lys Pro Ser Gln Lys Val Gly Ser Arg Val Thr

```
1               5                  10
```

<210> SEQ ID NO 109
<211> LENGTH: 11
<212> TYPE: PRT
<213> ORGANISM: Artificial Sequence
<220> FEATURE:
<223> OTHER INFORMATION: Synthetic

<400> SEQUENCE: 109

```
Lys Pro Ser Gln Lys Val Gly Ser Arg Val Thr
1               5                  10
```

<210> SEQ ID NO 110
<211> LENGTH: 11
<212> TYPE: PRT
<213> ORGANISM: Artificial Sequence
<220> FEATURE:
<223> OTHER INFORMATION: Synthetic

<400> SEQUENCE: 110

```
Lys Pro Ser Gln Lys Val Gly Ser Ala Val Thr
1               5                  10
```

<210> SEQ ID NO 111
<211> LENGTH: 7
<212> TYPE: PRT
<213> ORGANISM: Artificial Sequence
<220> FEATURE:
<223> OTHER INFORMATION: Synthetic

<400> SEQUENCE: 111

```
Ser Ala Ile Asn Arg Tyr Thr
1               5
```

<210> SEQ ID NO 112
<211> LENGTH: 7
<212> TYPE: PRT
<213> ORGANISM: Artificial Sequence
<220> FEATURE:
<223> OTHER INFORMATION: Synthetic

<400> SEQUENCE: 112

```
Ser Thr Ile Asn Arg Tyr Thr
1               5
```

<210> SEQ ID NO 113
<211> LENGTH: 7
<212> TYPE: PRT
<213> ORGANISM: Artificial Sequence
<220> FEATURE:
<223> OTHER INFORMATION: Synthetic

<400> SEQUENCE: 113

```
Ser Thr Asn Asn Arg Tyr Thr
1               5
```

<210> SEQ ID NO 114
<211> LENGTH: 7
<212> TYPE: PRT
<213> ORGANISM: Artificial Sequence
<220> FEATURE:
<223> OTHER INFORMATION: Synthetic

<400> SEQUENCE: 114

```
Ser Thr Ile Arg Arg Tyr Thr
1               5
```

<210> SEQ ID NO 115
<211> LENGTH: 7
<212> TYPE: PRT
<213> ORGANISM: Artificial Sequence
<220> FEATURE:
<223> OTHER INFORMATION: Synthetic

<400> SEQUENCE: 115

Ser Ala Asn Asn Arg Tyr Thr
1               5

<210> SEQ ID NO 116
<211> LENGTH: 7
<212> TYPE: PRT
<213> ORGANISM: Artificial Sequence
<220> FEATURE:
<223> OTHER INFORMATION: Synthetic

<400> SEQUENCE: 116

Ser Thr Asn Asn Arg Tyr Thr
1               5

<210> SEQ ID NO 117
<211> LENGTH: 7
<212> TYPE: PRT
<213> ORGANISM: Artificial Sequence
<220> FEATURE:
<223> OTHER INFORMATION: Synthetic

<400> SEQUENCE: 117

Ser Ala Asn Arg Arg Tyr Thr
1               5

<210> SEQ ID NO 118
<211> LENGTH: 10
<212> TYPE: PRT
<213> ORGANISM: Artificial Sequence
<220> FEATURE:
<223> OTHER INFORMATION: Synthetic

<400> SEQUENCE: 118

Gly Tyr Arg Phe Thr Asp Ser Thr Met Asn
1               5                   10

<210> SEQ ID NO 119
<211> LENGTH: 10
<212> TYPE: PRT
<213> ORGANISM: Artificial Sequence
<220> FEATURE:
<223> OTHER INFORMATION: Synthetic

<400> SEQUENCE: 119

Gly Tyr Arg Phe Thr Asp Ser Thr Met Asn
1               5                   10

<210> SEQ ID NO 120
<211> LENGTH: 10
<212> TYPE: PRT
<213> ORGANISM: Artificial Sequence
<220> FEATURE:
<223> OTHER INFORMATION: Synthetic

<400> SEQUENCE: 120

Gly Tyr Arg Phe Thr Asp Ser Thr Met Asn
1               5                   10

```
<210> SEQ ID NO 121
<211> LENGTH: 10
<212> TYPE: PRT
<213> ORGANISM: Artificial Sequence
<220> FEATURE:
<223> OTHER INFORMATION: Synthetic

<400> SEQUENCE: 121

Gly Tyr Arg Phe Thr Asp Ser Thr Met Asn
1               5                   10

<210> SEQ ID NO 122
<211> LENGTH: 10
<212> TYPE: PRT
<213> ORGANISM: Artificial Sequence
<220> FEATURE:
<223> OTHER INFORMATION: Synthetic

<400> SEQUENCE: 122

Gly Tyr Arg Phe Thr Asp Ser Thr Met Asn
1               5                   10

<210> SEQ ID NO 123
<211> LENGTH: 10
<212> TYPE: PRT
<213> ORGANISM: Artificial Sequence
<220> FEATURE:
<223> OTHER INFORMATION: Synthetic

<400> SEQUENCE: 123

Gly Tyr Arg Phe Thr Asp Ser Thr Met Asn
1               5                   10

<210> SEQ ID NO 124
<211> LENGTH: 10
<212> TYPE: PRT
<213> ORGANISM: Artificial Sequence
<220> FEATURE:
<223> OTHER INFORMATION: Synthetic

<400> SEQUENCE: 124

Gly Tyr Arg Phe Thr Asp Ser Thr Met Asn
1               5                   10

<210> SEQ ID NO 125
<211> LENGTH: 17
<212> TYPE: PRT
<213> ORGANISM: Artificial Sequence
<220> FEATURE:
<223> OTHER INFORMATION: Synthetic

<400> SEQUENCE: 125

Glu Ile Trp Pro Asn Asn Gly Gly Thr Asn Tyr Asn Gln Lys Phe Lys
1               5                   10                  15

Gly

<210> SEQ ID NO 126
<211> LENGTH: 17
<212> TYPE: PRT
<213> ORGANISM: Artificial Sequence
<220> FEATURE:
<223> OTHER INFORMATION: Synthetic

<400> SEQUENCE: 126

Glu Ile Phe Pro Asn Asn Gly Gly Thr Asn Tyr Asn Gln Lys Phe Lys
1               5                   10                  15
```

Gly

<210> SEQ ID NO 127
<211> LENGTH: 17
<212> TYPE: PRT
<213> ORGANISM: Artificial Sequence
<220> FEATURE:
<223> OTHER INFORMATION: Synthetic

<400> SEQUENCE: 127

Glu Ile Phe Pro Asn Asn Gly Gly Thr Asn Tyr Asn Gln Lys Phe Lys
1               5                   10                  15

Gly

<210> SEQ ID NO 128
<211> LENGTH: 17
<212> TYPE: PRT
<213> ORGANISM: Artificial Sequence
<220> FEATURE:
<223> OTHER INFORMATION: Synthetic

<400> SEQUENCE: 128

Glu Ile Asp Pro Asn Asn Gly Gly Thr Asn Tyr Asn Gln Lys Phe Lys
1               5                   10                  15

Gly

<210> SEQ ID NO 129
<211> LENGTH: 17
<212> TYPE: PRT
<213> ORGANISM: Artificial Sequence
<220> FEATURE:
<223> OTHER INFORMATION: Synthetic

<400> SEQUENCE: 129

Glu Ile Phe Pro Asn Asn Gly Gly Thr Asn Tyr Asn Gln Lys Phe Lys
1               5                   10                  15

Gly

<210> SEQ ID NO 130
<211> LENGTH: 17
<212> TYPE: PRT
<213> ORGANISM: Artificial Sequence
<220> FEATURE:
<223> OTHER INFORMATION: Synthetic

<400> SEQUENCE: 130

Glu Ile Trp Pro Asn Asn Gly Gly Thr Asn Tyr Asn Gln Lys Phe Lys
1               5                   10                  15

Gly

<210> SEQ ID NO 131
<211> LENGTH: 17
<212> TYPE: PRT
<213> ORGANISM: Artificial Sequence
<220> FEATURE:
<223> OTHER INFORMATION: Synthetic

<400> SEQUENCE: 131

Glu Ile Trp Pro Asn Asn Gly Gly Thr Asn Tyr Asn Gln Lys Phe Lys
1               5                   10                  15

Gly

<210> SEQ ID NO 132
<211> LENGTH: 17
<212> TYPE: PRT
<213> ORGANISM: Artificial Sequence
<220> FEATURE:
<223> OTHER INFORMATION: Synthetic

<400> SEQUENCE: 132

Glu Ile Phe Pro Asn Asn Gly Gly Thr Asn Tyr Asn Gln Lys Phe Lys
1               5                   10                  15

Gly

<210> SEQ ID NO 133
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Wherein X at position 1 is R or H
<220> FEATURE:
<221> NAME/KEY: MISC_FEATURE
<222> LOCATION: (3)..(3)
<223> OTHER INFORMATION: Wherein X at position 3 is R, G, or N
<220> FEATURE:
<221> NAME/KEY: MISC_FEATURE
<222> LOCATION: (5)..(5)
<223> OTHER INFORMATION: Wherein X at position 5 is S, M, or G
<220> FEATURE:
<221> NAME/KEY: MISC_FEATURE
<222> LOCATION: (7)..(7)
<223> OTHER INFORMATION: Wherein X at position 7 is V or L
<220> FEATURE:
<221> NAME/KEY: MISC_FEATURE
<222> LOCATION: (9)..(9)
<223> OTHER INFORMATION: Wherein X at position 9 is S or I
<220> FEATURE:
<221> NAME/KEY: MISC_FEATURE
<222> LOCATION: (10)..(10)
<223> OTHER INFORMATION: Wherein X at position 10 is N or V
<220> FEATURE:
<221> NAME/KEY: MISC_FEATURE
<222> LOCATION: (13)..(13)
<223> OTHER INFORMATION: Wherein X at position 13 is T or S
<220> FEATURE:
<221> NAME/KEY: MISC_FEATURE
<222> LOCATION: (15)..(15)
<223> OTHER INFORMATION: Wherein X at position 15 is L or W

<400> SEQUENCE: 133

Xaa Ser Xaa Gln Xaa Leu Xaa His Xaa Xaa Gly Asn Xaa Tyr Xaa His
1               5                   10                  15

<210> SEQ ID NO 134
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Wherein X at position 1 is K or N
<220> FEATURE:
<221> NAME/KEY: MISC_FEATURE
<222> LOCATION: (4)..(4)
<223> OTHER INFORMATION: Wherein X at position 4 is N or R
<220> FEATURE:
<221> NAME/KEY: MISC_FEATURE
<222> LOCATION: (5)..(5)
<223> OTHER INFORMATION: Wherein X at position 5 is R or L
<220> FEATURE:

```
<221> NAME/KEY: MISC_FEATURE
<222> LOCATION: (6)..(6)
<223> OTHER INFORMATION: Wherein X at position 6 is F or R

<400> SEQUENCE: 134

Xaa Val Ser Xaa Xaa Xaa Ser
1               5

<210> SEQ ID NO 135
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Wherein X at position 2 is Q or P
<220> FEATURE:
<221> NAME/KEY: MISC_FEATURE
<222> LOCATION: (6)..(6)
<223> OTHER INFORMATION: Wherein X at position 6 is V or G
<220> FEATURE:
<221> NAME/KEY: MISC_FEATURE
<222> LOCATION: (7)..(7)
<223> OTHER INFORMATION: Wherein X at position 7 is P or S
<220> FEATURE:
<221> NAME/KEY: MISC_FEATURE
<222> LOCATION: (9)..(9)
<223> OTHER INFORMATION: Wherein X at position 9 is T or R

<400> SEQUENCE: 135

Ser Xaa Ser Thr His Xaa Xaa Pro Xaa
1               5

<210> SEQ ID NO 136
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Wherein X at position 1 is G or P
<220> FEATURE:
<221> NAME/KEY: MISC_FEATURE
<222> LOCATION: (6)..(6)
<223> OTHER INFORMATION: Wherein X at position 6 is S or I
<220> FEATURE:
<221> NAME/KEY: MISC_FEATURE
<222> LOCATION: (9)..(9)
<223> OTHER INFORMATION: Wherein X at position 9 is W or F
<220> FEATURE:
<221> NAME/KEY: MISC_FEATURE
<222> LOCATION: (10)..(10)
<223> OTHER INFORMATION: Wherein X at position 10 is N, R, or K

<400> SEQUENCE: 136

Xaa Asp Ser Ile Thr Xaa Gly Tyr Xaa Xaa
1               5                   10

<210> SEQ ID NO 137
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Wherein X at position 1 is Y or F
<220> FEATURE:
```

```
<221> NAME/KEY: MISC_FEATURE
<222> LOCATION: (5)..(5)
<223> OTHER INFORMATION: Wherein X at position 5 is S, R, or T
<220> FEATURE:
<221> NAME/KEY: MISC_FEATURE
<222> LOCATION: (7)..(7)
<223> OTHER INFORMATION: Wherein X at position 7 is S or D
<220> FEATURE:
<221> NAME/KEY: MISC_FEATURE
<222> LOCATION: (8)..(8)
<223> OTHER INFORMATION: Wherein X at position 8 is T or I
<220> FEATURE:
<221> NAME/KEY: MISC_FEATURE
<222> LOCATION: (10)..(10)
<223> OTHER INFORMATION: Wherein X at position 10 is Y or F
<220> FEATURE:
<221> NAME/KEY: MISC_FEATURE
<222> LOCATION: (11)..(11)
<223> OTHER INFORMATION: Wherein X at position 11 is N or K
<220> FEATURE:
<221> NAME/KEY: MISC_FEATURE
<222> LOCATION: (13)..(13)
<223> OTHER INFORMATION: Wherein X at position 13 is S or F
<220> FEATURE:
<221> NAME/KEY: MISC_FEATURE
<222> LOCATION: (16)..(16)
<223> OTHER INFORMATION: Wherein X at position 16 is S or N

<400> SEQUENCE: 137

Xaa Ile Ser Tyr Xaa Gly Xaa Xaa Tyr Xaa Xaa Pro Xaa Leu Lys Xaa
1               5                   10                  15

<210> SEQ ID NO 138
<211> LENGTH: 5
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Wherein X at position 1 is G, A, or E
<220> FEATURE:
<221> NAME/KEY: MISC_FEATURE
<222> LOCATION: (2)..(2)
<223> OTHER INFORMATION: Wherein X at position 2 is D or W
<220> FEATURE:
<221> NAME/KEY: MISC_FEATURE
<222> LOCATION: (3)..(3)
<223> OTHER INFORMATION: Wherein X at position 3 is G or T
<220> FEATURE:
<221> NAME/KEY: MISC_FEATURE
<222> LOCATION: (4)..(4)
<223> OTHER INFORMATION: Wherein X at position 4 is A, D, G, or Q

<400> SEQUENCE: 138

Xaa Xaa Xaa Xaa Tyr
1               5

<210> SEQ ID NO 139
<211> LENGTH: 337
<212> TYPE: DNA
<213> ORGANISM: Artificial Sequence
<220> FEATURE:
<223> OTHER INFORMATION: Synthetic

<400> SEQUENCE: 139
gatgttgtga tgacccaaac tccactctcc ctgcctgtca gtctgggaga tcaagcctcc     60
atctcttgca gatctcgtca gagccttgta cacagtaatg aaacacccta tttacattgg    120
tacctgcaga agccaggcca gtctccaaag ctcctgatct acaaagtttc caaccgattt    180
tctggggtcc cagacaggtt cagtggtagt ggatcaggga cagaattcac actcgagatc    240
```
agcagagtgg aggctgagga tctgggagtt tatttctgct ctcaaagtac acatgttcct    300
ccgacgttcg gtggaggcac caagctggaa atcaaac    337

<210> SEQ ID NO 140
<211> LENGTH: 112
<212> TYPE: PRT
<213> ORGANISM: Artificial Sequence
<220> FEATURE:
<223> OTHER INFORMATION: Synthetic

<400> SEQUENCE: 140

Asp Val Val Met Thr Gln Thr Pro Leu Ser Leu Pro Val Ser Leu Gly
1               5                   10                  15

Asp Gln Ala Ser Ile Ser Cys Arg Ser Arg Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Glu Phe Thr Leu Glu Ile
65                  70                  75                  80

Ser Arg Val Glu Ala Glu Asp Leu Gly Val Tyr Phe Cys Ser Gln Ser
                85                  90                  95

Thr His Val Pro Pro Thr Phe Gly Gly Gly Thr Lys Leu Glu Ile Lys
            100                 105                 110

<210> SEQ ID NO 141
<211> LENGTH: 339
<212> TYPE: DNA
<213> ORGANISM: Artificial Sequence
<220> FEATURE:
<223> OTHER INFORMATION: Synthetic

<400> SEQUENCE: 141
gaggtgcagc ttcaggagtc gggacctagt ctcgtgaaac cttctcagac tctgtccctc    60
acctgttctg tcactggcga ctccatcacc agtggttact ggaactggat ccggaaattc    120
ccagggaata gacttgagta catggggtac ataagctaca gtggtagcac ttactacaat    180
ccgtctctca aaagtcgaat ctccatcact cgagacacat ccaagaacca gtactaccta    240
catttgactt ctgtgactac tgaggacaca gccacatatt actgtgccca agggatggc    300 gcctactggg gccaaggcac cactctcaca gtctcctca    339

<210> SEQ ID NO 142
<211> LENGTH: 113
<212> TYPE: PRT
<213> ORGANISM: Artificial Sequence
<220> FEATURE:
<223> OTHER INFORMATION: Synthetic

<400> SEQUENCE: 142

Glu Val Gln Leu Gln Glu Ser Gly Pro Ser Leu Val Lys Pro Ser Gln
1               5                   10                  15

Thr Leu Ser Leu Thr Cys Ser Val Thr Gly Asp Ser Ile Thr Ser Gly
            20                  25                  30

Tyr Trp Asn Trp Ile Arg Lys Phe Pro Gly Asn Arg Leu Glu Tyr Met
        35                  40                  45

Gly Tyr Ile Ser Tyr Ser Gly Ser Thr Tyr Tyr Asn Pro Ser Leu Lys
    50                  55                  60

Ser Arg Ile Ser Ile Thr Arg Asp Thr Ser Lys Asn Gln Tyr Tyr Leu
65                  70                  75                  80

His Leu Thr Ser Val Thr Thr Glu Asp Thr Ala Thr Tyr Tyr Cys Ala
                85                  90                  95

Gln Gly Asp Gly Ala Tyr Trp Gly Gln Gly Thr Thr Leu Thr Val Ser
            100                 105                 110

Ser

<210> SEQ ID NO 143
<211> LENGTH: 16
<212> TYPE: PRT
<213> ORGANISM: Artificial Sequence
<220> FEATURE:
<223> OTHER INFORMATION: Synthetic

<400> SEQUENCE: 143

Arg Ser Arg Gln Ser Leu Val His Ser Asn Gly Asn Thr Tyr Leu His
1               5                   10                  15

<210> SEQ ID NO 144
<211> LENGTH: 8
<212> TYPE: PRT
<213> ORGANISM: Artificial Sequence
<220> FEATURE:
<223> OTHER INFORMATION: Synthetic

<400> SEQUENCE: 144

Arg Ser Arg Gln Ser Leu Val His
1               5

<210> SEQ ID NO 145
<211> LENGTH: 8
<212> TYPE: PRT
<213> ORGANISM: Artificial Sequence
<220> FEATURE:
<223> OTHER INFORMATION: Synthetic

<400> SEQUENCE: 145

Arg Ser Arg Gln Met Leu Val His
1               5

<210> SEQ ID NO 146
<211> LENGTH: 8
<212> TYPE: PRT
<213> ORGANISM: Artificial Sequence
<220> FEATURE:
<223> OTHER INFORMATION: Synthetic

<400> SEQUENCE: 146

Arg Ser Arg Gln Ser Leu Leu His
1               5

<210> SEQ ID NO 147
<211> LENGTH: 8
<212> TYPE: PRT
<213> ORGANISM: Artificial Sequence
<220> FEATURE:
<223> OTHER INFORMATION: Synthetic

<400> SEQUENCE: 147

His Ser Arg Gln Ser Leu Val His
1               5

<210> SEQ ID NO 148

```
<211> LENGTH: 8
<212> TYPE: PRT
<213> ORGANISM: Artificial Sequence
<220> FEATURE:
<223> OTHER INFORMATION: Synthetic

<400> SEQUENCE: 148

Arg Ser Gly Gln Ser Leu Val His
1               5

<210> SEQ ID NO 149
<211> LENGTH: 8
<212> TYPE: PRT
<213> ORGANISM: Artificial Sequence
<220> FEATURE:
<223> OTHER INFORMATION: Synthetic

<400> SEQUENCE: 149

Arg Ser Asn Gln Ser Leu Val His
1               5

<210> SEQ ID NO 150
<211> LENGTH: 8
<212> TYPE: PRT
<213> ORGANISM: Artificial Sequence
<220> FEATURE:
<223> OTHER INFORMATION: Synthetic

<400> SEQUENCE: 150

Ser Asn Gly Asn Thr Tyr Leu His
1               5

<210> SEQ ID NO 151
<211> LENGTH: 8
<212> TYPE: PRT
<213> ORGANISM: Artificial Sequence
<220> FEATURE:
<223> OTHER INFORMATION: Synthetic

<400> SEQUENCE: 151

Ser Asn Gly Asn Ser Tyr Leu His
1               5

<210> SEQ ID NO 152
<211> LENGTH: 8
<212> TYPE: PRT
<213> ORGANISM: Artificial Sequence
<220> FEATURE:
<223> OTHER INFORMATION: Synthetic

<400> SEQUENCE: 152

Ile Asn Gly Asn Thr Tyr Leu His
1               5

<210> SEQ ID NO 153
<211> LENGTH: 8
<212> TYPE: PRT
<213> ORGANISM: Artificial Sequence
<220> FEATURE:
<223> OTHER INFORMATION: Synthetic

<400> SEQUENCE: 153

Ser Asn Gly Asn Thr Tyr Trp His
1               5

<210> SEQ ID NO 154
<211> LENGTH: 8
```

```
<212> TYPE: PRT
<213> ORGANISM: Artificial Sequence
<220> FEATURE:
<223> OTHER INFORMATION: Synthetic

<400> SEQUENCE: 154

Ser Val Gly Asn Thr Tyr Leu His
1               5

<210> SEQ ID NO 155
<211> LENGTH: 7
<212> TYPE: PRT
<213> ORGANISM: Artificial Sequence
<220> FEATURE:
<223> OTHER INFORMATION: Synthetic

<400> SEQUENCE: 155

Lys Val Ser Asn Arg Phe Ser
1               5

<210> SEQ ID NO 156
<211> LENGTH: 7
<212> TYPE: PRT
<213> ORGANISM: Artificial Sequence
<220> FEATURE:
<223> OTHER INFORMATION: Synthetic

<400> SEQUENCE: 156

Asn Val Ser Asn Arg Phe Ser
1               5

<210> SEQ ID NO 157
<211> LENGTH: 7
<212> TYPE: PRT
<213> ORGANISM: Artificial Sequence
<220> FEATURE:
<223> OTHER INFORMATION: Synthetic

<400> SEQUENCE: 157

Lys Val Ser Arg Arg Phe Ser
1               5

<210> SEQ ID NO 158
<211> LENGTH: 7
<212> TYPE: PRT
<213> ORGANISM: Artificial Sequence
<220> FEATURE:
<223> OTHER INFORMATION: Synthetic

<400> SEQUENCE: 158

Lys Val Ser Asn Arg Arg Ser
1               5

<210> SEQ ID NO 159
<211> LENGTH: 7
<212> TYPE: PRT
<213> ORGANISM: Artificial Sequence
<220> FEATURE:
<223> OTHER INFORMATION: Synthetic

<400> SEQUENCE: 159

Lys Val Ser Asn Leu Phe Ser
1               5

<210> SEQ ID NO 160
<211> LENGTH: 9
<212> TYPE: PRT
```

```
<213> ORGANISM: Artificial Sequence
<220> FEATURE:
<223> OTHER INFORMATION: Synthetic

<400> SEQUENCE: 160

Ser Gln Ser Thr His Val Pro Pro Thr
1               5

<210> SEQ ID NO 161
<211> LENGTH: 9
<212> TYPE: PRT
<213> ORGANISM: Artificial Sequence
<220> FEATURE:
<223> OTHER INFORMATION: Synthetic

<400> SEQUENCE: 161

Ser Gln Ser Thr His Val Ser Pro Thr
1               5

<210> SEQ ID NO 162
<211> LENGTH: 9
<212> TYPE: PRT
<213> ORGANISM: Artificial Sequence
<220> FEATURE:
<223> OTHER INFORMATION: Synthetic

<400> SEQUENCE: 162

Ser Gln Ser Thr His Val Pro Pro Arg
1               5

<210> SEQ ID NO 163
<211> LENGTH: 9
<212> TYPE: PRT
<213> ORGANISM: Artificial Sequence
<220> FEATURE:
<223> OTHER INFORMATION: Synthetic

<400> SEQUENCE: 163

Ser Gln Ser Thr His Gly Pro Pro Thr
1               5

<210> SEQ ID NO 164
<211> LENGTH: 9
<212> TYPE: PRT
<213> ORGANISM: Artificial Sequence
<220> FEATURE:
<223> OTHER INFORMATION: Synthetic

<400> SEQUENCE: 164

Ser Pro Ser Thr His Val Pro Pro Thr
1               5

<210> SEQ ID NO 165
<211> LENGTH: 9
<212> TYPE: PRT
<213> ORGANISM: Artificial Sequence
<220> FEATURE:
<223> OTHER INFORMATION: Synthetic

<400> SEQUENCE: 165

Ser Gln Ser Thr His Val Ser Pro Thr
1               5

<210> SEQ ID NO 166
<211> LENGTH: 10
<212> TYPE: PRT
<213> ORGANISM: Artificial Sequence
```

```
<220> FEATURE:
<223> OTHER INFORMATION: Synthetic

<400> SEQUENCE: 166

Gly Asp Ser Ile Thr Ser Gly Tyr Trp Asn
1               5                   10

<210> SEQ ID NO 167
<211> LENGTH: 10
<212> TYPE: PRT
<213> ORGANISM: Artificial Sequence
<220> FEATURE:
<223> OTHER INFORMATION: Synthetic

<400> SEQUENCE: 167

Pro Asp Ser Ile Thr Ser Gly Tyr Trp Asn
1               5                   10

<210> SEQ ID NO 168
<211> LENGTH: 10
<212> TYPE: PRT
<213> ORGANISM: Artificial Sequence
<220> FEATURE:
<223> OTHER INFORMATION: Synthetic

<400> SEQUENCE: 168

Gly Asp Ser Ile Thr Ser Gly Tyr Trp Arg
1               5                   10

<210> SEQ ID NO 169
<211> LENGTH: 10
<212> TYPE: PRT
<213> ORGANISM: Artificial Sequence
<220> FEATURE:
<223> OTHER INFORMATION: Synthetic

<400> SEQUENCE: 169

Gly Asp Ser Ile Thr Ser Gly Tyr Phe Asn
1               5                   10

<210> SEQ ID NO 170
<211> LENGTH: 10
<212> TYPE: PRT
<213> ORGANISM: Artificial Sequence
<220> FEATURE:
<223> OTHER INFORMATION: Synthetic

<400> SEQUENCE: 170

Gly Asp Ser Ile Thr Ser Gly Tyr Trp Lys
1               5                   10

<210> SEQ ID NO 171
<211> LENGTH: 10
<212> TYPE: PRT
<213> ORGANISM: Artificial Sequence
<220> FEATURE:
<223> OTHER INFORMATION: Synthetic

<400> SEQUENCE: 171

Gly Asp Ser Ile Thr Ile Gly Tyr Trp Asn
1               5                   10

<210> SEQ ID NO 172
<211> LENGTH: 16
<212> TYPE: PRT
<213> ORGANISM: Artificial Sequence
<220> FEATURE:
```

```
<223> OTHER INFORMATION: Synthetic

<400> SEQUENCE: 172

Tyr Ile Ser Tyr Ser Gly Ser Thr Tyr Tyr Asn Pro Ser Leu Lys Ser
1               5                   10                  15

<210> SEQ ID NO 173
<211> LENGTH: 8
<212> TYPE: PRT
<213> ORGANISM: Artificial Sequence
<220> FEATURE:
<223> OTHER INFORMATION: Synthetic

<400> SEQUENCE: 173

Tyr Ile Ser Tyr Ser Gly Ser Thr
1               5

<210> SEQ ID NO 174
<211> LENGTH: 8
<212> TYPE: PRT
<213> ORGANISM: Artificial Sequence
<220> FEATURE:
<223> OTHER INFORMATION: Synthetic

<400> SEQUENCE: 174

Phe Ile Ser Tyr Ser Gly Ser Thr
1               5

<210> SEQ ID NO 175
<211> LENGTH: 8
<212> TYPE: PRT
<213> ORGANISM: Artificial Sequence
<220> FEATURE:
<223> OTHER INFORMATION: Synthetic

<400> SEQUENCE: 175

Tyr Ile Ser Tyr Arg Gly Ser Thr
1               5

<210> SEQ ID NO 176
<211> LENGTH: 8
<212> TYPE: PRT
<213> ORGANISM: Artificial Sequence
<220> FEATURE:
<223> OTHER INFORMATION: Synthetic

<400> SEQUENCE: 176

Tyr Ile Ser Tyr Ser Gly Ser Ile
1               5

<210> SEQ ID NO 177
<211> LENGTH: 8
<212> TYPE: PRT
<213> ORGANISM: Artificial Sequence
<220> FEATURE:
<223> OTHER INFORMATION: Synthetic

<400> SEQUENCE: 177

Tyr Ile Ser Tyr Ser Gly Asp Thr
1               5

<210> SEQ ID NO 178
<211> LENGTH: 8
<212> TYPE: PRT
<213> ORGANISM: Artificial Sequence
<220> FEATURE:
<223> OTHER INFORMATION: Synthetic
```

<400> SEQUENCE: 178

Tyr Ile Ser Tyr Thr Gly Ser Thr
1               5

<210> SEQ ID NO 179
<211> LENGTH: 8
<212> TYPE: PRT
<213> ORGANISM: Artificial Sequence
<220> FEATURE:
<223> OTHER INFORMATION: Synthetic

<400> SEQUENCE: 179

Tyr Tyr Asn Pro Ser Leu Lys Ser
1               5

<210> SEQ ID NO 180
<211> LENGTH: 8
<212> TYPE: PRT
<213> ORGANISM: Artificial Sequence
<220> FEATURE:
<223> OTHER INFORMATION: Synthetic

<400> SEQUENCE: 180

Tyr Tyr Lys Pro Ser Leu Lys Ser
1               5

<210> SEQ ID NO 181
<211> LENGTH: 8
<212> TYPE: PRT
<213> ORGANISM: Artificial Sequence
<220> FEATURE:
<223> OTHER INFORMATION: Synthetic

<400> SEQUENCE: 181

Tyr Tyr Asn Pro Phe Leu Lys Ser
1               5

<210> SEQ ID NO 182
<211> LENGTH: 8
<212> TYPE: PRT
<213> ORGANISM: Artificial Sequence
<220> FEATURE:
<223> OTHER INFORMATION: Synthetic

<400> SEQUENCE: 182

Tyr Phe Asn Pro Ser Leu Lys Ser
1               5

<210> SEQ ID NO 183
<211> LENGTH: 8
<212> TYPE: PRT
<213> ORGANISM: Artificial Sequence
<220> FEATURE:
<223> OTHER INFORMATION: Synthetic

<400> SEQUENCE: 183

Tyr Tyr Asn Pro Ser Leu Lys Asn
1               5

<210> SEQ ID NO 184
<211> LENGTH: 5
<212> TYPE: PRT
<213> ORGANISM: Artificial Sequence
<220> FEATURE:
<223> OTHER INFORMATION: Synthetic

```
<400> SEQUENCE: 184

Gly Asp Gly Ala Tyr
1               5

<210> SEQ ID NO 185
<211> LENGTH: 5
<212> TYPE: PRT
<213> ORGANISM: Artificial Sequence
<220> FEATURE:
<223> OTHER INFORMATION: Synthetic

<400> SEQUENCE: 185

Gly Asp Gly Asp Tyr
1               5

<210> SEQ ID NO 186
<211> LENGTH: 5
<212> TYPE: PRT
<213> ORGANISM: Artificial Sequence
<220> FEATURE:
<223> OTHER INFORMATION: Synthetic

<400> SEQUENCE: 186

Gly Asp Thr Ala Tyr
1               5

<210> SEQ ID NO 187
<211> LENGTH: 5
<212> TYPE: PRT
<213> ORGANISM: Artificial Sequence
<220> FEATURE:
<223> OTHER INFORMATION: Synthetic

<400> SEQUENCE: 187

Ala Asp Gly Ala Tyr
1               5

<210> SEQ ID NO 188
<211> LENGTH: 5
<212> TYPE: PRT
<213> ORGANISM: Artificial Sequence
<220> FEATURE:
<223> OTHER INFORMATION: Synthetic

<400> SEQUENCE: 188

Gly Trp Gly Ala Tyr
1               5

<210> SEQ ID NO 189
<211> LENGTH: 5
<212> TYPE: PRT
<213> ORGANISM: Artificial Sequence
<220> FEATURE:
<223> OTHER INFORMATION: Synthetic

<400> SEQUENCE: 189

Glu Asp Gly Ala Tyr
1               5

<210> SEQ ID NO 190
<211> LENGTH: 107
<212> TYPE: PRT
<213> ORGANISM: Artificial Sequence
<220> FEATURE:
<223> OTHER INFORMATION: Synthetic

<400> SEQUENCE: 190
```

```
Asp Ile Val Met Thr Gln Ser Gln Lys Phe Met Ser Ile Thr Leu Gly
1               5                   10                  15

Glu Arg Val Ser Ile Thr Cys Lys Pro Ser Gln Lys Val Gly Ser Arg
            20                  25                  30

Val Thr Trp Trp Gln Gln Lys Pro Gly Gln Ser Pro Lys Leu Leu Ile
        35                  40                  45

Tyr Ser Ala Ile Asn Arg Tyr Thr Gly Val Pro Asp Arg Phe Thr Gly
50                  55                  60

Ser Gly Ser Gly Thr Asp Phe Thr Leu Thr Ile Ser Asn Val Gln Ser
65                  70                  75                  80

Glu Asp Leu Ala Asp Tyr Phe Cys Gln Gln Tyr Ser Ser Tyr Pro Tyr
            85                  90                  95

Thr Phe Gly Gly Gly Thr Lys Leu Glu Ile Lys
            100                 105
```

<210> SEQ ID NO 191
<211> LENGTH: 107
<212> TYPE: PRT
<213> ORGANISM: Artificial Sequence
<220> FEATURE:
<223> OTHER INFORMATION: Synthetic

<400> SEQUENCE: 191

```
Asp Ile Val Met Thr Gln Ser Gln Lys Phe Met Ser Ile Thr Leu Gly
1               5                   10                  15

Glu Arg Val Ser Ile Thr Cys Lys Pro Ser Gln Arg Val Gly Ser Arg
            20                  25                  30

Val Thr Trp Trp Gln Gln Lys Pro Gly Gln Ser Pro Lys Leu Leu Ile
        35                  40                  45

Tyr Ser Thr Ile Asn Arg Tyr Thr Gly Val Pro Asp Arg Phe Thr Gly
50                  55                  60

Ser Gly Ser Gly Thr Asp Phe Thr Leu Thr Ile Ser Asn Val Gln Ser
65                  70                  75                  80

Glu Asp Leu Ala Asp Tyr Phe Cys Gln Gln Tyr Ser Ser Tyr Pro Tyr
            85                  90                  95

Thr Phe Gly Gly Gly Thr Lys Leu Glu Ile Lys
            100                 105
```

<210> SEQ ID NO 192
<211> LENGTH: 107
<212> TYPE: PRT
<213> ORGANISM: Artificial Sequence
<220> FEATURE:
<223> OTHER INFORMATION: Synthetic

<400> SEQUENCE: 192

```
Asp Ile Val Met Thr Gln Ser Gln Lys Phe Met Ser Ile Thr Leu Gly
1               5                   10                  15

Glu Arg Val Ser Ile Thr Cys Lys Pro Ser Gln Lys Val Gly Ser Ala
            20                  25                  30

Val Thr Trp Trp Gln Gln Lys Pro Gly Gln Ser Pro Lys Leu Leu Ile
        35                  40                  45

Tyr Ser Thr Asn Asn Arg Tyr Thr Gly Val Pro Asp Arg Phe Thr Gly
50                  55                  60

Ser Gly Ser Gly Thr Asp Phe Thr Leu Thr Ile Ser Asn Val Gln Ser
65                  70                  75                  80

Glu Asp Leu Ala Asp Tyr Phe Cys Gln Gln Tyr Ser Ser Tyr Pro Tyr
```

```
                    85                  90                  95

Thr Phe Gly Gly Gly Thr Lys Leu Glu Ile Lys
                100                 105

<210> SEQ ID NO 193
<211> LENGTH: 107
<212> TYPE: PRT
<213> ORGANISM: Artificial Sequence
<220> FEATURE:
<223> OTHER INFORMATION: Synthetic

<400> SEQUENCE: 193

Asp Ile Val Met Thr Gln Ser Gln Lys Phe Met Ser Ile Thr Leu Gly
1               5                   10                  15

Glu Arg Val Ser Ile Thr Cys Lys Pro Ser Gln Asn Val Gly Ser Ala
            20                  25                  30

Val Thr Trp Trp Gln Gln Lys Pro Gly Gln Ser Pro Lys Leu Leu Ile
        35                  40                  45

Tyr Ser Ala Ser Asn Arg Tyr Thr Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Asp Tyr Phe Cys Gln Gln Tyr Ser Ser Tyr Pro Tyr
                85                  90                  95

Thr Phe Gly Gly Gly Thr Lys Leu Glu Ile Lys
                100                 105

<210> SEQ ID NO 194
<211> LENGTH: 107
<212> TYPE: PRT
<213> ORGANISM: Artificial Sequence
<220> FEATURE:
<223> OTHER INFORMATION: Synthetic

<400> SEQUENCE: 194

Asp Ile Val Met Thr Gln Ser Gln Lys Phe Met Ser Ile Thr Leu Gly
1               5                   10                  15

Glu Arg Val Ser Ile Thr Cys Lys Pro Ser Gln Lys Val Gly Ser Ala
            20                  25                  30

Val Thr Trp Trp Gln Gln Lys Pro Gly Gln Ser Pro Lys Leu Leu Ile
        35                  40                  45

Tyr Ser Thr Ile Arg Arg Tyr Thr Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Asp Tyr Phe Cys Gln Gln Tyr Ser Ser Tyr Pro Tyr
                85                  90                  95

Thr Phe Gly Gly Gly Thr Lys Leu Glu Ile Lys
                100                 105

<210> SEQ ID NO 195
<211> LENGTH: 107
<212> TYPE: PRT
<213> ORGANISM: Artificial Sequence
<220> FEATURE:
<223> OTHER INFORMATION: Synthetic

<400> SEQUENCE: 195

Asp Ile Val Met Thr Gln Ser Gln Lys Phe Met Ser Ile Thr Leu Gly
1               5                   10                  15
```

Glu Arg Val Ser Ile Thr Cys Lys Pro Ser Gln Lys Val Gly Ser Arg
            20                  25                  30

Val Thr Trp Trp Gln Gln Lys Pro Gly Gln Ser Pro Lys Leu Leu Ile
        35                  40                  45

Tyr Ser Ala Asn Asn Arg Tyr Thr Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Asp Tyr Phe Cys Gln Gln Tyr Ser Ser Tyr Pro Tyr
                85                  90                  95

Thr Phe Gly Gly Gly Thr Lys Leu Glu Ile Lys
            100                 105

<210> SEQ ID NO 196
<211> LENGTH: 107
<212> TYPE: PRT
<213> ORGANISM: Artificial Sequence
<220> FEATURE:
<223> OTHER INFORMATION: Synthetic

<400> SEQUENCE: 196

Asp Ile Val Met Thr Gln Ser Gln Lys Phe Met Ser Ile Thr Leu Gly
1               5                   10                  15

Glu Arg Val Ser Ile Thr Cys Lys Pro Ser Gln Lys Val Gly Ser Arg
            20                  25                  30

Val Thr Trp Trp Gln Gln Lys Pro Gly Gln Ser Pro Lys Leu Leu Ile
        35                  40                  45

Tyr Ser Thr Asn Asn Arg Tyr Thr Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Asp Tyr Phe Cys Gln Gln Tyr Ser Ser Tyr Pro Tyr
                85                  90                  95

Thr Phe Gly Gly Gly Thr Lys Leu Glu Ile Lys
            100                 105

<210> SEQ ID NO 197
<211> LENGTH: 107
<212> TYPE: PRT
<213> ORGANISM: Artificial Sequence
<220> FEATURE:
<223> OTHER INFORMATION: Synthetic

<400> SEQUENCE: 197

Asp Ile Val Met Thr Gln Ser Gln Lys Phe Met Ser Ile Thr Leu Gly
1               5                   10                  15

Glu Arg Val Ser Ile Thr Cys Lys Pro Ser Gln Lys Val Gly Ser Ala
            20                  25                  30

Val Thr Trp Trp Gln Gln Lys Pro Gly Gln Ser Pro Lys Leu Leu Ile
        35                  40                  45

Tyr Ser Ala Asn Arg Arg Tyr Thr Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Asp Tyr Phe Cys Gln Gln Tyr Ser Ser Tyr Pro Tyr
                85                  90                  95

Thr Phe Gly Gly Gly Thr Lys Leu Glu Ile Lys

-continued

<210> SEQ ID NO 198
<211> LENGTH: 111
<212> TYPE: PRT
<213> ORGANISM: Artificial Sequence
<220> FEATURE:
<223> OTHER INFORMATION: Synthetic

<400> SEQUENCE: 198

Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Arg Phe Thr Asp Ser
            20                  25                  30

Thr Met Asn Trp Val Lys Gln Ser His Gly Lys Ser Leu Glu Trp Ile
        35                  40                  45

Gly Glu Ile Trp Pro Asn Asn Gly Gly Thr Asn Tyr Asn Gln Lys Phe
    50                  55                  60

Lys Gly Lys Ala Thr Leu Thr Val Asp Lys Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Arg Gly Val Trp Gly Gln Gly Thr Thr Leu Thr Val Ser Ser
            100                 105                 110

<210> SEQ ID NO 199
<211> LENGTH: 111
<212> TYPE: PRT
<213> ORGANISM: Artificial Sequence
<220> FEATURE:
<223> OTHER INFORMATION: Synthetic

<400> SEQUENCE: 199

Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Arg Phe Thr Asp Ser
            20                  25                  30

Thr Met Asn Trp Val Lys Gln Ser His Gly Lys Ser Leu Glu Trp Ile
        35                  40                  45

Gly Glu Ile Phe Pro Asn Asn Gly Gly Thr Asn Tyr Asn Gln Lys Phe
    50                  55                  60

Lys Gly Lys Ala Thr Leu Thr Val Asp Lys Ser Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Arg Gly Val Trp Gly Gln Gly Thr Thr Leu Thr Val Ser Ser
            100                 105                 110

<210> SEQ ID NO 200
<211> LENGTH: 111
<212> TYPE: PRT
<213> ORGANISM: Artificial Sequence
<220> FEATURE:
<223> OTHER INFORMATION: Synthetic

<400> SEQUENCE: 200

Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Arg Phe Thr Asp Ser
            20                  25                  30

```
Thr Met Asn Trp Val Lys Gln Ser His Gly Lys Ser Leu Glu Trp Ile
        35                  40                  45

Gly Glu Ile Phe Pro Asn Asn Gly Gly Thr Asn Tyr Asn Gln Lys Phe
50                  55                  60

Lys Gly Lys Ala Thr Leu Thr Val Asp Lys Ser Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Arg Gly Val Trp Gly Gln Gly Thr Thr Leu Thr Val Ser Ser
                100                 105                 110

<210> SEQ ID NO 201
<211> LENGTH: 111
<212> TYPE: PRT
<213> ORGANISM: Artificial Sequence
<220> FEATURE:
<223> OTHER INFORMATION: Synthetic

<400> SEQUENCE: 201

Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Thr Phe Thr Asp Ser
                20                  25                  30

Thr Met Asn Trp Val Lys Gln Ser His Gly Lys Ser Leu Glu Trp Ile
        35                  40                  45

Gly Glu Ile Asp Pro Asn Asn Gly Gly Thr Asn Tyr Asn Gln Lys Phe
50                  55                  60

Lys Gly Lys Ala Thr Leu Thr Val Asp Lys Ser Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Arg Gly Val Trp Gly Gln Gly Thr Thr Leu Thr Val Ser Ser
                100                 105                 110

<210> SEQ ID NO 202
<211> LENGTH: 111
<212> TYPE: PRT
<213> ORGANISM: Artificial Sequence
<220> FEATURE:
<223> OTHER INFORMATION: Synthetic

<400> SEQUENCE: 202

Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Arg Phe Thr Asp Ser
                20                  25                  30

Thr Met Asn Trp Val Lys Gln Ser His Gly Lys Ser Leu Glu Trp Ile
        35                  40                  45

Gly Glu Ile Phe Pro Asn Asn Gly Gly Thr Asn Tyr Asn Gln Lys Phe
50                  55                  60

Lys Gly Lys Ala Thr Leu Thr Val Asp Lys Ser Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Arg Gly Val Trp Gly Gln Gly Thr Thr Leu Thr Val Ser Ser
                100                 105                 110
```

```
<210> SEQ ID NO 203
<211> LENGTH: 111
<212> TYPE: PRT
<213> ORGANISM: Artificial Sequence
<220> FEATURE:
<223> OTHER INFORMATION: Synthetic

<400> SEQUENCE: 203

Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Arg Phe Thr Asp Ser
                20                  25                  30

Thr Met Asn Trp Val Lys Gln Ser His Gly Lys Ser Leu Glu Trp Ile
            35                  40                  45

Gly Glu Ile Trp Pro Asn Asn Gly Gly Thr Asn Tyr Asn Gln Lys Phe
        50                  55                  60

Lys Gly Lys Ala Thr Leu Thr Val Asp Lys Ser Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Arg Gly Val Trp Gly Gln Gly Thr Thr Leu Thr Val Ser Ser
            100                 105                 110

<210> SEQ ID NO 204
<211> LENGTH: 111
<212> TYPE: PRT
<213> ORGANISM: Artificial Sequence
<220> FEATURE:
<223> OTHER INFORMATION: Synthetic

<400> SEQUENCE: 204

Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Arg Phe Thr Asp Ser
                20                  25                  30

Thr Met Asn Trp Val Lys Gln Ser His Gly Lys Ser Leu Glu Trp Ile
            35                  40                  45

Gly Glu Ile Trp Pro Asn Asn Gly Gly Thr Asn Tyr Asn Gln Lys Phe
        50                  55                  60

Lys Gly Lys Ala Thr Leu Thr Val Asp Lys Ser Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Arg Gly Val Trp Gly Gln Gly Thr Thr Leu Thr Val Ser Ser
            100                 105                 110

<210> SEQ ID NO 205
<211> LENGTH: 111
<212> TYPE: PRT
<213> ORGANISM: Artificial Sequence
<220> FEATURE:
<223> OTHER INFORMATION: Synthetic

<400> SEQUENCE: 205

Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Arg Phe Thr Asp Ser
                20                  25                  30

Thr Met Asn Trp Val Lys Gln Ser His Gly Lys Ser Leu Glu Trp Ile
            35                  40                  45
```

Gly Glu Ile Phe Pro Asn Asn Gly Gly Thr Asn Tyr Asn Gln Lys Phe
            50                  55                  60

Lys Gly Lys Ala Thr Leu Thr Val Asp Lys Ser Ser Thr Ala Tyr
 65                  70                  75                  80

Met Glu Leu Arg Ser Leu Thr Ser Glu Asp Ser Ala Val Tyr Tyr Cys
                 85                  90                  95

Ala Arg Gly Val Trp Gly Gln Gly Thr Thr Leu Thr Val Ser Ser
                100                 105                 110

<210> SEQ ID NO 206
<211> LENGTH: 112
<212> TYPE: PRT
<213> ORGANISM: Artificial Sequence
<220> FEATURE:
<223> OTHER INFORMATION: Synthetic

<400> SEQUENCE: 206

Asp Val Val Met Thr Gln Thr Pro Leu Ser Leu Pro Val Ser Leu Gly
  1               5                  10                  15

Asp Gln Ala Ser Ile Ser Cys Arg Ser Arg Gln Met Leu Val His Ser
                 20                  25                  30

Asn Gly Asn Thr Tyr Leu His Trp Tyr Leu Gln Lys Pro Gly Gln Ser
             35                  40                  45

Pro Lys Leu Leu Ile Tyr Lys Val Ser Asn Arg Phe Ser Gly Val Pro
 50                  55                  60

Asp Arg Phe Ser Gly Ser Gly Ser Gly Thr Glu Phe Thr Leu Glu Ile
 65                  70                  75                  80

Ser Arg Val Glu Ala Glu Asp Leu Gly Val Tyr Phe Cys Ser Gln Ser
                 85                  90                  95

Thr His Val Pro Pro Thr Phe Gly Gly Gly Thr Lys Leu Glu Ile Lys
                100                 105                 110

<210> SEQ ID NO 207
<211> LENGTH: 112
<212> TYPE: PRT
<213> ORGANISM: Artificial Sequence
<220> FEATURE:
<223> OTHER INFORMATION: Synthetic

<400> SEQUENCE: 207

Asp Val Val Met Thr Gln Thr Pro Leu Ser Leu Pro Val Ser Leu Gly
  1               5                  10                  15

Asp Gln Ala Ser Ile Ser Cys Arg Ser Arg Gln Ser Leu Leu His Ser
                 20                  25                  30

Asn Gly Asn Thr Tyr Leu His Trp Tyr Leu Gln Lys Pro Gly Gln Ser
             35                  40                  45

Pro Lys Leu Leu Ile Tyr Lys Val Ser Asn Arg Phe Ser Gly Val Pro
 50                  55                  60

Asp Arg Phe Ser Gly Ser Gly Ser Gly Thr Glu Phe Thr Leu Glu Ile
 65                  70                  75                  80

Ser Arg Val Glu Ala Glu Asp Leu Gly Val Tyr Phe Cys Ser Gln Ser
                 85                  90                  95

Thr His Val Pro Pro Thr Phe Gly Gly Gly Thr Lys Leu Glu Ile Lys
                100                 105                 110

<210> SEQ ID NO 208
<211> LENGTH: 112
<212> TYPE: PRT

```
<213> ORGANISM: Artificial Sequence
<220> FEATURE:
<223> OTHER INFORMATION: Synthetic

<400> SEQUENCE: 208

Asp Val Val Met Thr Gln Thr Pro Leu Ser Leu Pro Val Ser Leu Gly
1               5                   10                  15

Asp Gln Ala Ser Ile Ser Cys His Ser Arg Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Glu Phe Thr Leu Glu Ile
65                  70                  75                  80

Ser Arg Val Glu Ala Glu Asp Leu Gly Val Tyr Phe Cys Ser Gln Ser
                85                  90                  95

Thr His Val Pro Pro Thr Phe Gly Gly Gly Thr Lys Leu Glu Ile Lys
            100                 105                 110

<210> SEQ ID NO 209
<211> LENGTH: 112
<212> TYPE: PRT
<213> ORGANISM: Artificial Sequence
<220> FEATURE:
<223> OTHER INFORMATION: Synthetic

<400> SEQUENCE: 209

Asp Val Val Met Thr Gln Thr Pro Leu Ser Leu Pro Val Ser Leu Gly
1               5                   10                  15

Asp Gln Ala Ser Ile Ser Cys Arg Ser Gly Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Glu Phe Thr Leu Glu Ile
65                  70                  75                  80

Ser Arg Val Glu Ala Glu Asp Leu Gly Val Tyr Phe Cys Ser Gln Ser
                85                  90                  95

Thr His Val Pro Pro Thr Phe Gly Gly Gly Thr Lys Leu Glu Ile Lys
            100                 105                 110

<210> SEQ ID NO 210
<211> LENGTH: 112
<212> TYPE: PRT
<213> ORGANISM: Artificial Sequence
<220> FEATURE:
<223> OTHER INFORMATION: Synthetic

<400> SEQUENCE: 210

Asp Val Val Met Thr Gln Thr Pro Leu Ser Leu Pro Val Ser Leu Gly
1               5                   10                  15

Asp Gln Ala Ser Ile Ser Cys Arg Ser Asn Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60
```

```
Asp Arg Phe Ser Gly Ser Gly Ser Gly Thr Glu Phe Thr Leu Glu Ile
 65                  70                  75                  80

Ser Arg Val Glu Ala Glu Asp Leu Gly Val Tyr Phe Cys Ser Gln Ser
                 85                  90                  95

Thr His Val Pro Pro Thr Phe Gly Gly Gly Thr Lys Leu Glu Ile Lys
            100                 105                 110
```

<210> SEQ ID NO 211
<211> LENGTH: 109
<212> TYPE: PRT
<213> ORGANISM: Artificial Sequence
<220> FEATURE:
<223> OTHER INFORMATION: Synthetic

<400> SEQUENCE: 211

```
Asp Val Val Met Thr Gln Thr Pro Leu Ser Leu Pro Val Ser Leu Gly
 1               5                  10                  15

Asp Gln Ala Ser Ile Arg Ser Arg Gln Ser Val His Ser Asn Gly Asn
             20                  25                  30

Ser Tyr Leu His Trp Tyr Leu Gln Lys Pro Gly Gln Ser Pro Lys Leu
         35                  40                  45

Leu Ile Tyr Lys Val Ser Asn Arg Phe Ser Gly Val Pro Asp Arg Phe
     50                  55                  60

Ser Gly Ser Gly Ser Gly Thr Glu Phe Thr Leu Glu Ile Ser Arg Val
 65                  70                  75                  80

Glu Ala Glu Asp Leu Gly Val Tyr Phe Cys Ser Gln Ser Thr His Val
                 85                  90                  95

Pro Pro Thr Phe Gly Gly Gly Thr Lys Leu Glu Ile Lys
            100                 105
```

<210> SEQ ID NO 212
<211> LENGTH: 112
<212> TYPE: PRT
<213> ORGANISM: Artificial Sequence
<220> FEATURE:
<223> OTHER INFORMATION: Synthetic

<400> SEQUENCE: 212

```
Asp Val Val Met Thr Gln Thr Pro Leu Ser Leu Pro Val Ser Leu Gly
 1               5                  10                  15

Asp Gln Ala Ser Ile Ser Cys Arg Ser Arg Gln Ser Leu Val His Ser
             20                  25                  30

Asn Gly Asn Thr Tyr Leu His Trp Tyr Leu Gln Lys Pro Gly Gln Ser
         35                  40                  45

Pro Lys Leu Leu Ile Tyr Lys Val Ser Asn Arg Phe Ser Gly Val Pro
     50                  55                  60

Asp Arg Phe Ser Gly Ser Gly Ser Gly Thr Glu Phe Thr Leu Glu Ile
 65                  70                  75                  80

Ser Arg Val Glu Ala Glu Asp Leu Gly Val Tyr Phe Cys Ser Gln Ser
                 85                  90                  95

Thr His Val Pro Pro Thr Phe Gly Gly Gly Thr Lys Leu Glu Ile Lys
            100                 105                 110
```

<210> SEQ ID NO 213
<211> LENGTH: 112
<212> TYPE: PRT
<213> ORGANISM: Artificial Sequence
<220> FEATURE:
<223> OTHER INFORMATION: Synthetic

<400> SEQUENCE: 213

Asp Val Val Met Thr Gln Thr Pro Leu Ser Leu Pro Val Ser Leu Gly
1               5                   10                  15

Asp Gln Ala Ser Ile Ser Cys Arg Ser Arg Gln Ser Leu Val His Ile
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Glu Phe Thr Leu Glu Ile
65                  70                  75                  80

Ser Arg Val Glu Ala Glu Asp Leu Gly Val Tyr Phe Cys Ser Gln Ser
                85                  90                  95

Thr His Val Pro Pro Thr Phe Gly Gly Gly Thr Lys Leu Glu Ile Lys
            100                 105                 110

<210> SEQ ID NO 214
<211> LENGTH: 112
<212> TYPE: PRT
<213> ORGANISM: Artificial Sequence
<220> FEATURE:
<223> OTHER INFORMATION: Synthetic

<400> SEQUENCE: 214

Asp Val Val Met Thr Gln Thr Pro Leu Ser Leu Pro Val Ser Leu Gly
1               5                   10                  15

Asp Gln Ala Ser Ile Ser Cys Arg Ser Arg Gln Ser Leu Val His Ser
            20                  25                  30

Asn Gly Asn Thr Tyr Trp His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Glu Phe Thr Leu Glu Ile
65                  70                  75                  80

Ser Arg Val Glu Ala Glu Asp Leu Gly Val Tyr Phe Cys Ser Gln Ser
                85                  90                  95

Thr His Val Pro Pro Thr Phe Gly Gly Gly Thr Lys Leu Glu Ile Lys
            100                 105                 110

<210> SEQ ID NO 215
<211> LENGTH: 112
<212> TYPE: PRT
<213> ORGANISM: Artificial Sequence
<220> FEATURE:
<223> OTHER INFORMATION: Synthetic

<400> SEQUENCE: 215

Asp Val Val Met Thr Gln Thr Pro Leu Ser Leu Pro Val Ser Leu Gly
1               5                   10                  15

Asp Gln Ala Ser Ile Ser Cys Arg Ser Arg Gln Ser Leu Val His Ser
            20                  25                  30

Val Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Glu Phe Thr Leu Glu Ile
65                  70                  75                  80

```
Ser Arg Val Glu Ala Glu Asp Leu Gly Val Tyr Phe Cys Ser Gln Ser
                85                  90                  95

Thr His Val Pro Pro Thr Phe Gly Gly Gly Thr Lys Leu Glu Ile Lys
            100                 105                 110

<210> SEQ ID NO 216
<211> LENGTH: 112
<212> TYPE: PRT
<213> ORGANISM: Artificial Sequence
<220> FEATURE:
<223> OTHER INFORMATION: Synthetic

<400> SEQUENCE: 216

Asp Val Val Met Thr Gln Thr Pro Leu Ser Leu Pro Val Ser Leu Gly
1               5                   10                  15

Asp Gln Ala Ser Ile Ser Cys Arg Ser Arg Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Asn Val Ser Asn Arg Phe Ser Gly Val Pro
    50                  55                  60

Asp Arg Phe Ser Gly Ser Gly Ser Gly Thr Glu Phe Thr Leu Glu Ile
65                  70                  75                  80

Ser Arg Val Glu Ala Glu Asp Leu Gly Val Tyr Phe Cys Ser Gln Ser
                85                  90                  95

Thr His Val Pro Pro Thr Phe Gly Gly Gly Thr Lys Leu Glu Ile Lys
            100                 105                 110

<210> SEQ ID NO 217
<211> LENGTH: 112
<212> TYPE: PRT
<213> ORGANISM: Artificial Sequence
<220> FEATURE:
<223> OTHER INFORMATION: Synthetic

<400> SEQUENCE: 217

Asp Val Val Met Thr Gln Thr Pro Leu Ser Leu Pro Val Ser Leu Gly
1               5                   10                  15

Asp Gln Ala Ser Ile Ser Cys Arg Ser Arg Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Arg Arg Phe Ser Gly Val Pro
    50                  55                  60

Asp Arg Phe Ser Gly Ser Gly Ser Gly Thr Glu Phe Thr Leu Glu Ile
65                  70                  75                  80

Ser Arg Val Glu Ala Glu Asp Leu Gly Val Tyr Phe Cys Ser Gln Ser
                85                  90                  95

Thr His Val Pro Pro Thr Phe Gly Gly Gly Thr Lys Leu Glu Ile Lys
            100                 105                 110

<210> SEQ ID NO 218
<211> LENGTH: 112
<212> TYPE: PRT
<213> ORGANISM: Artificial Sequence
<220> FEATURE:
<223> OTHER INFORMATION: Synthetic

<400> SEQUENCE: 218
```

Asp Val Val Met Thr Gln Thr Pro Leu Ser Leu Pro Val Ser Leu Gly
1               5                   10                  15

Asp Gln Ala Ser Ile Ser Cys Arg Ser Arg Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Arg Ser Gly Val Pro
    50                  55                  60

Asp Arg Phe Ser Gly Ser Gly Ser Gly Thr Glu Phe Thr Leu Glu Ile
65                  70                  75                  80

Ser Arg Val Glu Ala Glu Asp Leu Gly Val Tyr Phe Cys Ser Gln Ser
                85                  90                  95

Thr His Val Pro Pro Thr Phe Gly Gly Gly Thr Lys Leu Glu Ile Lys
            100                 105                 110

<210> SEQ ID NO 219
<211> LENGTH: 112
<212> TYPE: PRT
<213> ORGANISM: Artificial Sequence
<220> FEATURE:
<223> OTHER INFORMATION: Synthetic

<400> SEQUENCE: 219

Asp Val Val Met Thr Gln Thr Pro Leu Ser Leu Pro Val Ser Leu Gly
1               5                   10                  15

Asp Gln Ala Ser Ile Ser Cys Arg Ser Arg Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Glu Phe Thr Leu Glu Ile
65                  70                  75                  80

Ser Arg Val Glu Ala Glu Asp Leu Gly Val Tyr Phe Cys Ser Gln Ser
                85                  90                  95

Thr His Val Pro Pro Thr Phe Gly Gly Gly Thr Lys Leu Glu Ile Lys
            100                 105                 110

<210> SEQ ID NO 220
<211> LENGTH: 112
<212> TYPE: PRT
<213> ORGANISM: Artificial Sequence
<220> FEATURE:
<223> OTHER INFORMATION: Synthetic

<400> SEQUENCE: 220

Asp Val Val Met Thr Gln Thr Pro Leu Ser Leu Pro Val Ser Leu Gly
1               5                   10                  15

Asp Gln Ala Ser Ile Ser Cys Arg Ser Arg Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Leu Phe Ser Gly Val Pro
    50                  55                  60

Asp Arg Phe Ser Gly Ser Gly Ser Gly Thr Glu Phe Thr Leu Glu Ile
65                  70                  75                  80

Ser Arg Val Glu Ala Glu Asp Leu Gly Val Tyr Phe Cys Ser Gln Ser
                85                  90                  95

```
Thr His Val Pro Pro Thr Phe Gly Gly Gly Thr Lys Leu Glu Ile Lys
            100                 105                 110
```

<210> SEQ ID NO 221
<211> LENGTH: 112
<212> TYPE: PRT
<213> ORGANISM: Artificial Sequence
<220> FEATURE:
<223> OTHER INFORMATION: Synthetic

<400> SEQUENCE: 221

```
Asp Val Val Met Thr Gln Thr Pro Leu Ser Leu Pro Val Ser Leu Gly
1               5                   10                  15

Asp Gln Ala Ser Ile Ser Cys Arg Ser Arg Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Glu Phe Thr Leu Glu Ile
65                  70                  75                  80

Ser Arg Val Glu Ala Glu Asp Leu Gly Val Tyr Phe Cys Ser Gln Ser
                85                  90                  95

Thr His Val Ser Pro Thr Phe Gly Gly Gly Thr Lys Leu Glu Ile Lys
            100                 105                 110
```

<210> SEQ ID NO 222
<211> LENGTH: 112
<212> TYPE: PRT
<213> ORGANISM: Artificial Sequence
<220> FEATURE:
<223> OTHER INFORMATION: Synthetic

<400> SEQUENCE: 222

```
Asp Val Val Met Thr Gln Thr Pro Leu Ser Leu Pro Val Ser Leu Gly
1               5                   10                  15

Asp Gln Ala Ser Ile Ser Cys Arg Ser Arg Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Glu Phe Thr Leu Glu Ile
65                  70                  75                  80

Ser Arg Val Glu Ala Glu Asp Leu Gly Val Tyr Phe Cys Ser Gln Ser
                85                  90                  95

Thr His Val Pro Pro Arg Phe Gly Gly Gly Thr Lys Leu Glu Ile Lys
            100                 105                 110
```

<210> SEQ ID NO 223
<211> LENGTH: 112
<212> TYPE: PRT
<213> ORGANISM: Artificial Sequence
<220> FEATURE:
<223> OTHER INFORMATION: Synthetic

<400> SEQUENCE: 223

```
Asp Val Val Met Thr Gln Thr Pro Leu Ser Leu Pro Val Ser Leu Gly
1               5                   10                  15
```

```
Asp Gln Ala Ser Ile Ser Cys Arg Ser Arg Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Glu Phe Thr Leu Glu Ile
65                  70                  75                  80

Ser Arg Val Glu Ala Glu Asp Leu Gly Val Tyr Phe Cys Ser Gln Ser
                85                  90                  95

Thr His Gly Pro Pro Thr Phe Gly Gly Gly Thr Lys Leu Glu Ile Lys
            100                 105                 110
```

<210> SEQ ID NO 224
<211> LENGTH: 112
<212> TYPE: PRT
<213> ORGANISM: Artificial Sequence
<220> FEATURE:
<223> OTHER INFORMATION: Synthetic

<400> SEQUENCE: 224

```
Asp Val Val Met Thr Gln Thr Pro Leu Ser Leu Pro Val Ser Leu Gly
1               5                   10                  15

Asp Gln Ala Ser Ile Ser Cys Arg Ser Arg Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Glu Phe Thr Leu Glu Ile
65                  70                  75                  80

Ser Arg Val Glu Ala Glu Asp Leu Gly Val Tyr Phe Cys Ser Pro Ser
                85                  90                  95

Thr His Val Pro Pro Thr Phe Gly Gly Gly Thr Lys Leu Glu Ile Lys
            100                 105                 110
```

<210> SEQ ID NO 225
<211> LENGTH: 112
<212> TYPE: PRT
<213> ORGANISM: Artificial Sequence
<220> FEATURE:
<223> OTHER INFORMATION: Synthetic

<400> SEQUENCE: 225

```
Asp Val Val Met Thr Gln Thr Pro Leu Ser Leu Pro Val Ser Leu Gly
1               5                   10                  15

Asp Gln Ala Ser Ile Ser Cys Arg Ser Arg Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Glu Phe Thr Leu Glu Ile
65                  70                  75                  80

Ser Arg Val Glu Ala Glu Asp Leu Gly Val Tyr Phe Cys Ser Gln Ser
                85                  90                  95

Thr His Val Ser Pro Thr Phe Gly Gly Gly Thr Lys Leu Glu Ile Lys
            100                 105                 110
```

-continued

<210> SEQ ID NO 226
<211> LENGTH: 112
<212> TYPE: PRT
<213> ORGANISM: Artificial Sequence
<220> FEATURE:
<223> OTHER INFORMATION: Synthetic

<400> SEQUENCE: 226

Glu Val Gln Leu Gln Glu Ser Gly Pro Ser Leu Val Lys Pro Ser Gln
1               5                   10                  15

Thr Leu Ser Leu Thr Cys Ser Val Thr Pro Asp Ser Ile Thr Ser Gly
            20                  25                  30

Tyr Trp Asn Trp Ile Arg Lys Pro Gly Asn Arg Leu Glu Tyr Met Gly
        35                  40                  45

Tyr Ile Ser Tyr Ser Gly Ser Thr Tyr Tyr Asn Pro Ser Leu Lys Ser
    50                  55                  60

Arg Ile Ser Ile Thr Arg Asp Thr Ser Lys Asn Gln Tyr Tyr Leu His
65                  70                  75                  80

Leu Thr Ser Val Thr Thr Glu Asp Thr Ala Thr Tyr Tyr Cys Ala Gln
                85                  90                  95

Gly Asp Gly Ala Tyr Trp Gly Gln Gly Thr Thr Leu Thr Val Ser Ser
            100                 105                 110

<210> SEQ ID NO 227
<211> LENGTH: 112
<212> TYPE: PRT
<213> ORGANISM: Artificial Sequence
<220> FEATURE:
<223> OTHER INFORMATION: Synthetic

<400> SEQUENCE: 227

Glu Val Gln Leu Gln Glu Ser Gly Pro Ser Leu Val Lys Pro Ser Gln
1               5                   10                  15

Thr Leu Ser Leu Thr Cys Ser Val Thr Gly Asp Ser Ile Thr Ser Gly
            20                  25                  30

Tyr Trp Arg Trp Ile Arg Lys Pro Gly Asn Arg Leu Glu Tyr Met Gly
        35                  40                  45

Tyr Ile Ser Tyr Ser Gly Ser Thr Tyr Tyr Asn Pro Ser Leu Lys Ser
    50                  55                  60

Arg Ile Ser Ile Thr Arg Asp Thr Ser Lys Asn Gln Tyr Tyr Leu His
65                  70                  75                  80

Leu Thr Ser Val Thr Thr Glu Asp Thr Ala Thr Tyr Tyr Cys Ala Gln
                85                  90                  95

Gly Asp Gly Ala Tyr Trp Gly Gln Gly Thr Thr Leu Thr Val Ser Ser
            100                 105                 110

<210> SEQ ID NO 228
<211> LENGTH: 112
<212> TYPE: PRT
<213> ORGANISM: Artificial Sequence
<220> FEATURE:
<223> OTHER INFORMATION: Synthetic

<400> SEQUENCE: 228

Glu Val Gln Leu Gln Glu Ser Gly Pro Ser Leu Val Lys Pro Ser Gln
1               5                   10                  15

Thr Leu Ser Leu Thr Cys Ser Val Thr Gly Asp Ser Ile Thr Ser Gly
            20                  25                  30

-continued

Tyr Phe Asn Trp Ile Arg Lys Pro Gly Asn Arg Leu Glu Tyr Met Gly
                35                  40                  45

Tyr Ile Ser Tyr Ser Gly Ser Thr Tyr Tyr Asn Pro Ser Leu Lys Ser
    50                  55                  60

Arg Ile Ser Ile Thr Arg Asp Thr Ser Lys Asn Gln Tyr Tyr Leu His
65                  70                  75                  80

Leu Thr Ser Val Thr Thr Glu Asp Thr Ala Thr Tyr Tyr Cys Ala Gln
                85                  90                  95

Gly Asp Gly Ala Tyr Trp Gly Gln Gly Thr Thr Leu Thr Val Ser Ser
            100                 105                 110

<210> SEQ ID NO 229
<211> LENGTH: 112
<212> TYPE: PRT
<213> ORGANISM: Artificial Sequence
<220> FEATURE:
<223> OTHER INFORMATION: Synthetic

<400> SEQUENCE: 229

Glu Val Gln Leu Gln Glu Ser Gly Pro Ser Leu Val Lys Pro Ser Gln
1               5                   10                  15

Thr Leu Ser Leu Thr Cys Ser Val Thr Gly Asp Ser Ile Thr Ser Gly
                20                  25                  30

Tyr Trp Lys Trp Ile Arg Lys Pro Gly Asn Arg Leu Glu Tyr Met Gly
                35                  40                  45

Tyr Ile Ser Tyr Ser Gly Ser Thr Tyr Tyr Asn Pro Ser Leu Lys Ser
    50                  55                  60

Arg Ile Ser Ile Thr Arg Asp Thr Ser Lys Asn Gln Tyr Tyr Leu His
65                  70                  75                  80

Leu Thr Ser Val Thr Thr Glu Asp Thr Ala Thr Tyr Tyr Cys Ala Gln
                85                  90                  95

Gly Asp Gly Ala Tyr Trp Gly Gln Gly Thr Thr Leu Thr Val Ser Ser
            100                 105                 110

<210> SEQ ID NO 230
<211> LENGTH: 112
<212> TYPE: PRT
<213> ORGANISM: Artificial Sequence
<220> FEATURE:
<223> OTHER INFORMATION: Synthetic

<400> SEQUENCE: 230

Glu Val Gln Leu Gln Glu Ser Gly Pro Ser Leu Val Lys Pro Ser Gln
1               5                   10                  15

Thr Leu Ser Leu Thr Cys Ser Val Thr Gly Asp Ser Ile Thr Ile Gly
                20                  25                  30

Tyr Trp Asn Trp Ile Arg Lys Pro Gly Asn Arg Leu Glu Tyr Met Gly
                35                  40                  45

Tyr Ile Ser Tyr Ser Gly Ser Thr Tyr Tyr Asn Pro Ser Leu Lys Ser
    50                  55                  60

Arg Ile Ser Ile Thr Arg Asp Thr Ser Lys Asn Gln Tyr Tyr Leu His
65                  70                  75                  80

Leu Thr Ser Val Thr Thr Glu Asp Thr Ala Thr Tyr Tyr Cys Ala Gln
                85                  90                  95

Gly Asp Gly Ala Tyr Trp Gly Gln Gly Thr Thr Leu Thr Val Ser Ser
            100                 105                 110

<210> SEQ ID NO 231

```
<211> LENGTH: 112
<212> TYPE: PRT
<213> ORGANISM: Artificial Sequence
<220> FEATURE:
<223> OTHER INFORMATION: Synthetic

<400> SEQUENCE: 231

Glu Val Gln Leu Gln Glu Ser Gly Pro Ser Leu Val Lys Pro Ser Gln
1               5                   10                  15

Thr Leu Ser Leu Thr Cys Ser Val Thr Gly Asp Ser Ile Thr Ser Gly
            20                  25                  30

Tyr Trp Asn Trp Ile Arg Lys Pro Gly Asn Arg Leu Glu Tyr Met Gly
        35                  40                  45

Phe Ile Ser Tyr Ser Gly Ser Thr Tyr Tyr Asn Pro Ser Leu Lys Ser
    50                  55                  60

Arg Ile Ser Ile Thr Arg Asp Thr Ser Lys Asn Gln Tyr Tyr Leu His
65                  70                  75                  80

Leu Thr Ser Val Thr Thr Glu Asp Thr Ala Thr Tyr Tyr Cys Ala Gln
                85                  90                  95

Gly Asp Gly Ala Tyr Trp Gly Gln Gly Thr Thr Leu Thr Val Ser Ser
            100                 105                 110

<210> SEQ ID NO 232
<211> LENGTH: 112
<212> TYPE: PRT
<213> ORGANISM: Artificial Sequence
<220> FEATURE:
<223> OTHER INFORMATION: Synthetic

<400> SEQUENCE: 232

Glu Val Gln Leu Gln Glu Ser Gly Pro Ser Leu Val Lys Pro Ser Gln
1               5                   10                  15

Thr Leu Ser Leu Thr Cys Ser Val Thr Gly Asp Ser Ile Thr Ser Gly
            20                  25                  30

Tyr Trp Asn Trp Ile Arg Lys Pro Gly Asn Arg Leu Glu Tyr Met Gly
        35                  40                  45

Tyr Ile Ser Tyr Arg Gly Ser Thr Tyr Tyr Asn Pro Ser Leu Lys Ser
    50                  55                  60

Arg Ile Ser Ile Thr Arg Asp Thr Ser Lys Asn Gln Tyr Tyr Leu His
65                  70                  75                  80

Leu Thr Ser Val Thr Thr Glu Asp Thr Ala Thr Tyr Tyr Cys Ala Gln
                85                  90                  95

Gly Asp Gly Ala Tyr Trp Gly Gln Gly Thr Thr Leu Thr Val Ser Ser
            100                 105                 110

<210> SEQ ID NO 233
<211> LENGTH: 112
<212> TYPE: PRT
<213> ORGANISM: Artificial Sequence
<220> FEATURE:
<223> OTHER INFORMATION: Synthetic

<400> SEQUENCE: 233

Glu Val Gln Leu Gln Glu Ser Gly Pro Ser Leu Val Lys Pro Ser Gln
1               5                   10                  15

Thr Leu Ser Leu Thr Cys Ser Val Thr Gly Asp Ser Ile Thr Ser Gly
            20                  25                  30

Tyr Trp Asn Trp Ile Arg Lys Pro Gly Asn Arg Leu Glu Tyr Met Gly
        35                  40                  45
```

Tyr Ile Ser Tyr Ser Gly Ser Ile Tyr Tyr Asn Pro Ser Leu Lys Ser
            50                  55                  60

Arg Ile Ser Ile Thr Arg Asp Thr Ser Lys Asn Gln Tyr Tyr Leu His
 65                  70                  75                  80

Leu Thr Ser Val Thr Thr Glu Asp Thr Ala Thr Tyr Tyr Cys Ala Gln
                85                  90                  95

Gly Asp Gly Ala Tyr Trp Gly Gln Gly Thr Thr Leu Thr Val Ser Ser
            100                 105                 110

<210> SEQ ID NO 234
<211> LENGTH: 112
<212> TYPE: PRT
<213> ORGANISM: Artificial Sequence
<220> FEATURE:
<223> OTHER INFORMATION: Synthetic

<400> SEQUENCE: 234

Glu Val Gln Leu Gln Glu Ser Gly Pro Ser Leu Val Lys Pro Ser Gln
 1               5                  10                  15

Thr Leu Ser Leu Thr Cys Ser Val Thr Gly Asp Ser Ile Thr Ser Gly
            20                  25                  30

Tyr Trp Asn Trp Ile Arg Lys Pro Gly Asn Arg Leu Glu Tyr Met Gly
        35                  40                  45

Tyr Ile Ser Tyr Ser Gly Asp Thr Tyr Tyr Asn Pro Ser Leu Lys Ser
            50                  55                  60

Arg Ile Ser Ile Thr Arg Asp Thr Ser Lys Asn Gln Tyr Tyr Leu His
 65                  70                  75                  80

Leu Thr Ser Val Thr Thr Glu Asp Thr Ala Thr Tyr Tyr Cys Ala Gln
                85                  90                  95

Gly Asp Gly Ala Tyr Trp Gly Gln Gly Thr Thr Leu Thr Val Ser Ser
            100                 105                 110

<210> SEQ ID NO 235
<211> LENGTH: 112
<212> TYPE: PRT
<213> ORGANISM: Artificial Sequence
<220> FEATURE:
<223> OTHER INFORMATION: Synthetic

<400> SEQUENCE: 235

Glu Val Gln Leu Gln Glu Ser Gly Pro Ser Leu Val Lys Pro Ser Gln
 1               5                  10                  15

Thr Leu Ser Leu Thr Cys Ser Val Thr Gly Asp Ser Ile Thr Ser Gly
            20                  25                  30

Tyr Trp Asn Trp Ile Arg Lys Pro Gly Asn Arg Leu Glu Tyr Met Gly
        35                  40                  45

Tyr Ile Ser Tyr Thr Gly Ser Thr Tyr Tyr Asn Pro Ser Leu Lys Ser
            50                  55                  60

Arg Ile Ser Ile Thr Arg Asp Thr Ser Lys Asn Gln Tyr Tyr Leu His
 65                  70                  75                  80

Leu Thr Ser Val Thr Thr Glu Asp Thr Ala Thr Tyr Tyr Cys Ala Gln
                85                  90                  95

Gly Asp Gly Ala Tyr Trp Gly Gln Gly Thr Thr Leu Thr Val Ser Ser
            100                 105                 110

<210> SEQ ID NO 236
<211> LENGTH: 112
<212> TYPE: PRT
<213> ORGANISM: Artificial Sequence

```
<220> FEATURE:
<223> OTHER INFORMATION: Synthetic

<400> SEQUENCE: 236

Glu Val Gln Leu Gln Glu Ser Gly Pro Ser Leu Val Lys Pro Ser Gln
1               5                   10                  15

Thr Leu Ser Leu Thr Cys Ser Val Thr Gly Asp Ser Ile Thr Ser Gly
            20                  25                  30

Tyr Trp Asn Trp Ile Arg Lys Pro Gly Asn Arg Leu Glu Tyr Met Gly
        35                  40                  45

Tyr Ile Ser Tyr Ser Gly Ser Thr Tyr Tyr Lys Pro Ser Leu Lys Ser
    50                  55                  60

Arg Ile Ser Ile Thr Arg Asp Thr Ser Lys Asn Gln Tyr Tyr Leu His
65                  70                  75                  80

Leu Thr Ser Val Thr Thr Glu Asp Thr Ala Thr Tyr Tyr Cys Ala Gln
                85                  90                  95

Gly Asp Gly Ala Tyr Trp Gly Gln Gly Thr Thr Leu Thr Val Ser Ser
            100                 105                 110

<210> SEQ ID NO 237
<211> LENGTH: 112
<212> TYPE: PRT
<213> ORGANISM: Artificial Sequence
<220> FEATURE:
<223> OTHER INFORMATION: Synthetic

<400> SEQUENCE: 237

Glu Val Gln Leu Gln Glu Ser Gly Pro Ser Leu Val Lys Pro Ser Gln
1               5                   10                  15

Thr Leu Ser Leu Thr Cys Ser Val Thr Gly Asp Ser Ile Thr Ser Gly
            20                  25                  30

Tyr Trp Asn Trp Ile Arg Lys Pro Gly Asn Arg Leu Glu Tyr Met Gly
        35                  40                  45

Tyr Ile Ser Tyr Ser Gly Ser Thr Tyr Tyr Asn Pro Phe Leu Lys Ser
    50                  55                  60

Arg Ile Ser Ile Thr Arg Asp Thr Ser Lys Asn Gln Tyr Tyr Leu His
65                  70                  75                  80

Leu Thr Ser Val Thr Thr Glu Asp Thr Ala Thr Tyr Tyr Cys Ala Gln
                85                  90                  95

Gly Asp Gly Ala Tyr Trp Gly Gln Gly Thr Thr Leu Thr Val Ser Ser
            100                 105                 110

<210> SEQ ID NO 238
<211> LENGTH: 112
<212> TYPE: PRT
<213> ORGANISM: Artificial Sequence
<220> FEATURE:
<223> OTHER INFORMATION: Synthetic

<400> SEQUENCE: 238

Glu Val Gln Leu Gln Glu Ser Gly Pro Ser Leu Val Lys Pro Ser Gln
1               5                   10                  15

Thr Leu Ser Leu Thr Cys Ser Val Thr Gly Asp Ser Ile Thr Ser Gly
            20                  25                  30

Tyr Trp Asn Trp Ile Arg Lys Pro Gly Asn Arg Leu Glu Tyr Met Gly
        35                  40                  45

Tyr Ile Ser Tyr Ser Gly Ser Thr Tyr Phe Asn Pro Ser Leu Lys Ser
    50                  55                  60
```

```
Arg Ile Ser Ile Thr Arg Asp Thr Ser Lys Asn Gln Tyr Tyr Leu His
 65                 70                  75                  80

Leu Thr Ser Val Thr Thr Glu Asp Thr Ala Thr Tyr Tyr Cys Ala Gln
                85                  90                  95

Gly Asp Gly Ala Tyr Trp Gly Gln Gly Thr Thr Leu Thr Val Ser Ser
            100                 105                 110
```

<210> SEQ ID NO 239
<211> LENGTH: 112
<212> TYPE: PRT
<213> ORGANISM: Artificial Sequence
<220> FEATURE:
<223> OTHER INFORMATION: Synthetic

<400> SEQUENCE: 239

```
Glu Val Gln Leu Gln Glu Ser Gly Pro Ser Leu Val Lys Pro Ser Gln
 1               5                  10                  15

Thr Leu Ser Leu Thr Cys Ser Val Thr Gly Asp Ser Ile Thr Ser Gly
            20                  25                  30

Tyr Trp Asn Trp Ile Arg Lys Pro Gly Asn Arg Leu Glu Tyr Met Gly
        35                  40                  45

Tyr Ile Ser Tyr Ser Gly Ser Thr Tyr Tyr Asn Pro Ser Leu Lys Asn
 50                 55                  60

Arg Ile Ser Ile Thr Arg Asp Thr Ser Lys Asn Gln Tyr Tyr Leu His
 65                 70                  75                  80

Leu Thr Ser Val Thr Thr Glu Asp Thr Ala Thr Tyr Tyr Cys Ala Gln
                85                  90                  95

Gly Asp Gly Ala Tyr Trp Gly Gln Gly Thr Thr Leu Thr Val Ser Ser
            100                 105                 110
```

<210> SEQ ID NO 240
<211> LENGTH: 112
<212> TYPE: PRT
<213> ORGANISM: Artificial Sequence
<220> FEATURE:
<223> OTHER INFORMATION: Synthetic

<400> SEQUENCE: 240

```
Glu Val Gln Leu Gln Glu Ser Gly Pro Ser Leu Val Lys Pro Ser Gln
 1               5                  10                  15

Thr Leu Ser Leu Thr Cys Ser Val Thr Gly Asp Ser Ile Thr Ser Gly
            20                  25                  30

Tyr Trp Asn Trp Ile Arg Lys Pro Gly Asn Arg Leu Glu Tyr Met Gly
        35                  40                  45

Tyr Ile Ser Tyr Ser Gly Ser Thr Tyr Tyr Asn Pro Ser Leu Lys Ser
 50                 55                  60

Arg Ile Ser Ile Thr Arg Asp Thr Ser Lys Asn Gln Tyr Tyr Leu His
 65                 70                  75                  80

Leu Thr Ser Val Thr Thr Glu Asp Thr Ala Thr Tyr Tyr Cys Ala Gln
                85                  90                  95

Gly Asp Gly Ala Tyr Trp Gly Gln Gly Thr Thr Leu Thr Val Ser Ser
            100                 105                 110
```

<210> SEQ ID NO 241
<211> LENGTH: 112
<212> TYPE: PRT
<213> ORGANISM: Artificial Sequence
<220> FEATURE:
<223> OTHER INFORMATION: Synthetic

```
<400> SEQUENCE: 241

Glu Val Gln Leu Gln Glu Ser Gly Pro Ser Leu Val Lys Pro Ser Gln
1               5                   10                  15

Thr Leu Ser Leu Thr Cys Ser Val Thr Gly Asp Ser Ile Thr Ser Gly
            20                  25                  30

Tyr Trp Asn Trp Ile Arg Lys Pro Gly Asn Arg Leu Glu Tyr Met Gly
        35                  40                  45

Tyr Ile Ser Tyr Ser Gly Ser Thr Tyr Tyr Asn Pro Ser Leu Lys Ser
    50                  55                  60

Arg Ile Ser Ile Thr Arg Asp Thr Ser Lys Asn Gln Tyr Tyr Leu His
65                  70                  75                  80

Leu Thr Ser Val Thr Thr Glu Asp Thr Ala Thr Tyr Tyr Cys Ala Gln
                85                  90                  95

Gly Asp Gly Asp Tyr Trp Gly Gln Gly Thr Thr Leu Thr Val Ser Ser
            100                 105                 110

<210> SEQ ID NO 242
<211> LENGTH: 112
<212> TYPE: PRT
<213> ORGANISM: Artificial Sequence
<220> FEATURE:
<223> OTHER INFORMATION: Synthetic

<400> SEQUENCE: 242

Glu Val Gln Leu Gln Glu Ser Gly Pro Ser Leu Val Lys Pro Ser Gln
1               5                   10                  15

Thr Leu Ser Leu Thr Cys Ser Val Thr Gly Asp Ser Ile Thr Ser Gly
            20                  25                  30

Tyr Trp Asn Trp Ile Arg Lys Pro Gly Asn Arg Leu Glu Tyr Met Gly
        35                  40                  45

Tyr Ile Ser Tyr Ser Gly Ser Thr Tyr Tyr Asn Pro Ser Leu Lys Ser
    50                  55                  60

Arg Ile Ser Ile Thr Arg Asp Thr Ser Lys Asn Gln Tyr Tyr Leu His
65                  70                  75                  80

Leu Thr Ser Val Thr Thr Glu Asp Thr Ala Thr Tyr Tyr Cys Ala Gln
                85                  90                  95

Gly Asp Thr Ala Tyr Trp Gly Gln Gly Thr Thr Leu Thr Val Ser Ser
            100                 105                 110

<210> SEQ ID NO 243
<211> LENGTH: 112
<212> TYPE: PRT
<213> ORGANISM: Artificial Sequence
<220> FEATURE:
<223> OTHER INFORMATION: Synthetic

<400> SEQUENCE: 243

Glu Val Gln Leu Gln Glu Ser Gly Pro Ser Leu Val Lys Pro Ser Gln
1               5                   10                  15

Thr Leu Ser Leu Thr Cys Ser Val Thr Gly Asp Ser Ile Thr Ser Gly
            20                  25                  30

Tyr Trp Asn Trp Ile Arg Lys Pro Gly Asn Arg Leu Glu Tyr Met Gly
        35                  40                  45

Tyr Ile Ser Tyr Ser Gly Ser Thr Tyr Tyr Asn Pro Ser Leu Lys Ser
    50                  55                  60

Arg Ile Ser Ile Thr Arg Asp Thr Ser Lys Asn Gln Tyr Tyr Leu His
65                  70                  75                  80
```

Leu Thr Ser Val Thr Thr Glu Asp Thr Ala Thr Tyr Tyr Cys Ala Gln
                85                  90                  95

Ala Asp Gly Ala Tyr Trp Gly Gln Gly Thr Thr Leu Thr Val Ser Ser
            100                 105                 110

<210> SEQ ID NO 244
<211> LENGTH: 112
<212> TYPE: PRT
<213> ORGANISM: Artificial Sequence
<220> FEATURE:
<223> OTHER INFORMATION: Synthetic

<400> SEQUENCE: 244

Glu Val Gln Leu Gln Glu Ser Gly Pro Ser Leu Val Lys Pro Ser Gln
1               5                   10                  15

Thr Leu Ser Leu Thr Cys Ser Val Thr Gly Asp Ser Ile Thr Ser Gly
            20                  25                  30

Tyr Trp Asn Trp Ile Arg Lys Pro Gly Asn Arg Leu Glu Tyr Met Gly
        35                  40                  45

Tyr Ile Ser Tyr Ser Gly Ser Thr Tyr Tyr Asn Pro Ser Leu Lys Ser
    50                  55                  60

Arg Ile Ser Ile Thr Arg Asp Thr Ser Lys Asn Gln Tyr Tyr Leu His
65                  70                  75                  80

Leu Thr Ser Val Thr Thr Glu Asp Thr Ala Thr Tyr Tyr Cys Ala Gln
                85                  90                  95

Gly Trp Gly Ala Tyr Trp Gly Gln Gly Thr Thr Leu Thr Val Ser Ser
            100                 105                 110

<210> SEQ ID NO 245
<211> LENGTH: 112
<212> TYPE: PRT
<213> ORGANISM: Artificial Sequence
<220> FEATURE:
<223> OTHER INFORMATION: Synthetic

<400> SEQUENCE: 245

Glu Val Gln Leu Gln Glu Ser Gly Pro Ser Leu Val Lys Pro Ser Gln
1               5                   10                  15

Thr Leu Ser Leu Thr Cys Ser Val Thr Gly Asp Ser Ile Thr Ser Gly
            20                  25                  30

Tyr Trp Asn Trp Ile Arg Lys Pro Gly Asn Arg Leu Glu Tyr Met Gly
        35                  40                  45

Tyr Ile Ser Tyr Ser Gly Ser Thr Tyr Tyr Asn Pro Ser Leu Lys Ser
    50                  55                  60

Arg Ile Ser Ile Thr Arg Asp Thr Ser Lys Asn Gln Tyr Tyr Leu His
65                  70                  75                  80

Leu Thr Ser Val Thr Thr Glu Asp Thr Ala Thr Tyr Tyr Cys Ala Gln
                85                  90                  95

Glu Asp Gly Ala Tyr Trp Gly Gln Gly Thr Thr Leu Thr Val Ser Ser
            100                 105                 110

<210> SEQ ID NO 246
<211> LENGTH: 8
<212> TYPE: PRT
<213> ORGANISM: Artificial Sequence
<220> FEATURE:
<223> OTHER INFORMATION: Synthetic

<400> SEQUENCE: 246

Arg Ser Arg Gln Gly Leu Val His

```
<210> SEQ ID NO 247
<211> LENGTH: 5
<212> TYPE: PRT
<213> ORGANISM: Artificial Sequence
<220> FEATURE:
<223> OTHER INFORMATION: Synthetic

<400> SEQUENCE: 247

Gly Asp Gly Gln Tyr
1               5

<210> SEQ ID NO 248
<211> LENGTH: 5
<212> TYPE: PRT
<213> ORGANISM: Artificial Sequence
<220> FEATURE:
<223> OTHER INFORMATION: Synthetic

<400> SEQUENCE: 248

Gly Asp Gly Gly Tyr
1               5
```

ANTIBODY-BASED AFFINITY REAGENTS FOR BINDING PACLITAXEL

CROSS-REFERENCE TO RELATED APPLICATION

This application claims the benefit of U.S. Provisional Patent Application No. 62/238,667, filed on Oct. 7, 2015, which is incorporated herein by reference.

STATEMENT REGARDING SEQUENCE LISTING

The sequence listing associated with this application is provided in text format in lieu of a paper copy and is hereby incorporated by reference into the specification. The name of the text file containing the sequence listing is 56964_Seq_Listing_Final_2016-10-06.txt. The text file is 103 KB; was created on Oct. 6, 2016; and is being submitted via EFS-Web with the filing of the specification.

FIELD OF THE INVENTION

The present invention provides optimized affinity reagent compositions, such as antibodies, antibody fragments, and antibody derivatives, for binding paclitaxel.

BACKGROUND

Paclitaxel, originally isolated from the bark of Pacific Yew tree, has been established as one of the most effective chemotherapeutic drugs for a range of cancer types including lung, ovarian, and breast cancers. A major limitation of paclitaxel is its low solubility and the need to be formulated in toxic organic solvents, typically polyoxyethylated castor oil and dehydrated ethanol mixtures (known as Taxol®). To prevent the solvent toxicity, paclitaxel has been formulated with a variety of excipients as well as using nanoparticle delivery systems that can improve the solubility of hydrophobic drugs such as paclitaxel.

Abraxane®, a paclitaxel albumin bound nanoparticle formulation was approved by FDA in 2005 and is currently one of the best formulations of paclitaxel for chemotherapy. Other systems have been investigated for the delivery of paclitaxel or are in development, e.g., using polymeric nanoparticles, lipid-based nanoparticle formulations, polymer conjugates, inorganic nanoparticles, carbon nanotubes, nanocrystals, or cyclodextrin nanoparticles (see, for example, Ping Ma et al., 2013, J Nanomed. Nanotechnology:4:2).

Although Abraxane® is a widely used chemotherapeutic agent and practically applicable to all cancer types, the response to Abraxane®, however, can be as low as 20%. The relative insensitivity to paclitaxel found in some patients could be a contributing factor to low response rate. However, this insensitivity may not be the primary reason for the low response rate. There is up to 10-fold variations in blood concentration of paclitaxel monitored in clinical patients' samples when dosed at the various approved doses (260 mg/m$^2$ for metastatic breast cancer, 125 mg/m$^2$ for pancreatic cancer, and 100 mg/m$^2$ for lung cancer (Nyman D W et al., 2005, J Clin. Oncol. 23, 7785-93)). This variation suggests that the vast majority of patients are potentially dosed incorrectly with either too great a concentration of paclitaxel administration, and had to be taken off the treatment, or too low a dosage administered and providing no benefit from the treatment. Even if patients are sensitive to paclitaxel, having an insufficient drug level would render them nonresponsive and the treatment ineffective. The under-dosed group is the most vulnerable patient population, as it is difficult to determine whether they are insensitive to paclitaxel or not administered sufficient paclitaxel. Full pharmacokinetic (PK) profiling is the only approach in such cases to provide guidance for proper drug dose based on the individual pharmacokinetic variation.

Currently there are no available methods to perform a full PK quantitation of paclitaxel without having the patient enrolled in comprehensive clinical testing, which requires a hospital stay. Typical duration of such PK testing may be over a 48 hour period and includes repetitive blood drawing. Presently, the use of complex laboratory equipment is required to analyze blood concentration of paclitaxel, including liquid chromatography/mass spectrometry (LC/MS) methods. These methods are extremely costly, currently over $120/sample and the equipment cost is in the range exceeding $150K-$200K per instrument. It has also been demonstrated that a minimum of four data points collected over a period of 48 to 72 hours is needed to adequately characterize the PK parameters for each particular patient. Keeping the patients in hospital for PK testing can easily push the cost to roughly $10,000 per patient. A sufficiently powered Phase III clinical trial to demonstrate clinical efficacy for PK guided dosing would require 500 patients (250 patients for BSA dosing and 250 patients for PK guided dosing). The bioanalytical cost alone would be $1.5M (500 points×6 cycles of chemotherapy×4 blood samplings for PK analysis×$120/sample analysis). The other components of trial would cost roughly $100,000 per patient, totaling $50M. This represents a significant barrier to obtaining meaningful clinical data necessary to guide dose adjustment for optimum tumor response and regulatory approval of the device. The high cost of the analysis and instrumentation, therefore, has prohibitive consequences on establishing therapeutic drug monitoring (TDM) for many drugs that have a relatively narrow therapeutic range.

Accordingly, a need remains for simple, effective, and inexpensive reagents and strategies to monitor the pharmacokinetics of paclitaxel in a patient, thereby appropriately personalizing the therapy to the individual patient by informing any adjustment of the dosing strategy. The present invention seeks to fulfill this need and provides further related advantages.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In one aspect, the present disclosure provides an affinity reagent that binds to paclitaxel. The affinity reagent can be a monoclonal antibody, antibody fragment, or antibody derivative that is derived from monoclonal antibodies 8A10 or 3C6. In some embodiments, the affinity reagent comprises between one and six of the complementary determining regions (CDRs) of antibody 8A10 or 3C6. In some embodiments, the affinity reagent comprises between one and six CDRs that comprise an amino acid sequence with at least one amino acid difference relative to a CDR of antibody 8A10 or 3C6. In some embodiments, the affinity reagent contains at least one amino acid difference with respect to a non-CDR region of a variable domain of antibody 8A10 or 3C6.

In another aspect, the disclosure provides methods of detecting paclitaxel in a sample, comprising contacting the sample with an affinity reagent as described herein and detecting the formation of a complex between paclitaxel and the affinity reagent. In one embodiment, the method also comprises quantifying the level of paclitaxel in the sample. In one embodiment, the method can also include determining the amount of paclitaxel in a subject when the sample is a biological sample obtained from the subject. The method can further comprise determining whether sufficient or insufficient paclitaxel has been or is being administered to the subject. In yet a further embodiment, the method further comprises increasing or decreasing the amount of paclitaxel (or paclitaxel-based therapeutic) administered to the subject based on the results of the quantification of paclitaxel in the sample obtained from the subject.

In another aspect, the disclosure provides kits and devices configured to detect and/or quantify paclitaxel in a sample, comprising the affinity reagents described herein.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIGS. 6A-6G graphically illustrate ELISA assays demonstrating the binding of select 8A10 derived Fab variants (i.e., with single CDR amino acid variations) to BSA-paclitaxel.

FIG. 8 is an amino acid sequence alignment for the variable light chain region and variable heavy chain region that includes sequences from the reference 8A10 antibody and variants obtained from the combinatorial library. The numbers in parentheses refer to the reference SEQ ID NOS for each respective sequence as set forth in the Sequence Listing. Regions of variation are indicated.

FIG. 9 is series of an amino acid sequence alignments for the variable light chain region that includes sequences from the reference 3C6 antibody and Fab variants obtained from the individual CDR mutation libraries. The CDR regions are indicated in dark highlighting in the 3C6 VL sequence, and variation in the Fab variants is indicated in light highlighting. It is noted that the L1a and L1b library results are indicated in separate alignments. The numbers in parentheses refer to the reference SEQ ID NOS for each respective sequence as set forth in the Sequence Listing.

FIG. 10 is series of an amino acid sequence alignments for the variable heavy chain region that includes sequences from the reference 3C6 antibody and Fab variants obtained from the individual CDR mutation libraries. The CDR regions are indicated in dark highlighting in the 3C6 VH sequence, and variation in the Fab variants is indicated in light highlighting. It is noted that the H2a and H2b library results are indicated in separate alignments. The numbers in parentheses refer to the reference SEQ ID NOS for each respective sequence as set forth in the Sequence Listing.

DETAILED DESCRIPTION

Figure 1:
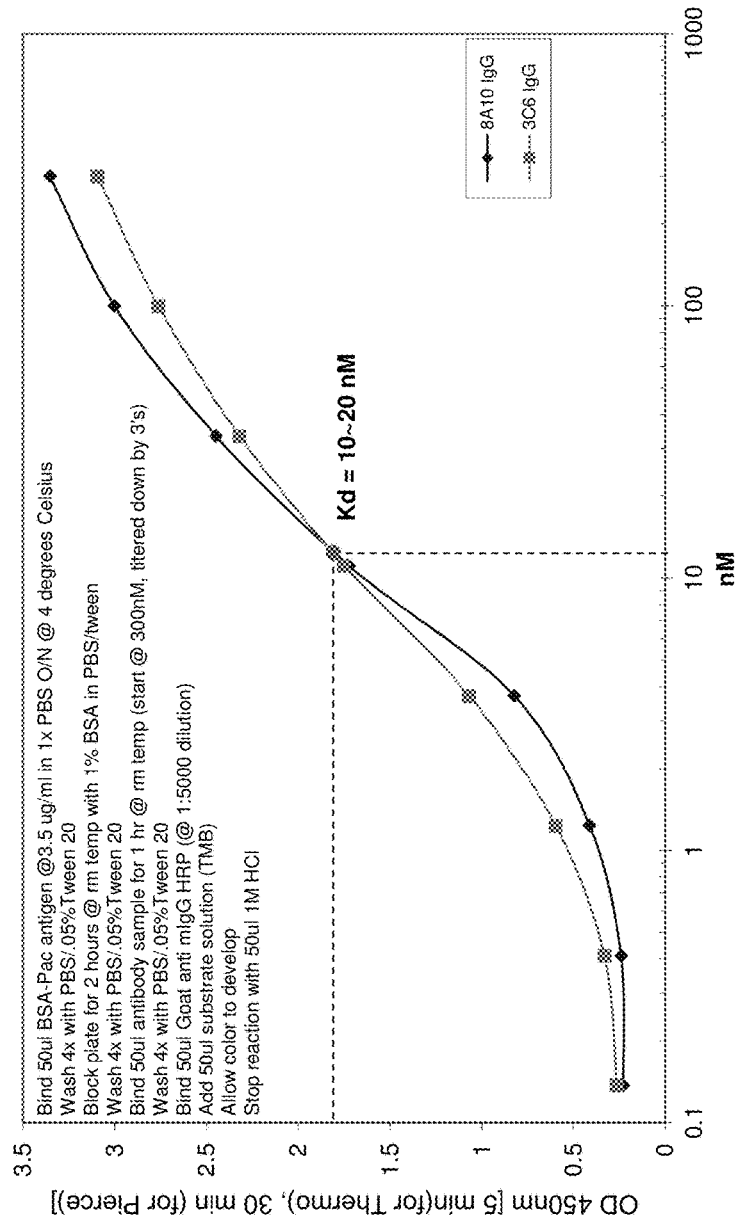
FIG. 1 is a graph illustrating direct binding of intact mAb 8A10 IgG (and 3C6) to a BSA-paclitaxel antigen.

The present disclosure generally relates to affinity reagents, such as antibody-based compositions including antibody variants, antibody fragments, and antibody derivatives that bind to paclitaxel. As described in more detail below, the inventors initially developed monoclonal antibodies, such as 8A10 and 3C6, that were demonstrated to bind to paclitaxel and to be useful for the detection of paclitaxel in a biological sample. The inventors constructed libraries that incorporated single amino acid sequence variations for each position in each CDR of the reference 8A10 and 3C6 anti-paclitaxel antibodies. The 8A10 libraries were screened for variant Fab domains exhibiting binding to paclitaxel antigen. Specific mutations of "positive" variants were combined in a combinatorial library and screened again to confirm binding. These results indicate that affinity reagents that are useful, for example, as compositions for the binding, isolation, and/or detection of paclitaxel, can be generated from known paclitaxel-binding antibodies, such as 8A10 and 3C6.

In accordance with the foregoing, in one aspect the present disclosure provides an affinity reagent that binds to paclitaxel. In any of the embodiments described herein, the affinity reagent binds to paclitaxel, as can be determined by any technique known in the art. An exemplary technique for paclitaxel binding is described in more detail below. In one embodiment, the affinity reagent is a monoclonal antibody, antibody fragment, or antibody derivative. The affinity reagent can be an antibody fragment or antibody derivative of a known antibody reagent that binds to paclitaxel, such as 8A10 or 3C6.

In one embodiment, the affinity reagent comprises six complementary determining regions, namely three on the light chain framework (i.e., also referred to as CDRL1, CDRL2, and CDRL3) and three on the heavy chain framework (i.e., also referred to as CDRH1, CDRH2, and CDRH3).

8A10-derived Affinity Reagents

In one embodiment, the affinity reagent comprises one, two, three, four, five, or all six of the complementary determining regions contained in the 8A10 mAb. Specifically, the affinity reagent can comprise a CDRL1 with the amino acid sequence set forth in SEQ ID NO:11, a CDRL2 with the amino acid sequence set forth in SEQ ID NO:31, a CDRL3 with the amino acid sequence set forth in SEQ ID NO:45, a CDRH1 with the amino acid sequence set forth in SEQ ID NO:58, a CDRH2 with the amino acid sequence set forth in SEQ ID NO:68, and/or a CDRH3 with the amino acid sequence set forth in SEQ ID NO:99, and/or any combination thereof.

In a further embodiment, the affinity reagent comprises at least one amino acid difference relative to the amino acid sequence of 8A10 mAb, as described in more detail below. The sequence of the mAb is known and discernable by persons of ordinary skill in the art. In one embodiment, the affinity reagent comprises at least one amino acid difference in the framework (i.e., non-CDR) sequence of the variable region of the 8A10 heavy chain or light chain.

In another embodiment, the affinity reagent comprises one, two, three, four, five or all six of the CDRs corresponding to the CDRs of the 8A10 mAb, but also comprises at least one mutation, e.g., an amino acid difference, in any one or more of the six CDRs relative to 8A10 mAb, in any combination. Specifically, the affinity reagent can comprise at least one amino acid difference in at least one of the CDRs relative to: a CDRL1 with the amino acid sequence set forth in SEQ ID NO:11, a CDRL2 with the amino acid sequence set forth in SEQ ID NO:31, a CDRL3 with the amino acid sequence set forth in SEQ ID NO:45, a CDRH1 with the amino acid sequence set forth in SEQ ID NO:58, a CDRH2 with the amino acid sequence set forth in SEQ ID NO:68, and/or a CDRH3 with the amino acid sequence set forth in SEQ ID NO:99, and/or any combination thereof.

In one embodiment, the affinity reagent specifically comprises:

a light chain complementary determining region CDR1 with the amino acid sequence KPXQXVXSXVX, as set forth in SEQ ID NO:1,
  wherein X at position 3 is S or V,
  wherein X at position 5 is N, T, D, M, R, or K,
  wherein X at position 7 is G or F,
  wherein X at position 9 is A, P, or R,
  wherein X at position 11 is T, N, or A;
a light chain complementary determining region CDR2 with the amino acid sequence XXXXRYX, as set forth in SEQ ID NO:2,
  wherein X at position 1 is S or Y,
  wherein X at position 2 is A, H, or T,
  wherein X at position 3 is S or T,
  wherein X at position 4 is N or R,
  wherein X at position 7 is T, M, or R;
a light chain complementary determining region CDR3 with the amino acid sequence QQYXSXPYX, as set forth in SEQ ID NO:3,
  wherein X at position 4 is S or P,
  wherein X at position 6 is Y, K, R, or V,
  wherein X at position 9 is T or R;
a heavy chain complementary determining region CDR1 with the amino acid sequence GXXFXDXXXX, as set forth in SEQ ID NO:4,
  wherein X at position 2 is Y or S,
  wherein X at position 3 is T or R,
  wherein X at position 5 is T, S, or H,
  wherein X at position 7 is S or Y,
  wherein X at position 8 is T or R,
  wherein X at position 9 is M or T,
  wherein X at position 10 is N or K;
a heavy chain complementary determining region CDR2 with the amino acid sequence XIXPXXXXXXXNQXFXX, as set forth in SEQ ID NO:5,
  wherein X at position 1 is E or K
  wherein X at position 3 is D, F, W, or A
  wherein X at position 5 is N, T, M, S, K, W, or R
  wherein X at position 6 is N, S, D, or R
  wherein X at position 7 is G or L
  wherein X at position 8 is G, W, or R
  wherein X at position 9 is T or A
  wherein X at position 10 is N, R, or A
  wherein X at position 11 is Y or T
  wherein X at position 14 is K or N
  wherein X at position 16 is K or S
  wherein X at position 17 is G or L; and/or
a heavy chain complementary determining region CDR3 with the amino acid sequence ARXXWG, as set forth in SEQ ID NO:6,
  wherein X at position 3 is G, R, or P
  wherein X at position 4 is V, P or S;
wherein the monoclonal antibody, antibody fragment, or antibody derivative binds to paclitaxel.

As used herein, the term "antibody" encompasses whole antibodies and functional antibody fragments thereof, derived from any antibody-producing mammal (e.g., mouse, rat, rabbit, camelid, and primate, including human) or synthetically or recombinantly produced, that specifically binds to a target of interest (e.g., paclitaxel) or portions thereof. Exemplary antibodies include polyclonal, monoclonal, and recombinant antibodies; multispecific antibodies (e.g., bispecific antibodies); humanized antibodies; murine antibodies; chimeric, mouse-human, mouse-primate, primate-human monoclonal antibodies; and anti-idiotype antibodies, and may be any intact molecule or fragment thereof, such as an antigen binding fragment. As described herein, monoclonal antibodies are advantageous because they provide for increased specificity in binding of the antigen of choice, such as a therapeutic drug (e.g., paclitaxel). However, "clonal" compositions comprising only one antibody fragment or derivative are also possible.

As used herein, the term "antibody fragments" can refer to "antigen binding fragments." The term "antigen binding fragments" refers to the antigen binding or variable region from or related to a full-length antibody. Illustrative examples of antibody fragments include Fab, Fab', F(ab)$_2$, F(ab')$_2$, and Fv fragments, scFv fragments, diabodies, nanobodies, linear antibodies, single-chain antibody molecules, and multispecific antibodies formed from antibody fragments.

As used herein, a "single-chain Fv" or "scFv" antibody fragment comprises the $V_H$ and $V_L$ domains of an antibody, wherein these domains are present in a single polypeptide chain. Generally, the Fv polypeptide further comprises a polypeptide linker between the $V_H$ and $V_L$ domains, which enables the scFv to form the desired structure for antigen binding.

As used herein, a "chimeric antibody" is a recombinant protein that contains the variable domains and complementarity-determining regions derived from a non-human species (e.g., rodent) antibody, while the remainder of the antibody molecule is derived from a human antibody.

As used herein, a "humanized antibody" is a chimeric antibody that comprises a minimal sequence that conforms to specific complementarity-determining regions derived from non-human immunoglobulin that is transplanted into a human antibody framework. Humanized antibodies are typically recombinant proteins in which only the antibody complementarity-determining regions are of non-human origin.

As used herein, the term "derivative" indicates that the antibody or antibody fragment has been produced from a reference antibody. For example, sometimes it is desirable to modify or enhance binding characteristics of a reference antibody, such as disclosed herein with reference to the anti-paclitaxel monoclonal antibody 8A10 (or 3C6 antibody, as described below). As described in more detail below, the 8A10 and 3C6 antibodies were subjected to various modifications, including mutations subjected to the encoding DNA, to alter binding properties. The resulting antibody products with altered properties are then referred to as a "derivative" of the reference antibody. For example, an antibody derivative can be an antibody that contains mutations resulting from affinity maturation processes that were applied to the reference antibody (or the nucleic acids encoding the reference antibody). Such mutations can result in antibodies with altered (e.g., improved) binding affinity, selectivity, and the like.

In some embodiments, the light chain complementary determining region CDR1 has the amino acid sequence KPXQXVXSXVX, as set forth in SEQ ID NO:1, wherein X at position 3 is S or V, wherein X at position 5 is N, R, or K, wherein X at position 7 is G, wherein X at position 9 is A, P, or R, and wherein X at position 11 is T, N, or A.

In some embodiments, the light chain complementary determining region CDR2 has the amino acid sequence XXXXRYX, as set forth in SEQ ID NO:2, wherein X at position 1 is S, wherein X at position 2 is A or T, wherein X at position 3 is S or T, wherein X at position 4 is N or R, and wherein X at position 7 is T or R.

In some embodiments, the light chain complementary determining region CDR3 has the amino acid sequence QQYXSXPYX, as set forth in SEQ ID NO:3, wherein X at position 4 is S, wherein X at position 6 is Y, K, R, or V, and wherein X at position 9 is T.

In some embodiments, the heavy chain complementary determining region CDR1 has the amino acid sequence GXXFXDXXXX, as set forth in SEQ ID NO:4, wherein X at position 2 is Y, wherein X at position 3 is T or R, wherein X at position 5 is T or H, wherein X at position 7 is S, wherein X at position 8 is T or R, wherein X at position 9 is M, and wherein X at position 10 is N.

In some embodiments, the heavy chain complementary determining region CDR2 has the amino acid sequence XIXPXXXXXXXNQXFXX, as set forth in SEQ ID NO:5, wherein X at position 1 is E, wherein X at position 3 is D, F, W, or A, wherein X at position 5 is N, S, K, W, or R, wherein X at position 6 is N or R, wherein X at position 7 is G, wherein X at position 8 is G, W, or R, wherein X at position 9 is T, wherein X at position 10 is N, wherein X at position 11 is Y, wherein X at position 14 is K, wherein X at position 16 is K, and wherein X at position 17 is G.

In some embodiments, the heavy chain complementary determining region CDR3 has the amino acid sequence ARXXWG, as set forth in SEQ ID NO:6, wherein X at position 3 is G, and wherein X at position 4 is V or S.

In some embodiments, the affinity reagent comprises 1, 2, 3, 4, 5, 6, 7, 8, 9, 10 or more mutations within the 6 CDR domains relative to the CDR domains of the 8A10 mAb, as described herein.

As indicated above, in some embodiments, the affinity reagent can be a monoclonal antibody, antibody fragment, or antibody derivative that is distinct from the 8A10 antibody. In some embodiments, the affinity reagent is a monoclonal antibody, antibody fragment, or antibody derivative that is distinct from an 8A10 antibody fragment. In this embodiment, the affinity reagent has an amino acid sequence that is distinct from any single contiguous subsequence of the 8A10 mAb.

In some embodiments, the affinity reagent is a monoclonal antibody, antibody fragment, or antibody derivative that comprises at least one amino acid difference in a CDR amino acid sequence from a corresponding CDR amino acid sequence of the 8A10 antibody as set forth in SEQ ID NOS:11, 31, 45, 58, 68, and 99.

In some embodiments, the affinity reagent is a monoclonal antibody, antibody fragment, or antibody derivative that comprises an amino acid sequence in a CDR selected from the following SEQ ID NOS:12-30, 32-44, 46-57, 59-67, 69-90, 92-98, and 100-103.

In some embodiments, the affinity reagent is a monoclonal antibody, antibody fragment, or antibody derivative that comprises one or more of the following amino acid substitutions N5R, N5K, A9R, T11N, and T11A with respect to SEQ ID NO:11, A2T, S3T, N4R, and T7R with respect to SEQ ID NO:31, Y6R, Y6K, and Y6V with respect to SEQ ID NO:45, T3R, T5H, and T8R with respect to SEQ ID NO:58, D3F, D3W, D3A, N6R, G8R and G8W with respect to SEQ ID NO:68. In a further embodiment, the monoclonal antibody, antibody fragment, or antibody derivative otherwise comprises the same CDR sequences of the 8A10 antibody as set forth in SEQ ID NOS:11, 31, 45, 58, 68, and 99.

Further embodiments of individual CDRs will now be described, which are based on results of a combinatorial library screen, as described in more detail below. It will be apparent that any particular embodiment of one specific CDR can be combined within the affinity reagent with any other particular embodiment of another specific CDR described herein, unless stated otherwise.

In some embodiments, the affinity reagent comprises a light chain CDR1 with an amino acid sequence selected from SEQ ID NOS:104-110.

In some embodiments, the affinity reagent comprises a light chain CDR2 with an amino acid sequence selected from SEQ ID NOS:111-117.

In some embodiments, the affinity reagent comprises a heavy chain CDR1 with an amino acid sequence selected from SEQ ID NOS:118-124.

In some embodiments, the affinity reagent comprises a heavy chain CDR2 with an amino acid sequence selected from SEQ ID NOS:125-132.

As generally indicated above, embodiments of the disclosed affinity reagents can be derived from the 8A10 antibody, and has at least some amino acid sequence difference from the 8A10 antibody. The affinity reagents can comprise one or more mutations, e.g., amino acid substitution deletion, addition, and/or substitution, relative to a CDR of the 8A10 mAb (as set forth in SEQ ID NOS:11, 31, 45, 58, 68, and 99), the framework (non-CDR) regions of the 8A10 variable light or heavy chain sequences, or other domains of the 8A10 mAb. The 8A10 variable light or heavy chain sequences are set forth herein as SEQ ID NOS:8 and 10, respectively. In some embodiments, the affinity reagent has a combined CDR sequence (considering all six CDR sequences) that is at least about 60, 65, 70, 75, 85, 90, 91, 92, 93, 94, 95, 96, 97, 98, 99 or 100% identical to the combined CDR sequence of the 8A10 antibody. In other embodiments, the affinity reagent has a variable light or heavy chain with an amino acid sequence that is at least about 60, 65, 70, 75, 85, 90, 91, 92, 93, 94, 95, 96, 97, 98, 99 or 100% to the sequence of the variable light or heavy chain sequences of the 8A10 antibody. It will be apparent to persons of ordinary skill that the affinity reagents are distinct from the 8A10 reference sequence and when one domain has perfect identify with the corresponding domain of the 8A10 reference sequence, then a difference is incorporated in a distinct domain.

As used herein, the term "percent identity" or "percent identical," when used in connection with a polypeptide, is defined as the percentage of amino acid residues in a polypeptide sequence that are identical with the amino acid sequence of a specified reference polypeptide (such as the amino acid sequence of SEQ ID NO:8), after aligning the sequences to achieve the maximum percent identity. Amino acid sequence identity can be determined according to any algorithm or technique known in the art.

As used herein, an "amino acid" refers to any of the 20 naturally occurring amino acids found in proteins, D-stereoisomers of the naturally occurring amino acids (e.g., D-threonine), unnatural amino acids, and chemically modified amino acids. Each of these types of amino acids is not mutually exclusive. α-Amino acids comprise a carbon atom to which is bonded an amino group, a carboxyl group, a hydrogen atom, and a distinctive group referred to as a "side chain." The side chains of naturally occurring amino acids are well-known in the art and include, for example, hydrogen (e.g., as in glycine), alkyl (e.g., as in alanine, valine, leucine, isoleucine, proline), substituted alkyl (e.g., as in threonine, serine, methionine, cysteine, aspartic acid, asparagine, glutamic acid, glutamine, arginine, and lysine), arylalkyl (e.g., as in phenylalanine and tryptophan), substituted arylalkyl (e.g., as in tyrosine), and heteroarylalkyl (e.g., as in histidine).

The following abbreviations are used for the 20 naturally occurring amino acids: alanine (Ala; A), asparagine (Asn; N), aspartic acid (Asp; D), arginine (Arg; R), cysteine (Cys; C), glutamic acid (Glu; E), glutamine (Gln; Q), glycine (Gly; G), histidine (His; H), isoleucine (Ile; I), leucine (Leu; L), lysine (Lys; K), methionine (Met; M), phenylalanine (Phe; F), proline (Pro; P), serine (Ser; S), threonine (Thr; T), tryptophan (Trp; W), tyrosine (Tyr; Y), and valine (Val; V).

Often, desirable amino acid substitutions relative to any portion of the reference 8A10 sequence (or 3C6 sequence, as described below) include a substitution with a similar amino acid as defined by a similar characteristic exhibited by the reference and substituted residues. Thus, in some embodiments, the variant affinity reagent comprises a conservative amino acid substitution as compared to the reference 8A10 sequence (or 3C6 sequence). Any substitution mutation is conservative in that it minimally disrupts the biochemical properties of the protein. Non-limiting examples of mutations that are introduced to substitute conservative amino acid residues include: positively-charged residues (e.g., H, K, and R) substituted with positively-charged residues; negatively-charged residues (e.g., D and E) substituted with negatively-charged residues; neutral polar residues (e.g., C, G, N, Q, S, T, and Y) substituted with neutral polar residues; and neutral non-polar residues (e.g., A, F, I, L, M, P, V, and W) substituted with neutral non-polar residues. Nonconservative substitutions can be made as well (e.g., proline for glycine).

Amino acids, and, more specifically, their side chains, can be characterized by their chemical characteristic(s). For example, amino acid side chains can be positively charged, negatively charged, or neutral. The pH of a solution affects the charged nature of certain side chains, as is known by those of skill in the art. Non-limiting examples of side chains that can be positively charged include histidine, arginine, and lysine. Non-limiting examples of side chains that can be negatively charged include aspartic acid and glutamic acid. Non-limiting examples of side chains that can be characterized as neutral include glycine, alanine, phenylalanine, valine, leucine, isoleucine, cysteine, asparagine, glutamine, serine, threonine, tyrosine, methionine, proline, and tryptophan.

Sterics of side chains can also be used to characterize an amino acid. Tables of atom diameters can assist one in determining whether one side chain is larger than another. Computer models may also help with this determination.

Amino acids can also be characterized by the polarity of their side chains. Polar side chains, which are typically more hydrophilic than non-polar side chains, include, for example, those of serine, threonine, tyrosine, cysteine, asparagine, and glutamine. Non-polar side chains, which are typically more hydrophobic than polar side chains, include, for example, those of glycine, alanine, valine, leucine, isoleucine, proline, methionine, phenylalanine, and tryptophan. One can determine polarity of a side chain using conventional techniques known in the art involving atom electronegativity determinations and three-dimensional structural assessments of side chains. One can also compare hydrophobicities/hydrophilicities of side chains using conventional techniques known in the art, such as comparing the octanol/water partition coefficient of each amino acid.

Alternatively, one may consider the hydropathic index of amino acids. Each amino acid has been assigned a hydropathic index on the basis of their hydrophobicity and/or charge characteristics, these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and/or arginine (−4.5). The importance of the hydropathic amino acid index in conferring interactive biological function on a protein is generally understood in the art. It is known that certain amino acids may be substituted for other amino acids having a similar hydropathic index and/or score and/or still retain a similar biological activity. In making changes based upon the hydropathic index, the substitution of amino acids whose hydropathic indices may be within ±2; within ±1, or within ±0.5.

It also is understood in the art that the substitution of like amino acids can be made effectively on the basis of hydrophilicity. As detailed in U.S. Pat. No. 4,554,101, incorporated herein by reference, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). In making changes based upon similar hydrophilicity values, it is contemplated that the substitution of amino acids whose hydrophilicity values may be within ±2, within ±1, or those within ±0.5.

3C6-derived Affinity Reagents

In one embodiment, the affinity reagent comprises one, two, three, four, five, or all six of the complementary determining regions contained in the 3C6 mAb. Specifically, the affinity reagent can comprise a CDRL1 with the amino acid sequence set forth in SEQ ID NO:143, a CDRL2 with the amino acid sequence set forth in SEQ ID NO:155, a CDRL3 with the amino acid sequence set forth in SEQ ID NO:160, a CDRH1 with the amino acid sequence set forth in SEQ ID NO:166, a CDRH2 with the amino acid sequence set forth in SEQ ID NO:172, and/or a CDRH3 with the amino acid sequence set forth in SEQ ID NO:184, and/or any combination thereof.

In a further embodiment, the affinity reagent comprises at least one amino acid difference relative to the amino acid sequence of 3C6 mAb. The sequence of the mAb is known and discernable by persons of ordinary skill in the art. In one embodiment, the affinity reagent comprises at least one amino acid difference in the framework (i.e., non-CDR) sequence of the variable region of the 3C6 heavy chain or light chain.

In another embodiment, the affinity reagent comprises one, two, three, four, five or all six CDRs corresponding to the CDRs of the 3C6 mAb, but also comprises at least one mutation, e.g., an amino acid difference, in any one or more of the six CDRs relative to 3C6 mAb, in any combination. Specifically, the affinity reagent can comprise at least one amino acid difference in at least one of the CDRs relative to: a CDRL1 with the amino acid sequence set forth in SEQ ID NO:143, a CDRL2 with the amino acid sequence set forth in SEQ ID NO:155, a CDRL3 with the amino acid sequence set forth in SEQ ID NO:160, a CDRH1 with the amino acid sequence set forth in SEQ ID NO:166, a CDRH2 with the amino acid sequence set forth in SEQ ID NO:172, and/or a CDRH3 with the amino acid sequence set forth in SEQ ID NO:184, and/or any combination thereof.

In one embodiment, the affinity reagent specifically comprises:

a light chain complementary determining region CDR1 with the amino acid sequence XSXQXLXHXXGNXYXH, as set forth in SEQ ID NO:133,
   wherein X at position 1 is R or H
   wherein X at position 3 is R, G, or N
   wherein X at position 5 is S, M, or G
   wherein X at position 7 is V or L
   wherein X at position 9 is S or I
   wherein X at position 10 is N or V
   wherein X at position 13 is T or S
   wherein X at position 15 is L or W;
a light chain complementary determining region CDR2 with the amino acid sequence XVSXXXS, as set forth in SEQ ID NO:134,
   wherein X at position 1 is K or N
   wherein X at position 4 is N or R
   wherein X at position 5 is R or L
   wherein X at position 6 is F or R;
a light chain complementary determining region CDR3 with the amino acid sequence SXSTHXXPX, as set forth in SEQ ID NO:135,
   wherein X at position 2 is Q or P
   wherein X at position 6 is V or G
   wherein X at position 7 is P or S
   wherein X at position 9 is T or R;
a heavy chain complementary determining region CDR1 with the amino acid sequence XDSITXGYXX, as set forth in SEQ ID NO:136,
   wherein X at position 1 is G or P
   wherein X at position 6 is S or I
   wherein X at position 9 is W or F
   wherein X at position 10 is N, R, or K;
a heavy chain complementary determining region CDR2 with the amino acid sequence XISYXGXXYXXPXLKX, as set forth in SEQ ID NO:137,
   wherein X at position 1 is Y or F
   wherein X at position 5 is S, R, or T
   wherein X at position 7 is S or D
   wherein X at position 8 is T or I
   wherein X at position 10 is Y or F
   wherein X at position 11 is N or K
   wherein X at position 13 is S or F
   wherein X at position 16 is S or N; and/or
a heavy chain complementary determining region CDR3 with the amino acid sequence XXXXY, as set forth in SEQ ID NO:138,
   wherein X at position 1 is G, A, or E
   wherein X at position 2 is D or W
   wherein X at position 3 is G or T
   wherein X at position 4 is A, D, G, or Q;
wherein the monoclonal antibody, antibody fragment, or antibody derivative binds to paclitaxel.

As indicated above, in some embodiments, the affinity reagent can be a monoclonal antibody, antibody fragment, or antibody derivative that is distinct from the 3C6 antibody. In some embodiments, the affinity reagent is a monoclonal antibody, antibody fragment, or antibody derivative that is distinct from a 3C6 antibody fragment. In this embodiment, the affinity reagent has an amino acid sequence that is distinct from any single contiguous subsequence of the 3C6 mAb.

In some embodiments, the affinity reagent is a monoclonal antibody, antibody fragment, or antibody derivative that comprises at least one amino acid difference in a CDR amino acid sequence from a corresponding CDR amino acid sequence of the 3C6 antibody as set forth in SEQ ID NOS:143, 155, 160, 166, 172, and 184.

In some embodiments, the affinity reagent is a monoclonal antibody, antibody fragment, or antibody derivative that comprises an amino acid sequence in a CDR selected from the following SEQ ID NOS:145-149, 151-154, 156-159, 161-165, 167-171. 174-178, 180-183, 185-189, and 246-248.

As generally indicated above, embodiments of the disclosed affinity reagents can be derived from the 3C6 antibody, and has at least some amino acid sequence difference from the 3C6 antibody. The affinity reagents can comprise one or more mutations, e.g., amino acid substitution deletion, addition, and/or substitution, relative to a CDR of the 3C6 mAb (as set forth in SEQ ID NOS: 143, 155, 160, 166, 172, and 184), the framework (non-CDR) regions of the 3C6 variable light or heavy chain sequences, or other domains of the 3C6 mAb. The 3C6 variable light and heavy chain sequences are set forth herein as SEQ ID NOS:140 and 142, respectively. In some embodiments, the affinity reagent has a combined CDR sequence (considering all six CDR sequences) that is at least about 60, 65, 70, 75, 85, 90, 91, 92, 93, 94, 95, 96, 97, 98, 99 or 100% identical to the combined CDR sequence of the 3C6 antibody. In other embodiments, the affinity reagent has a variable light or heavy chain with an amino acid sequence that is at least about 60, 65, 70, 75, 85, 90, 91, 92, 93, 94, 95, 96, 97, 98, 99 or 100% to the sequence of the variable light or heavy chain sequences of the 3C6 antibody.

In one embodiment, the affinity reagent derived from the 3C6 antibody is a monoclonal antibody, antibody fragment, or antibody derivative that comprises one or more of the following amino acid substitutions S5G with respect to SEQ ID NO:143 or SEQ ID NO:144 and A4Q and A4G with respect to SEQ ID NO:184.

Detection Methods

In another aspect, the disclosure provides a method for detecting paclitaxel or paclitaxel-based therapeutics in a sample. The method can be any immunoassay incorporating any of the paclitaxel-binding affinity reagents (e.g., antibody-based affinity reagents) described herein as a capture and/or detection reagent. Generally described, the method comprises contacting the sample with the paclitaxel-binding affinity reagent, detecting the formation of a complex between the affinity reagent and paclitaxel. The formation of a complex is indicative of the presence of paclitaxel in the sample.

In some embodiments, the sample is a biological sample, such as any biological fluid from a subject. Exemplary, non-limiting biological fluids include blood, plasma, serum, CSF, and the like. In some embodiments, the subject is a mammal, such as a human.

In some embodiments, the method also comprises quantifying the amount of paclitaxel or paclitaxel-based therapeutic in the sample. The quantification step comprises determining a level of complex formation between the paclitaxel-binding affinity reagent and paclitaxel, and comparing the level to level of complex formation obtained from one or more samples with known concentration or concentrations of paclitaxel. The samples with known concentrations of paclitaxel can be tested simultaneously or separately. It is preferred that such control samples utilize the same general protocol for purposes of standardization. In some cases, the amount of paclitaxel in the sample can be determined by comparing the observed level to a look up table that has been previously established.

Formats for applicable immunoassays are well-known and practiced in the art. Such assays for the detection and/or quantification of paclitaxel (or paclitaxel-based therapeutic) typically involve incubation of the sample that potentially contains paclitaxel with the affinity reagent, and detection via the formation of a complex between the affinity reagent and the paclitaxel. In various embodiments, either the components of the biological sample (including the target paclitaxel) or the affinity reagents are immobilized. In some embodiments, either the affinity reagent or some component of target paclitaxel is modified in a manner that it provides a detectable signal. Exemplary techniques include immunoassays, such as in situ hybridization, western blots, immunoprecipitation followed by SDS-PAGE electrophoresis, immunocytochemistry, ELISA, lateral flow assays, and the like, some of which are described in more detail below.

In competitive immunoassays, unlabeled analyte from a biological sample competes with a labeled version of the analyte, such as paclitaxel, for binding to an affinity reagent. The amount of labeled, unbound analyte is then measured. The more unlabeled analyte in the biological sample results in more labeled analyte that is displaced or competed off of the affinity reagent. Thus, the amount of labeled, unbound analyte that can be rinsed away is proportional to the amount of unlabeled analyte present in the biological sample. In a variation of this embodiment, the amount of labeled, bound analyte is measured, which is inversely proportional to the amount of unlabeled analyte present in the biological sample. In some embodiments, the affinity reagent is immobilized to facilitate the rinsing of the reagent, without losing the bound analytes.

In an exemplary non-competitive immunoassay, the biological sample can be brought in contact with, and immobilized onto, a solid phase support or a carrier, such as nitrocellulose, a plastic well, beads, magnetic particles, and the like. The solid phase support or carrier is capable of immobilizing cells, cell particles or soluble proteins. The solid phase support or carrier can then be washed with suitable buffers followed by treatment with the detectably labeled affinity reagent. The solid phase support or carrier can then be washed with the buffer a second time to remove unbound affinity reagent. The amount of bound label on solid phase support or carrier can then be detected by conventional means and is directly proportional to the amount of the target analyte, such as paclitaxel.

The term "solid phase support or carrier" is intended to mean any support or carrier capable of binding paclitaxel, or an affinity reagent that binds paclitaxel as described herein. Well-known supports or carriers include glass, polystyrene, polypropylene, polyethylene, dextran, nylon, amylases, natural and modified celluloses, polyacrylamides, gabbros, and magnetite, and the like. A substrate that acts as a carrier can be either soluble to some extent or insoluble for the purposes of the present disclosure. The support or carrier material can have virtually any possible structural configuration to conform to any assay format so long as the coupled target or affinity reagent is capable of binding to the corresponding affinity reagent or target molecule, respectively. Thus, the support or carrier configuration can be substantially spherical, as in a bead or magnetic particle, or cylindrical, as in the inside surface of a test tube, or well in a multi-well plate. Alternatively, the surface can be flat such as a sheet, test strip, etc., that would be appropriate in a lateral flow assay format. Those skilled in the art will recognize that many other suitable carriers are available for binding affinity reagents or the target paclitaxel (or paclitaxel-based therapeutic), or will be able to ascertain the same by use of routine experimentation.

In some embodiments, the paclitaxel or affinity reagent is immobilized directly to the solid phase support or carrier according to standard protocols in the art. In other embodiments, the paclitaxel or affinity reagent is indirectly immobilized on the solid phase support or carrier. For example, as described in more detail below, antibody based paclitaxel affinity reagents can be "captured" and immobilized to the solid support. Sometime it is preferable to utilize known blocking reagents to prevent spurious or elevated background binding. The support can be incorporated into a device that contains a matrix allowing migration of the biological sample, including the paclitaxel, past a region with immobilized affinity reagent. Detection of binding can be visualized as a result of any of the assay formats described herein, such as sandwich assays, competitive assays, and the like.

In some embodiments, the paclitaxel or the affinity reagent is conjugated onto a particle, such as a bead or magnetic particle, to facilitate collection or immobilization for further analysis.

Another exemplary non-competitive immunoassay format is referred to as a "sandwich" assay. In a sandwich assay, one affinity reagent is typically immobilized on a solid support or carrier. The biological sample is captured by the immobilized affinity reagent (thus, also referred to as the "capture reagent"). A second affinity reagent (also referred to as the "detection reagent") that is detectably labeled is also added. The capture affinity reagent can be the same as the detection affinity reagent. In other embodiments, the capture affinity reagent can be different from the detection affinity reagent.

As used herein, the term "labeled" can refer to direct labeling of the affinity reagent or paclitaxel via, e.g., coupling a detectable substance to the affinity reagent or paclitaxel. The term can also refer to indirect labeling of the affinity reagent by reactivity with another affinity reagent that is directly labeled. For example, an antibody affinity reagent specific for paclitaxel can itself be specifically bound by a second antibody that is detectably labeled.

In some embodiments, the detectable label comprises the coupling of an enzyme that is capable of producing a detectable signal when it acts upon a specific substrate. Some embodiments of enzyme-based immunoassays are referred to as enzyme linked immunosorbent assays (ELISAs) and are well-known in the art. See e.g., Voller, A., "The Enzyme Linked Immunosorbent Assay (ELISA)," 1978, Diagnostic Horizons 2:1-7, Microbiological Associates Quarterly Publication, Walkersville, Md.; Voller, A. et al., 1978, *J. Clin. Pathol.* 31:507-520; Butler, J. E., 1981, *Meth. Enzymol.* 73:482-523; Maggio, E. (ed.), 1980, Enzyme Immunoassay, CRC Press, Boca Raton, Fla.; Ishikawa, E. et al., (eds.), 1981, Enzyme Immunoassay, Kgaku Shoin, Tokyo). The enzyme which is bound to the antibody will react with an appropriate substrate, preferably a chromogenic substrate, in such a manner as to produce a chemical moiety which can be detected, for example, by spectrophotometric, fluorimetric or by visual means.

In other embodiments, the detectable label can be a fluorescent or chemiluminescent compound. A non-limiting, illustrative list of fluorescent compounds includes fluorescein isothiocyanate, rhodamine, phycoerythrin, phycocyanin, allophycocyanin, o-phthaldehyde and fluorescamine. Illustrative, non-limiting examples of particularly useful chemiluminescent labeling compounds are luminol, isoluminol, theromatic acridinium ester, imidazole, acridinium salt and oxalate ester.

In one particular embodiment, the method can be performed according to the general format described in WO 2015/154091, incorporated herein by reference in its entirety. Briefly described the biological sample, typically a liquid, is applied to the receiving zone of a lateral flow device. The detection affinity reagent, e.g., the paclitaxel binding affinity reagent as described herein, is deposited in a detection reagent zone that is in liquid communication with the sample receiving zone and downstream in flow direction from the sample receiving zone. In some embodiments, the paclitaxel binding affinity reagent is labeled with a detectable moiety or reporting group. In some embodiments, the paclitaxel binding affinity reagent has a $K_{on}$ from about $10^4$ to about $10^7$, and a $K_{off}$ from about $10^{-3}$ to about $10^{-7}$. The device also has a capture zone in liquid communication with the detection reagent zone and downstream in flow direction from the detection reagent zone. The capture zone comprises first and second capture reagents immobilized thereon. The first capture reagent is a paclitaxel material capable of binding the detection reagent (test line) and the second capture reagent is an antibody or similar reagent that can bind the detection reagent (control line). The first capture reagent is positioned at a first distance downstream in flow direction from the upstream end of the capture zone, the second capture reagent is positioned at a second distance downstream in flow direction from the upstream end of the capture zone, and wherein the second distance is greater than the first distance. Typically, the ratio of the first distance to the second distance is from about 0.0 to about 0.4, when the $K_{on}$ is greater than about $2.0 \times 10^5$ and the $K_{off}$ is less than about $1.0 \times 10^{-3}$, and the ratio of the first distance to the second distance is from about 0.2 to about 1.0, when the $K_{on}$ is greater than about $2.0 \times 10^4$ and the $K_{off}$ is less than about $2.0 \times 10^{-4}$.

In practice, the sample is permitted to flow from the sample receiving zone through the detection reagent zone to provide detection reagent with paclitaxel. Then the sample with the detection reagent and paclitaxel is permitted to flow through the capture zone, whereby the first capture reagent (test line) competes with the analyte (paclitaxel) for binding with the detection reagent, and whereby the second capture reagent (control line) binds excess detection reagent. The amount of detection reagent bound to the first capture reagent (test line) is observed relative to the second capture reagent (control line).

In one embodiment, the paclitaxel binding affinity reagent (i.e., detection reagent) is an 8A10-derived affinity reagent, as described herein. In another embodiment, the paclitaxel binding affinity reagent (i.e., detection reagent) is a 3C6-derived affinity reagent, as described herein.

Devices and Kits

In another aspect, the disclosure provides a device for detecting and/or quantifying paclitaxel in a sample. The device comprises one or more of the paclitaxel binding affinity reagents that are derived from 8A10 or 3C6 mAbs, as described herein. In some embodiments, the device further comprises a solid support.

In one embodiment, the device is a lateral flow device, comprising:

(a) a sample receiving zone for receiving a liquid sample;

(b) a detection reagent zone in liquid communication with the sample receiving zone and downstream in flow direction from the sample receiving zone, wherein the detection reagent zone comprises one or more paclitaxel binding affinity reagents that are derived from 8A10 or 3C6 mAbs deposited thereon, to serve as detection reagents;

(c) a capture zone in liquid communication with the detection reagent zone and downstream in flow direction from the detection reagent zone, wherein the capture zone comprises one or more capture reagents immobilized thereon; and (d) an absorbent zone in liquid communication with the capture zone and downstream in flow direction from the capture reagent zone.

The following describes the successful production of antibody-based affinity reagents derived from the 8A10 and 3C6 antibodies.

In order to effectively utilize antibody-based affinity reagents, such as in diagnostic and related applications, a dynamic binding/detection range should be achieved. Two key factors for optimization are the antibodies' specificity and affinity toward the targeted antigen. Specificity can be achieved by using monoclonal antibodies (mAbs), or antigen-binding derivatives thereof, that specifically bind to a single epitope of the targeted antigen in a highly homogeneous manner. This specificity also helps eliminate cross reactivity problems that may be of concern. In conjunction with specificity, monoclonal antibodies, or antigen-binding derivatives thereof, must have optimized and improved affinities toward the antigen in order to achieve a dynamic detection range in diagnostic tests, which can be achieved by the process of affinity maturation. The production of the reference 8A10 and 3C6 antibodies, and Fab derivatives thereof, incorporating one or more substitutions via an affinity maturation process is described below:

Antibody production and processing. Cells were grown in CCM1 (Hyclone) with 5-10% FBS and 1× Pen/Strep. Cells were split (1:4) once they reached densities of $>1\times10^6$ cells/mL. Cells were then frozen and stored in 2 separate liquid nitrogen cryogenic tanks as backups. Cells were cultured in roller bottles until a density of $1\times10^6$ cells/mL was reached. At that point, cultures were no longer fed and cell viability was monitored daily. Once cell viability decreased to <50%, cells were removed and the antibody-rich medium was harvested.

Affinity purification of antibody. Diafiltration was performed using PBS, pH 7.4 and the harvested antibody was concentrated 10-fold using a 50 Kd cut-off membrane. Mab Select (GE Healthcare, Pittsburgh, Pa.) was used for affinity purification. The hydrophilic, high-flow agarose bead, optimized for both capacity and throughput, and the oriented coupling of the rProtein A ligand, deliver a product pool that is high in purity and yield.

Purification run program:
Column: XK 16/40 (16 mm i.d., 20 cm bed height),
Sample: Clarified hybridoma spent media.
Loading Buffer A: 20 mM NaH2PO4, 0.15 M NaCl, pH 7.2.
Elution Buffer B: 0.1 M Na3-citrate, pH 3.6.

Characterization of Reference Antibody Binding

FIG. 1 illustrates results of a binding assay for the reference 8A10 mAb, as well as 3C6 mAb, demonstrating that the Kd values (approximately 10-20 nM for both antibodies) are comparable to ones previously reported. This confirms that the 8A10 mAbs bind directly to BSA-paclitaxel antigen with a sensitivity limit of about 100-200 ng/mL.

Figure 2:
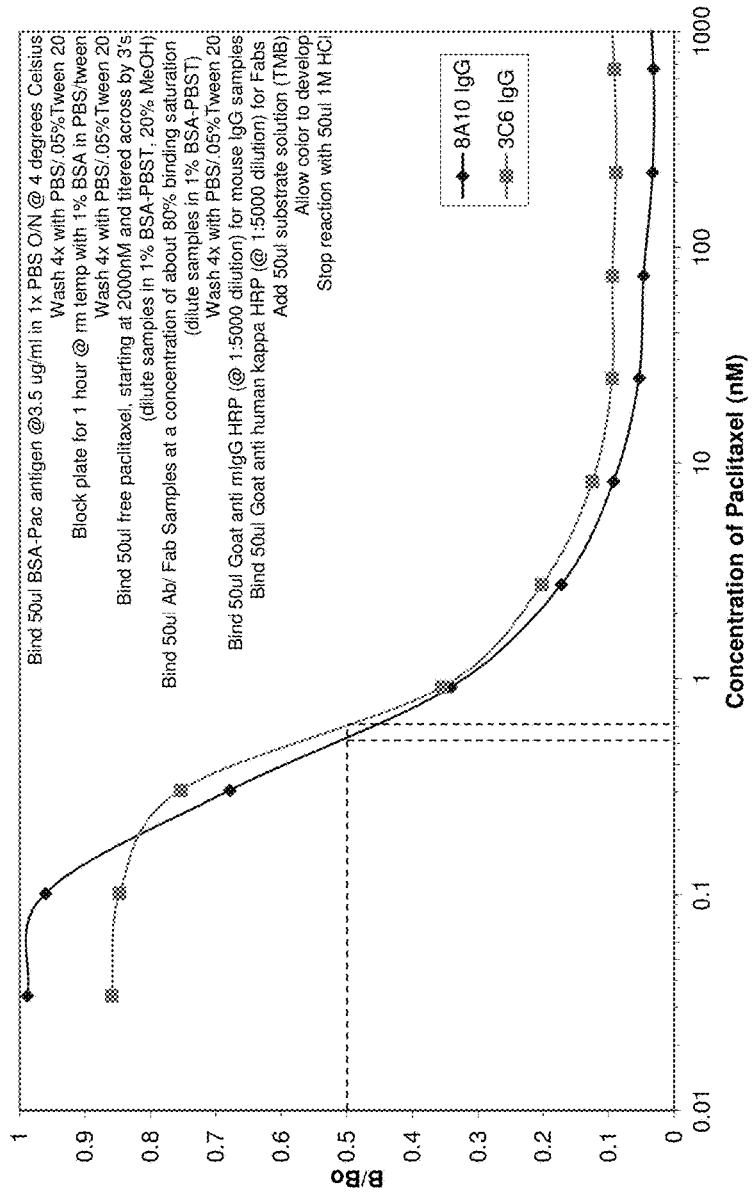
FIG. 2 is a graph illustrating the competitive inhibition ELISA to test binding of intact mAb 8A10 IgG (and 3C6) to a BSA-paclitaxel antigen in the presence of free paclitaxel.

As demonstrated, the 8A10 and 3C6 mAbs have high specificity and affinity to paclitaxel, which indicates that these each specifically bind to a single epitope of the targeted paclitaxel antigen in a highly homogeneous manner. This specificity helps eliminate cross reactivity problems in a detection assay. Furthermore, a competitive inhibition assay was performed to demonstrate the utility of the reference 8A10 and 3C6 mAbs in such a detection assay format. FIG. 2 illustrates the results of an ELISA where binding of 8A10 and 3C6 mAbs to labeled BSA-paclitaxel antigen decreased in presence of increasing free paclitaxel.

Overview of Illustrative Methods to Engineer/Optimize Antibody-Based Reagents

In conjunction with specificity, monoclonal antibody-based affinity reagents can also be optimized to provide improved affinities toward the antigen and/or to achieve enhanced properties, such as providing a dynamic detection range in diagnostic tests, which can be achieved by the process of affinity maturation. In order to obtain a collection of monoclonal antibody-based affinity reagents with improved affinities, the 8A10 and 3C6 mAbs were engineered to alter/improve their affinity for paclitaxel.

As an illustrative example, a simple, efficient, and robust approach for antibody optimization was performed, which included affinity maturation. An advantage of this approach is that it did not require detailed characterization of the structure of the antibody of the 8A10 and 3C6 mAbs. Generally, this approach involved: 1) characterizing the antibodies by sequencing antibodies produced from hybridoma cell lines, 2) constructing antibody libraries focused on CDR regions; 3) screening for beneficial mutations; and 4) combining beneficial mutations.

This procedure followed the iterative process seen in nature for functional improvement of proteins, including affinity maturation of antibodies. As demonstrated by the disclosed data, individual mutations can be combined to further improve an antibody's affinity. The distinguishing feature of the current approach for antibody optimization is that the size of the constructed libraries was extremely small. Typically, the libraries contained less than 400 variants, were constructed easily, and allowed various functional screening that may not otherwise be suitable to the affinity enrichment strategy.

The first step of this antibody engineering approach was to sequence the encoding variable regions of the 8A10 and 3C6 mAbs using the Rapid Amplification of cDNA Ends (RAGE) method. After the total RNA was extracted from hybridoma cells, a first-round RT-PCR followed by a second-round semi-nested PCR was performed. The PCR positive bands were cloned and then sequenced, followed by CDR analysis to identify light and heavy chain variable region sequences. The identified sequences were further confirmed by N-terminal amino acid sequencing.

Figure 4:
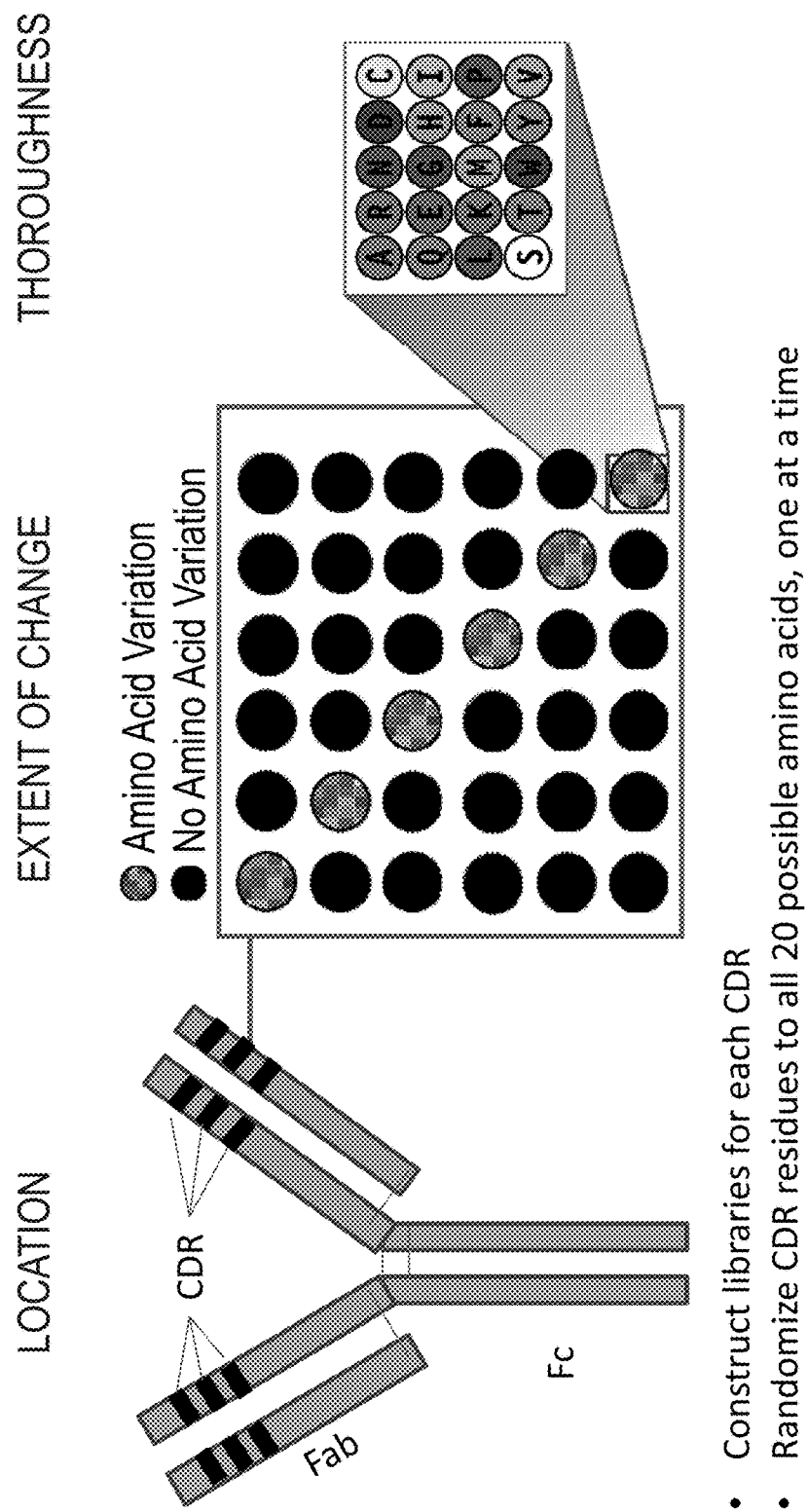
FIG. 4 is a cartoon illustration of a generalized antibody structure, including the heavy and light chains and their respective CDRs, as well as the approach for developing individual CDR libraries for each CDR that introduce all possible variations at each amino acid position, one position at a time.

Once the heavy and light chain variable sequences were identified, the next step was to construct focused antibody libraries. Because the antigen-binding site of an antibody is formed by six CDR loops, six CDR mutation libraries were constructed simultaneously. See, generally, FIG. 4. The codon-based mutagenesis approach with modification was used to synthesize the oligonucleotides, which introduced mutation at each amino acid position within each CDR. This approach permitted the synthesis of oligonucleotides that encoded single mutations.

The nucleic acid encoding the parental 8A10 and 3C6 mAbs was cloned onto an M13-based phage vector containing leader sequences and IgG1 CH1/kappa constant regions. Each CDR region was deleted respectively by hybridization mutagenesis. Then, synthesized oligonucleotides encoding the corresponding CDR region with mutations were annealed back to the vector for the construction of the CDR mutation library. Variants of Fab fragments were expressed by infecting *E. coli* XL-1 Blue with the phage library, and Fab fragments accumulated in the periplasmic space were subjected to screening. See, e.g., exemplary scheme in FIG. 5.

For affinity maturation, it was observed that single-mutation CDR libraries were preferable and sufficient because limited mutagenesis allowed the maintenance of the original binding domain, and results in a small-size library. Furthermore, this process mimicked in vivo affinity maturation of an antibody. Typically, a beneficial single mutation can improve the antibody's affinity 2-5 fold. As the size of each CDR library was normally less than 400 variants, the screening for beneficial mutations can easily be completed in a short time. The final step was to combine the beneficial single mutations from each CDR loop. Multiple-site hybridization mutagenesis was used for the construction of the combinatorial library. The accumulative effect can enhance the affinity dramatically.

Generally, affinity maturation of antibodies can be governed by two factors: association rate constant ($K_{on}$) and dissociation rate constant ($K_{off}$). The equilibrium dissociation constant ($K_d$) is calculated from $K_d = K_{off}/K_{on}$. In most instances of in vitro affinity maturation, the affinity is improved predominantly through the decrease of $K_{off}$.

The described affinity maturation procedure described herein served to can extend the application potential of the anti-paclitaxel 8A10 and 3C6 antibodies by producing high performance variant antibody-derivatives that can serve as affinity suitable for binding, detecting, and isolating paclitaxel. The combinatorial approach performed herein resulted in the in rapid antibody optimization, even in the absence of detailed structural information of the antibodies.

Methods and Results

Specific details of the above described strategy are described herein in more detail.

Step 1: Cloning and Expression of Anti-Paclitaxel 8A10 and 3C6 mAbs as a Fabs

A. Sequencing of Variable Regions of the 8A10 and 3C6 mAbs Produced from Hybridoma Cells i. Total RNA Extraction and mRNA Denaturation Total RNA was extracted from the hybridoma cells 8A10 and 3C6 using QIAGEN RNeasy Mini Kit. The mRNA mix (described below) was incubated at 72° C. for 3 min, then cooled down to 42° C. for 2 min. After cooling, the tube was spun briefly for 10 seconds at 14,000× g to collect the content at the bottom.

| mRNA Mix | |
|---|---|
| RNA template (0.2-0.4 ug) | 1-2.75 uL |
| 5'-RAGE primer A | 1 uL |
| RNase-free water | to 3.75 uL | ii. cDNA Synthesis and 5' RAGE Reaction cDNA synthesis and 5' RAGE reaction were performed as shown below.

| cDNA synthesis | | 5' RAGE reaction | |
|---|---|---|---|
| SMARTer II A oligo | 1 uL | 2X PCR mix | 10 uL |
| 5X First-strand buffer | 2 uL | cDNA | 1 uL |
| DTT (20 mM) | 1 uL | 10X Universal Primer mix | 2 uL |
| dNTP mix (10 mM) | 1 uL | Reverse primer | 1 uL |
| RNase inhibitor | 0.25 uL | RNase-free water | 6 uL |
| SMARTScribe RT | 1 uL | | |
| mRNA mix after dent | 3.75 uL | | |
| Total | 10 uL | | 20 uL | iii. Analysis of PCR by Agarose Gel Electrophoresis

Products of PCR amplification were electrophoresed on an agarose gel to confirm the presence of amplicons corresponding the light and heavy chain variable regions of the 8A10 and 3C6 mAbs.

iv. Cloning, sequencing and CDR analysis

The PCR positive bands were cloned into a vector and sequenced. Antibody sequence analysis identified one light chain and one heavy chain for 8A10.

The 8A10 hybridoma sequencing results are as follows:

The 8A10 Variable Light Chain nucleic acid sequence is set forth herein as SEQ ID NO:7 and is provided below:

```
                                        (SEQ ID NO: 7)
GAC ATT GTG ATG ACC CAG TCT CAA AAA TTC ATG
TCC ATA ACA CTA GGA GAG AGG GTC AGC ATC ACC TGC
AAG CCC AGT CAG AAT GTG GGT TCT GCT GTA ACC TGG
TGG CAA CAG AAA CCA GGA CAA TCT CCT AAA CTA CTG
ATT TAC TCA GCT TCC AAT CGG TAT ACT GGA GTC CCT
GAT CGC TTC ACA GGC AGT GGA TCT GGG ACA GAT TTC
ACT CTC ACC ATT AGT AAT GTG CAG TCT GAA GAC CTG
GCA GAT TAT TTC TGT CAA CAA TAT AGC AGC TAT CCG
TAC ACG TTC GGA GGG GGG ACC AAG CTG GAA ATA AAA
CG
```

The sequences encoding CDR 1, 2, and 3 domains are underlined.

The corresponding 8A10 Variable Light Chain amino acid sequence is set forth herein as SEQ ID NO:8 and is provided below:

```
                                        (SEQ ID NO: 8)
DIVMTQSQKFMSITLGERVSITCKPSQNVGSAVTWWQQKPGQSPKL
LIYSASNRYTGVPDRFTGSGSGTDFTLTISNVQSEDLADYFCQQYSSYPY
TFGGTKLEIK.
```

The CDR 1, 2, and 3 domains are underlined (i.e., CDRL1 is KPSQNVGSAVT, set forth as SEQ ID NO:11; CDRL2 is SASNRYT, set forth as SEQ ID NO:31; and CDRL3 is QQYSSYPYT, set forth as SEQ ID NO:45).

The 8A10 Variable Heavy Chain nucleic acid sequence is set forth herein as SEQ ID NO:9 and is provided below:

```
                                        (SEQ ID NO: 9)
GAG GTC CAG CTG CAA CAA TCT GGA CCT GAA CTG
GTG AAG CCT GGG GCT TCA GTG AAG ATT TCC TGT AAG
GCT TCT GGA TAC ACG TTC ACT GAC TCC ACC ATG AAC
TGG GTG AAG CAG AGC CAT GGA AAG AGC CTT GAG TGG
ATT GGA GAG ATT GAT CCT AAC AAT GGT GGT ACT AAC
TAC AAT CAG AAG TTC AAG GGC AAG GCC ACA TTG ACT
GTA GAC AAG TCC TCC AGC ACA GCC TAT ATG GAG CTC
CGC AGC CTG ACA TCT GAG GAC TCT GCA GTC TAT TAC
TGT GCA AGA GGG GTC TGG GGC CAA GGC ACC ACT CTC
ACA GTC TCC TCA.
```

The sequences encoding CDR 1, 2, and 3 domains are underlined.

The corresponding 8A10 Variable Heavy Chain amino acid sequence is set forth herein as SEQ ID NO:10 and is provided below:

```
                                        (SEQ ID NO: 10)
EVQLQQSGPELVKPGASVKISCKASGYTFTDSTMNWVKQSHGKSL
EWIGEIDPNNGGTNYNQKFKGKATLTVDKSSSTAYMELRSLTSEDSAVYY
CARGVWGQGTTLTVSS.
```

The CDR 1, 2, and 3 domains are underlined (i.e., CDRH1 is GYTFTDSTMN, set forth as SEQ ID NO:58; CDRH2 is EIDPNNGGTNYNQKFKG, set forth as SEQ ID NO:68; and CDRH3 is ARGVWG, set forth as SEQ ID NO:99).

Additionally, antibody sequence analysis identified one light chain and one heavy chain for 3C6.

The 3C6 hybridoma sequencing results are as follows:

The 3C6 Variable Light Chain nucleic acid sequence is set forth herein as SEQ ID NO:139 and is provided below:

```
                                       (SEQ ID NO: 139)
GAT GTT GTG ATG ACC CAA ACT CCA CTC TCC CTG
CCT GTC AGT CTG GGA GAT CAA GCC TCC ATC TCT TGC
AGA TCT CGT CAG AGC CTT GTA CAC AGT AAT GGA AAC
ACC TAT TTA CAT TGG TAC CTG CAG AAG CCA GGC CAG
```

```
TCT CCA AAG CTC CTG ATC TAC AAA GTT TCC AAC CGA

TTT TCT GGG GTC CCA GAC AGG TTC AGT GGT AGT GGA

TCA GGG ACA GAA TTC ACA CTC GAG ATC AGC AGA GTG

GAG GCT GAG GAT CTG GGA GTT TAT TTC TGC TCT CAA

AGT ACA CAT GTT CCT CCG ACG TTC GGT GGA GGC ACC

AAG CTG GAA ATC AAA C.
```

The sequences encoding the CDR regions are underlined.

The corresponding 3C6 Variable Light Chain amino acid sequence is SEQ ID NO: 140 and is provided below:

```
                                      (SEQ ID NO: 140)
     DVVMTQTPLSLPVSLGDQASISCRSRQSLVHSNGNTYLHWYLQKP

GQSPKLLIYKVSNRFSGVPDRFSGSGSGTEFTLEISRVEAEDLGVYFCSQ

STHVPPTFGGGTKLEIK.
```

The CDR 1, 2, and 3 domains are underlined (i.e., CDRL1 is RSRQSLVHSNGNTYLH, set forth herein as SEQ ID NO:142; CDRL2 is KVSNRFS, set forth herein as SEQ ID NO:155; and CDRL3 is SQSTHVPPT, set forth herein as SEQ ID NO:160).

The 3C6 Variable Heavy Chain nucleic acid sequence is SEQ ID NO: 141 and is provided below:

```
                                      (SEQ ID NO: 141)
      GAG GTG CAG CTT CAG GAG TCG GGA CCT AGT CTC

GTG AAA CCT TCT CAG ACT CTG TCC CTC ACC TGT TCT

GTC ACT GGC GAC TCC ATC ACC AGT GGT TAC TGG AAC

TGG ATC CGG AAA TTC CCA GGG AAT AGA CTT GAG TAC

ATG GGG TAC ATA AGC TAC AGT GGT AGC ACT TAC TAC

AAT CCG TCT CTC AAA AGT CGA ATC TCC ATC ACT CGA

GAC ACA TCC AAG AAC CAG TAC TAC CTA CAT TTG ACT

TCT GTG ACT ACT GAG GAC ACA GCC ACA TAT TAC TGT

GCC CAA GGG GAT GGC GCC TAC TGG GGC CAA GGC ACC

ACT CTC ACA GTC TCC TCA.
```

The sequences encoding the CDR regions are underlined.

The corresponding 3C6 Variable Heavy Chain amino acid sequence is SEQ ID NO: 142 and is provided below:

```
                                      (SEQ ID NO: 142)
     EVQLQESGPSLVKPSQTLSLTCSVTGDSITSGYWNWIRKFPGNRL

EYMGYISYSGSTYYNPSLKSRISITRDTSKNQYYLHLTSVTTEDTATYYC

AQGDGAYWGQGTTLTVSS.
```

The CDR 1, 2, and 3 domain regions are underlined (i.e., CDRH1 is GDSITSGYWN, set forth herein as SEQ ID NO:166; CDRH2 is YISYSGSTYYNPSLKS, set forth herein as SEQ ID NO:172; and CDRH3 is GDGAY, set forth herein as SEQ ID NO:184).

B. Cloning of Variable Regions of mAb into M13 Engineering Vector

The DNA coding for the VL, C kappa, and VH regions of the 8A10 and 3C6 mAbs were amplified with sequence specific primers using PCR. The resulting PCR product was gel-purified and restriction digested for specific sites within the M13-based phage vector under the control of lacZ promoter. The double-stranded DNA coding for the VL, C kappa, and VH regions of the 8A10 and 3C6 mAbs were ligated into the phage-based vector containing the gene for the constant region of the CH1 region of a human IgG1. The DNA was transformed into E. coli and the resulting plaques containing phage were examined in detail. Plaques were picked at random and the DNA was isolated and sequenced. The clones were confirmed to have the identical sequence for the VL, C kappa, and VH regions as that of 8A10 and 3C6 mAbs (not shown).

Figure 3:
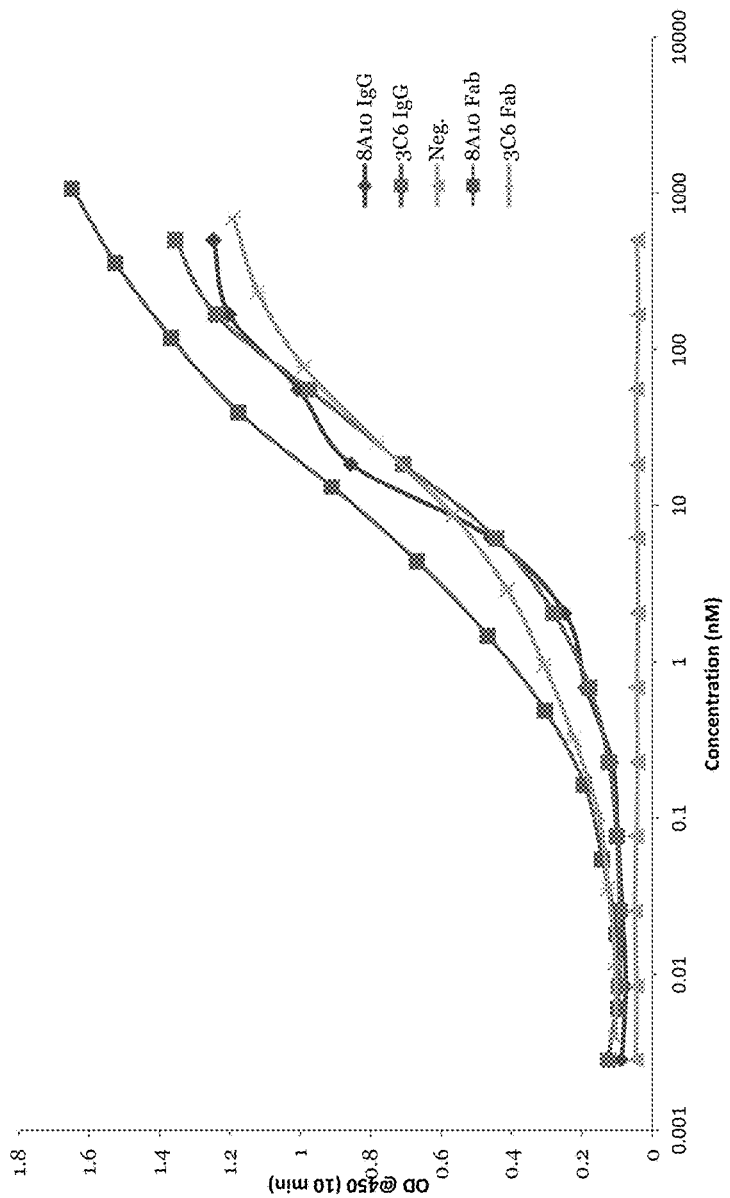
FIG. 3 is a graph illustrating the direct binding of intact mAb 8A10 IgG (and 3C6) to a BSA-paclitaxel antigen in the presence of free paclitaxel.

C. Demonstration of Paclitaxel Binding Activities of the Fabs Generated from the M13 Engineering Vector A clone 8A10_1 or clone 3C6_1 phage-infected culture of XL1-Blue E. coli (gram-negative) was grown while being induced with IPTG, was harvested via centrifugation and the periplasmic contents were released by osmotic shock (periprep). The released Fab products were isolated from the culture. The Fab concentration was quantified by ELISA. Antigen specific binding of the Fab was performed using paclitaxel ELISA together with intact IgGs. The Kd values of the intact 8A10 IgG (approximately 10-20 nM) were comparable to the Kd value of 8A10 Fab. See FIG. 3. These results suggest that the correct variable region sequences of the parental 8A10 and 3C6 mAbs exists in the present 8A10 and 3C6 Fabs and are correctly folded and expressed in the Fab format from the M13 engineering vector. It is noted that the 8A10 and Fab generally exhibited a comparable IC50 value in a competitive inhibition assay as the intact 8A10 IgG, although a slight shift was observed (not shown).

The Fab expressed sufficiently well in the periplasmic prep to demonstrate concentration-dependent binding to BSA-paclitaxel conjugate coated wells.

Step 2: Generation and Screening of Individual CDR Libraries

A. Generation of Individual CDR Libraries

For each CDR library construction, the parental CDR region was first deleted to avoid the domination of the library by the parental 8A10 or 3C6 clones. For example, in a successful single-site hybridization mutagenesis, the mutagenesis rate is usually between 50-80%. If the parental antibody is used as a template for the library construction, 20-50% of the library population will be parent clones, and this will increase the difficulty of screening.

Each CDR region was individually deleted by mutagenesis. After the clone containing the deletion was made, it was used as a template for the construction of its corresponding CDR library (see section D below). Altogether six CDR-deleted templates corresponding to each individual CDR library (for each of the 8A10 and 3C6 parental antibodies) were prepared.

To construct focused CDR libraries, the codon-based mutagenesis approach was used to synthesize oligonucleotides coding for CDR mutations. Libraries were constructed by annealing a pool of oligonucleotides, which fully randomized one position in the CDR domain while leaving the other residues unchanged. The resulting library had each position of the individual CDR changed to all possible amino acid alternatives, while preserving the remaining amino acids in the individual CDR and the remaining CDRS. Thus, in total, every single position across all the CDRs was mutated to every single alternative. See FIG. 4.

It will be understood that with modification, oligonucleotides can be synthesized to contain double, triple mutations, etc., respectively. The oligonucleotides are then used for library construction by hybridization mutagenesis. For affinity maturation, single-mutation libraries are sufficient. However, if significant characteristic change is desired for the antibody derivative, double and more mutations can be readily generated.

B. Biotinylation of BSA-paclitaxel

The BSA-paclitaxel conjugate was biotinylated for use in screening the CDR libraries. Ten micrograms of BSA-paclitaxel will be initially biotinylated at different molar excess concentrations of biotin: BSA-paclitaxel (20×, 60×, and 100×) to determine the optimal conditions for biotinylation. Binding ELISA assays were performed to evaluate the effect of the different biotinylation conditions on the Fab activity.

C. Optimization of Filter Lift Assays Utilizing Biotinylated BSA-Paclitaxel

Using the optimum concentration of biotinylated BSA-paclitaxel identified in the previous section, a test filter lift was performed to determine the optimal concentration of BSA-paclitaxel-biotin for screening the CDR libraries. An equal ratio of the parental 8A10 or 3C6 phage stock to the negative control Fab phage stock was mixed based on their pfu values. The resulting phage stock mixture was used to infect E. coli and produced approximately 500 plaques on an LB plate. A filter, coated with anti-human kappa, was used to capture Fabs secreted from the plaques by overlaying it on the plate. The filter with captured Fabs was incubated with varying levels of BSA-paclitaxel-biotin from 10 nM to 0.3 nM. Bound BSA-paclitaxel-biotin was detected with NeutrAvidin-AP. See, generally, FIG. 5. Positive clones were indicated with purple spots on the filters. It was determined that screening the libraries at 5 nm BSA-paclitaxel-biotin antigen was optimal for detecting positive (Fab binding) clones.

D. Incorporation of a Stop Codon Within Each CDR

The parental 8A10 or 3C6 clones were used as the template on which CDR libraries were be constructed (see section A above). For each CDR specific library, a stop codon was introduced into the CDR so that any clone that is not mutagenized would not express an Fab. Specifically, an oligonucleotide with a sequence that replaces one of the amino acids with the DNA sequence "TAAG" was used for each CDR to introduce the stop codon and put the following sequence out of frame. The parental 8A10 or 3C6 clones were mutagenized by annealing this oligonucleotide for each CDR individually and the mutagenized DNA was transformed into E. coli. The resulting plaques were isolated and sequenced. The resulting clones were used as the template for its respective CDR library.

E. Generation of Individual CDR Libraries

After isolation of the clone with the stop codon, libraries were constructed by annealing a pool of oligonucleotides, which fully randomized one position in the CDR while leaving the other residues unchanged. See FIG. 4. The resulting libraries had each position of the individual CDR changed to all possible amino acids one position at a time. The number of possible clones for each library was approximately 32 times the number of amino acid positions in the CDR. For example, a CDR with 10 positions had 320 possible clones. The mutagenized DNA was transformed into E. coli, and the resulting plaques were subjected to a filter lift where detection of the HA tag determined whether each clone had incorporated the mutagenic oligonucleotide or not. The HA positive clones were be randomly chosen, isolated, and sequenced.

F. Screening of Individual 8A10 CDR Libraries

Figure 5:
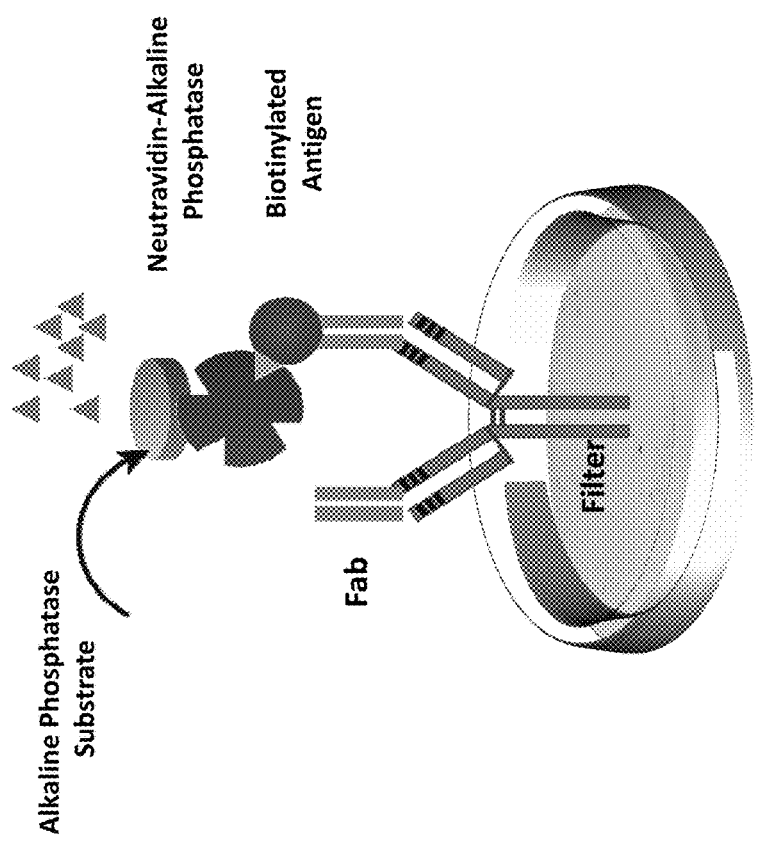
FIG. 5 is a cartoon illustration of the screen for Fabs produced in the individual CDR libraries that detect binding of the produced Fab variants to the antigen of interest (e.g., paclitaxel).
Figure 6A:
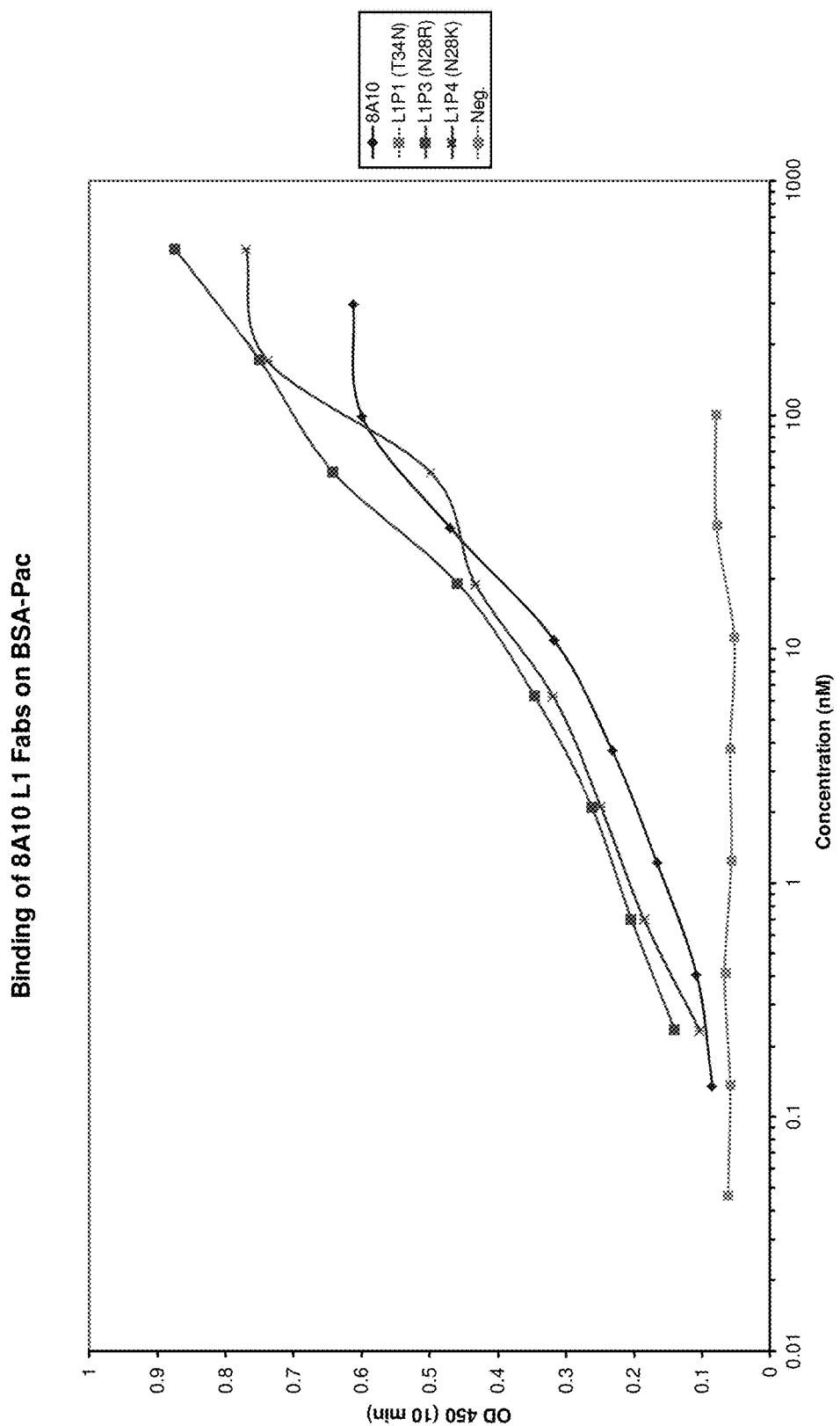
Figure 6B:
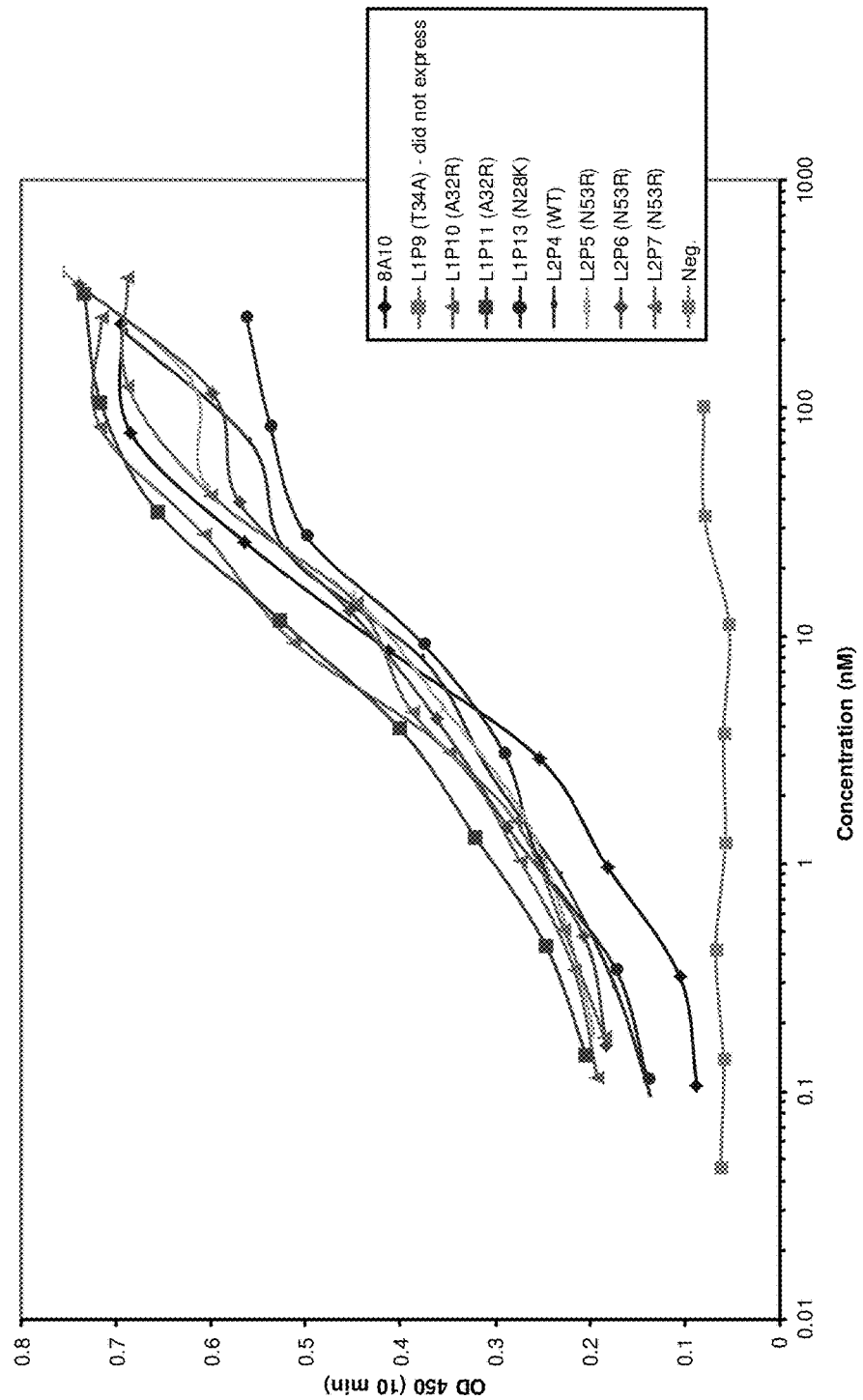
Figure 6C:
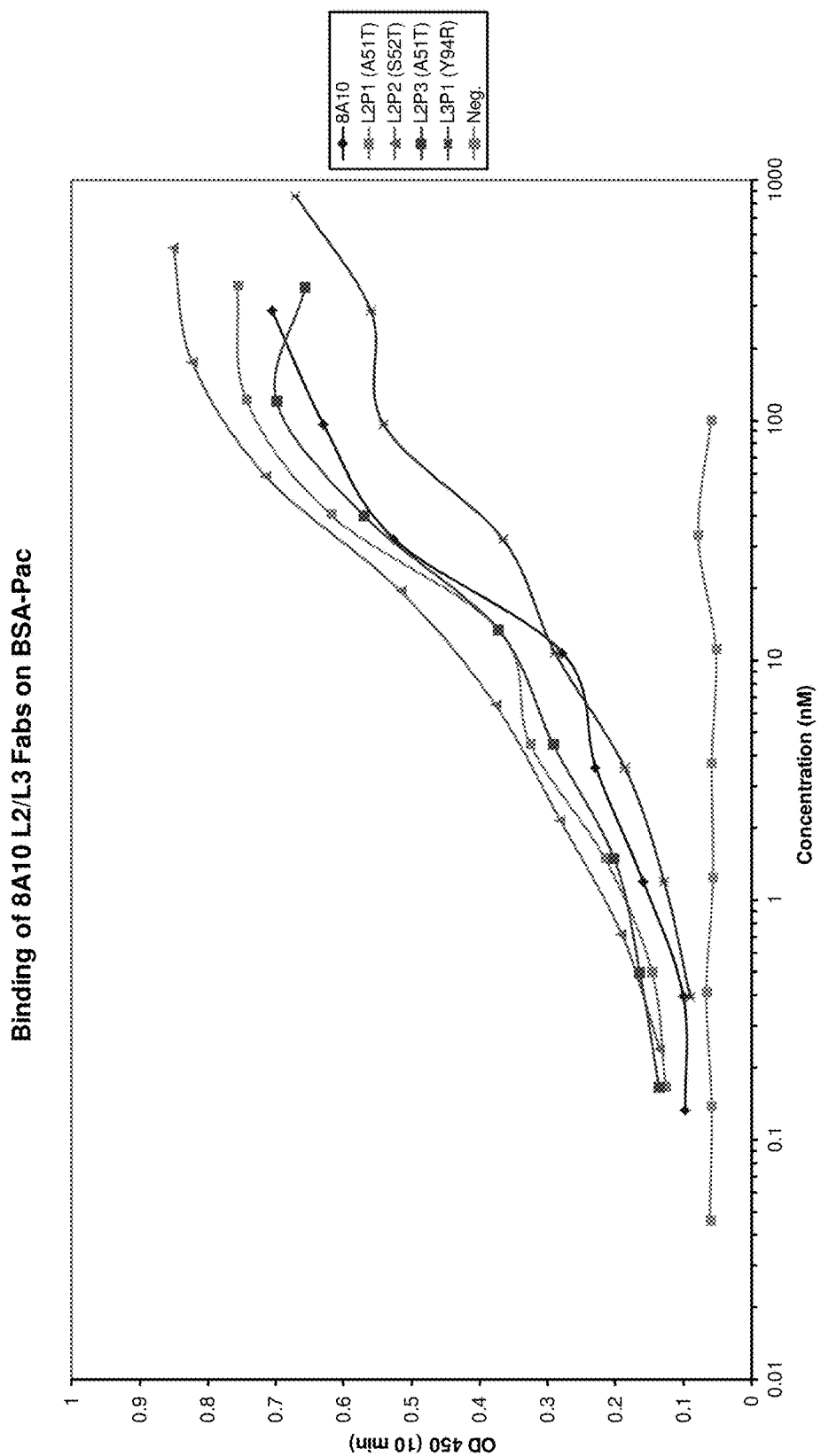
Figure 6F:
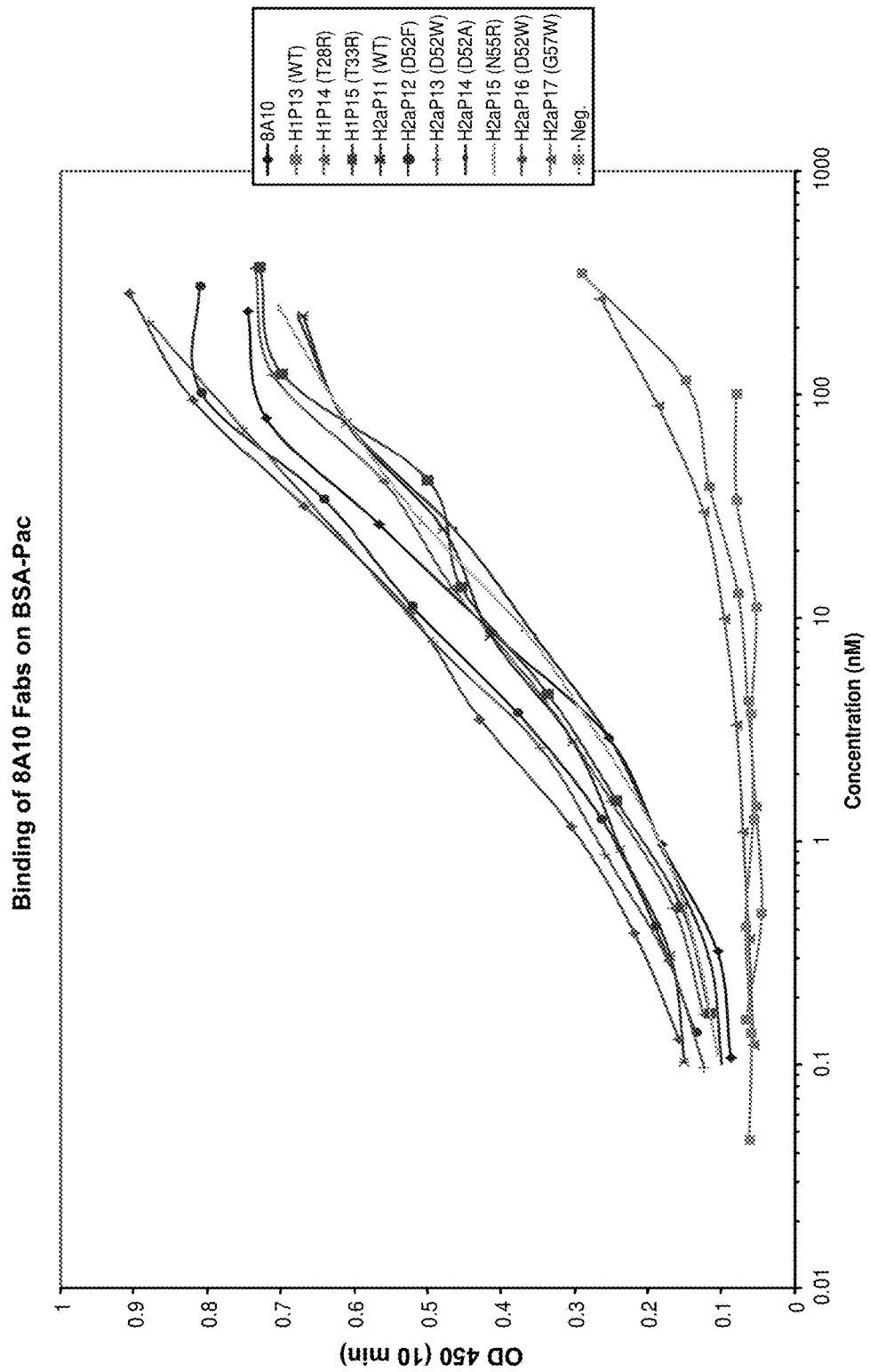
Figure 6G:
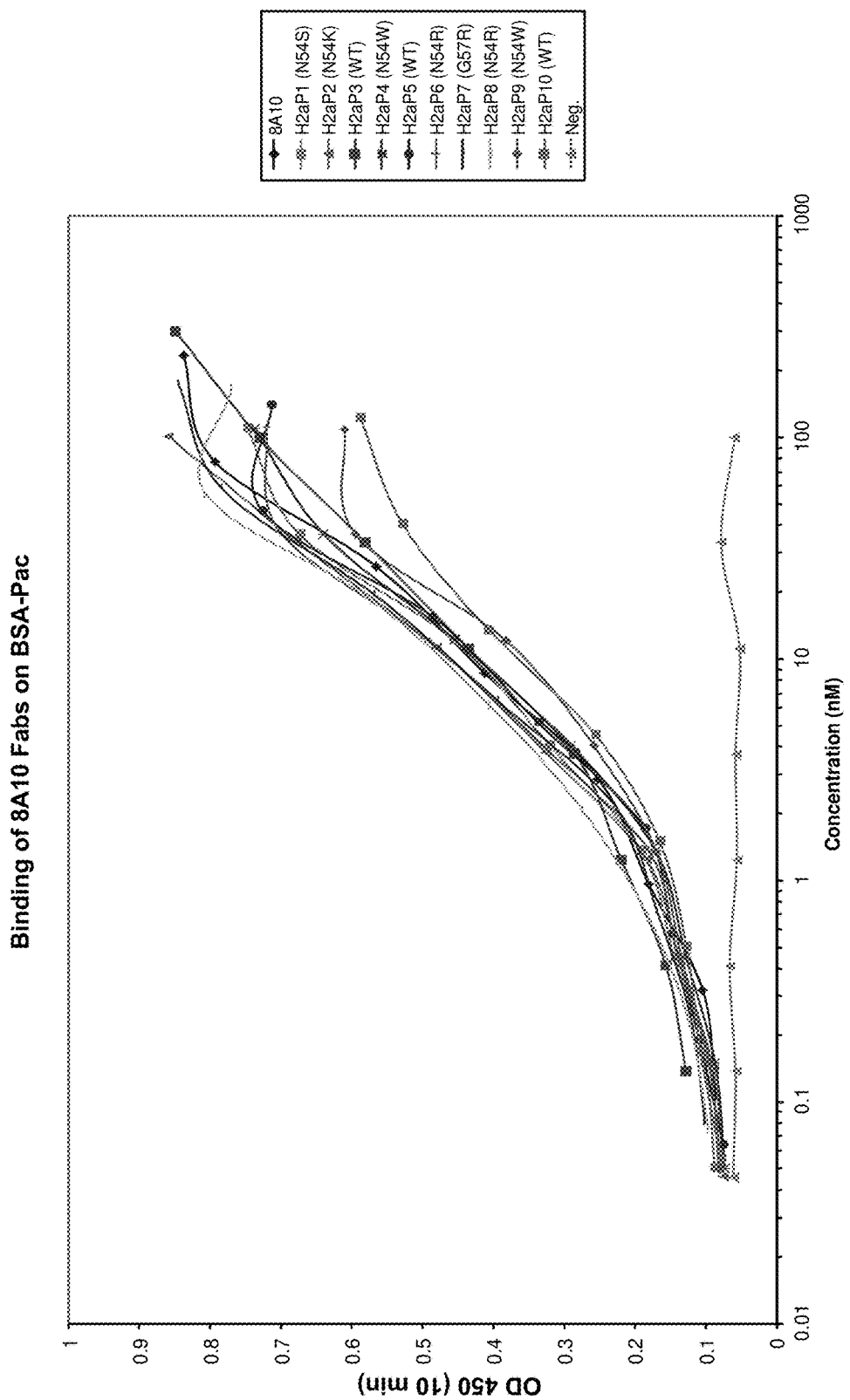

Individual CDR libraries (total 7 libraries because the 8A10 Heavy Chain CDR2 library was split in half due to CDR size) generated from the previous step were screened by plaque lift to look for increased affinity of the mutagenized Fabs to biotinylated BSA-paclitaxel (BSA-paclitaxel-biotin). The filter lift assay was designed to capture the same amount of Fab from each plaque. As illustrated in FIG. 5, a filter, coated with anti-human kappa, was used to capture Fabs secreted from the plaques by overlaying it on the plate. The filter with captured Fab was incubated with BSA-paclitaxel-biotin, using a concentration that was optimized as described above. Bound BSA-paclitaxel-biotin was detected with NeutrAvidin-AP. The purple spots on the filters indicated the positive clones. Each library was over-screened by at least five times the number of possible clones. That is, if the theoretical number of clones in a CDR library was 300, then >1500 clones were screened.

G. Verification of CDR Library "Hits" Using the Antigen-specific

Clones that were selected as "positive" hits were isolated, and the mutations were identified by sequencing the DNA. A phage-infected culture of E. coli of each selected CDR library "positive" hits was harvested and the periplasmic contents were released by osmotic shock (periprep). Cultures were also randomly samples to confirm that the technique indeed produced random variations in the targeted CDR domain. The sequences of select, representative hits from each 8A10 CDR library are set forth in Tables 1-6, where the consensus sequence is provided, as well as the position numbers with respect to the specific CDR domain as well as the entire disclosed variable domains of the light and heavy chains, respectively.

TABLE 1

Sequence variation in 8A10 CDRL1 region obtained from CDR mutation library
L1 LIBRARY

| | | Sequence | | | | | | | | | | | Notes |
|---|---|---|---|---|---|---|---|---|---|---|---|---|---|
| | | 24 | 25 | 26 | 27 | 28 | 29 | 30 | 31 | 32 | 33 | 34 | Position relative to SEQ ID NO: 8 |
| Type | Name of Clone | 1 | 2 | 3 | 4 | 5 | 6 | 7 | 8 | 9 | 10 | 11 | Consensus position |
| | Consensus | K | P | X | Q | X | V | X | S | X | V | X | SEQ ID NO: 1 |
| | 8A10 (Wild type) | K | P | S | Q | N | V | G | S | A | V | T | SEQ ID NO: 11 |
| RANDOM | L1R1 | K | P | S | Q | N | V | F | S | A | V | T | SEQ ID NO: 12 |
| | L1R2 | K | P | S | Q | T | V | G | S | A | V | T | SEQ ID NO: 13 |
| | L1R3 | K | P | V | Q | N | V | G | S | A | V | T | SEQ ID NO: 14 |
| | L1R4 | K | P | S | Q | N | V | F | S | A | V | T | SEQ ID NO: 15 |
| | L1R5 | K | P | S | Q | D | V | G | S | A | V | T | SEQ ID NO: 16 |
| | L1R6 | K | P | S | Q | N | V | F | S | A | V | T | SEQ ID NO: 17 |
| | L1R7 | K | P | S | Q | M | V | G | S | A | V | T | SEQ ID NO: 18 |
| POSITIVE | L1P1 | K | P | S | Q | N | V | G | S | P | V | N | SEQ ID NO: 19 |
| | L1P2 | K | P | S | Q | R | V | G | S | A | V | T | SEQ ID NO: 20 |
| | L1P3 | K | P | S | Q | R | V | G | S | A | V | T | SEQ ID NO: 21 |
| | L1P4 | K | P | S | Q | K | V | G | S | A | V | T | SEQ ID NO: 22 |
| | L1P5 | K | P | S | Q | N | V | G | S | A | V | T | Wild type, same as SEQ ID NO: 11 |
| | L1P6 | K | P | S | Q | N | V | G | S | R | V | T | SEQ ID NO: 23 |
| | L1P7 | K | P | S | Q | K | V | G | S | A | V | T | SEQ ID NO: 24 |
| | L1P8 | K | P | S | Q | N | V | G | S | A | V | N | SEQ ID NO: 25 |
| | L1P9 | K | P | S | Q | N | V | G | S | A | V | A | SEQ ID NO: 26 |
| | L1P10 | K | P | S | Q | N | V | G | S | R | V | T | SEQ ID NO: 27 |
| | L1P11 | K | P | S | Q | N | V | G | S | R | V | T | SEQ ID NO: 28 |
| | L1P12 | K | P | V | Q | N | V | G | S | A | V | T | SEQ ID NO: 29 |
| | L1P13 | K | P | S | Q | K | V | G | S | A | V | T | SEQ ID NO: 30 |
| | L1P14 | K | P | S | Q | N | V | G | S | A | V | T | Wild type, same as SEQ ID NO: 11 |

TABLE 2

Sequence variation in 8A10 CDRL2 region obtained from CDR mutation library
L2 LIBRARY

| | | Sequence | | | | | | | Notes |
|---|---|---|---|---|---|---|---|---|---|
| | | 50 | 51 | 52 | 53 | 54 | 55 | 56 | Position relative to SEQ ID NO: 8 |
| Type | Name of Clone | 1 | 2 | 3 | 4 | 5 | 6 | 7 | Consensus position |
| | Consensus | X | X | X | X | R | Y | T | SEQ ID NO: 2 |
| | 8A10 (Wild type) | S | A | S | N | R | Y | T | SEQ ID NO: 31 |
| RANDOM | L2R1 | S | A | T | N | R | Y | M | SEQ ID NO: 32 |
| | L2R2 | S | A | S | N | R | Y | T | SEQ ID NO: 33 |
| | L2R3 | Y | A | S | N | R | Y | T | SEQ ID NO: 34 |
| | L2R4 | S | H | S | N | R | Y | T | SEQ ID NO: 35 |
| POSITIVE | L2P1 | S | T | S | N | R | Y | T | SEQ ID NO: 36 |
| | L2P2 | S | A | T | N | R | Y | T | SEQ ID NO: 37 |
| | L2P3 | S | T | S | N | R | Y | T | SEQ ID NO: 38 |
| | L2P4 | S | A | S | N | R | Y | T | Wild type, same as SEQ ID NO: 31 |
| | L2P5 | S | A | S | R | R | Y | T | SEQ ID NO: 39 |
| | L2P6 | S | A | S | R | R | Y | T | SEQ ID NO: 40 |
| | L2P7 | S | A | S | R | R | Y | T | SEQ ID NO: 41 |
| | L2P8 | S | A | S | R | R | Y | T | SEQ ID NO: 42 |
| | L2P9 | S | A | S | N | R | Y | R | SEQ ID NO: 43 |
| | L2P10 | S | A | S | R | R | Y | T | SEQ ID NO: 44 |

TABLE 3

Sequence variation in 8A10 CDRL3 region obtained from CDR mutation library
L3 LIBRARY

| | | Sequence | | | | | | | | | Notes Position relative to SEQ ID NO: 8 |
|---|---|---|---|---|---|---|---|---|---|---|---|
| | | 89 | 90 | 91 | 92 | 93 | 94 | 95 | 96 | 97 | |
| Type | Name of clone | 1 | 2 | 3 | 4 | 5 | 6 | 7 | 8 | 9 | Consensus position |
| | Consensus | Q | Q | Y | X | S | X | P | Y | X | SEQ ID NO: 3 |
| | 8A10 (Wild type) | Q | Q | Y | S | S | Y | P | Y | T | SEQ ID NO: 45 |

TABLE 3-continued

Sequence variation in 8A10 CDRL3 region obtained from CDR mutation library
L3 LIBRARY

| Type | Name of clone | \multicolumn{9}{c}{Sequence} | Notes Position relative to SEQ ID NO: 8 Consensus position |
|---|---|---|---|---|---|---|---|---|---|---|---|
| | | 89<br>1 | 90<br>2 | 91<br>3 | 92<br>4 | 93<br>5 | 94<br>6 | 95<br>7 | 96<br>8 | 97<br>9 | |
| RANDOM | L3 R1 | Q | Q | Y | S | S | K | P | Y | T | SEQ ID NO: 46 |
| | L3 R2 | Q | Q | Y | P | S | Y | P | Y | T | SEQ ID NO: 47 |
| | L3 R3 | Q | Q | Y | S | S | Y | P | Y | R | SEQ ID NO: 48 |
| POSITIVE | L3 P1 | Q | Q | Y | S | S | R | P | Y | T | SEQ ID NO: 49 |
| | L3 P2 | Q | Q | Y | S | S | R | P | Y | T | SEQ ID NO: 50 |
| | L3 P3 | Q | Q | Y | S | S | R | P | Y | T | SEQ ID NO: 51 |
| | L3 P4 | Q | Q | Y | S | S | R | P | Y | T | SEQ ID NO: 52 |
| | L3 P5 | Q | Q | Y | S | S | K | P | Y | T | SEQ ID NO: 53 |
| | L3 P6 | Q | Q | Y | S | S | K | P | Y | T | SEQ ID NO: 54 |
| | L3 P7 | Q | Q | Y | S | S | V | P | Y | T | SEQ ID NO: 55 |
| | L3 P8 | Q | Q | Y | S | S | R | P | Y | T | SEQ ID NO: 56 |
| | L3 P9 | Q | Q | Y | S | S | K | P | Y | T | SEQ ID NO: 57 |

TABLE 4

Sequence variation in 8A10 CDRH1 region obtained from CDR mutation library
H1 LIBRARY

| Type | Name of Clone | \multicolumn{10}{c}{Sequence} | Notes Position relative to SEQ ID NO: 10 Consensus position |
|---|---|---|---|---|---|---|---|---|---|---|---|---|
| | | 26<br>1 | 27<br>2 | 28<br>3 | 29<br>4 | 30<br>5 | 31<br>6 | 32<br>7 | 33<br>8 | 34<br>9 | 35<br>10 | |
| | Consensus | G | X | X | F | X | D | X | X | X | X | SEQ ID NO: 4 |
| | 8A10 (Wild type) | G | Y | T | F | T | D | S | T | M | N | SEQ ID NO: 58 |
| RANDOM | H1 R1 | G | Y | T | F | T | D | S | T | M | N | Wild type, same as SEQ ID NO: 58 |
| | H1 R2 | G | Y | T | F | T | D | Y | T | M | N | SEQ ID NO: 59 |
| | H1 R3 | G | Y | T | F | T | D | S | T | M | N | Wild type, same as SEQ ID NO: 58 |
| | H1 R4 | G | S | T | F | T | D | S | T | M | N | SEQ ID NO: 60 |
| | H1 R5 | G | Y | T | F | T | D | S | T | T | N | SEQ ID NO: 61 |
| | H1 R6 | G | Y | T | F | S | D | S | T | M | N | SEQ ID NO: 62 |
| | H1 R7 | G | Y | T | F | T | D | S | Y | M | K | SEQ ID NO: 63 |

TABLE 4-continued

Sequence variation in 8A10 CDRH1 region obtained from CDR mutation library
H1 LIBRARY

| Type | Name of Clone | \multicolumn{10}{c}{Sequence} | Notes Position relative to SEQ ID NO: 10 Consensus position |
|---|---|---|---|---|---|---|---|---|---|---|---|---|
| | | 26 1 | 27 2 | 28 3 | 29 4 | 30 5 | 31 6 | 32 7 | 33 8 | 34 9 | 35 10 | |
| POSITIVE | H1 P1 | G | Y | T | F | T | D | S | T | M | N | Wild type; same as SEQ ID NO: 58 |
| | H1 P3 | G | Y | R | F | T | D | S | T | M | N | SEQ ID NO: 64 |
| | H1 P4 | G | Y | T | F | T | D | S | T | M | N | Wild type, same as SEQ ID NO: 58 |
| | H1 P6 | G | Y | T | F | H | D | S | T | M | N | SEQ ID NO: 65 |
| | H1 P7 | G | Y | T | F | T | D | S | T | M | N | Wild type, same as SEQ ID NO: 58 |
| | H1 P8 | G | Y | T | F | T | D | S | T | M | N | Wild type, same as SEQ ID NO: 58 |
| | H1 P9 | G | Y | T | F | T | D | S | T | M | N | Wild type, same as SEQ ID NO: 58 |
| | H1 P11 | G | Y | T | F | T | D | S | T | M | N | Wild type, same as SEQ ID NO: 58 |
| | H1 P12 | G | Y | T | F | T | D | S | T | M | N | Wild type, same as SEQ ID NO: 58 |
| | H1 P13 | G | Y | T | F | T | D | S | T | M | N | Wild type, same as SEQ ID NO: 58 |
| | H1 P14 | G | Y | R | F | T | D | S | T | M | N | SEQ ID NO: 66 |
| | H1 P15 | G | Y | T | F | T | D | S | R | M | N | SEQ ID NO: 67 |

TABLE 5

Sequence variation in the first half of 8A10 CDRH2 region obtained from CDR mutation library (part A)
H2A LIBRARY

| Type | Name of Clone | \multicolumn{8}{c}{Sequence} | Notes Position relative to SEQ ID NO: 10 Consensus position |
|---|---|---|---|---|---|---|---|---|---|---|
| | | 50 1 | 51 2 | 52 3 | 53 4 | 54 5 | 55 6 | 56 7 | 57 8 | |
| | Consensus | X | I | X | P | X | X | X | X | SEQ ID NO: 5 (first half) |
| | 8A10 (Wild type) | E | I | D | P | N | N | G | G | SEQ ID NO: 69 |
| RANDOM | H2A R1 | E | I | D | P | T | N | G | G | SEQ ID NO: 70 |
| | H2A R2 | E | I | D | P | N | N | L | G | SEQ ID NO: 71 |
| | H2A R3 | E | I | D | P | N | N | G | W | SEQ ID NO: 72 |
| | H2A R4 | E | I | D | P | N | S | G | G | SEQ ID NO: 73 |
| | H2A R5 | K | I | D | P | N | N | G | G | SEQ ID NO: 74 |
| | H2A R6 | E | I | D | P | M | N | G | G | SEQ ID NO: 75 |
| | H2A R7 | E | I | D | P | N | D | G | G | SEQ ID NO: 76 |

TABLE 5-continued

Sequence variation in the first half of 8A10 CDRH2 region obtained from CDR mutation library (part A)
H2A LIBRARY

| Type | Name of Clone | Sequence 50/1 | 51/2 | 52/3 | 53/4 | 54/5 | 55/6 | 56/7 | 57/8 | Notes — Position relative to SEQ ID NO: 10 Consensus position |
|---|---|---|---|---|---|---|---|---|---|---|
| POSITIVE | H2A P1 | E | I | D | P | S | N | G | G | SEQ ID NO: 77 |
|  | H2A P2 | E | I | D | P | K | N | G | G | SEQ ID NO: 78 |
|  | H2A P3 | E | I | D | P | N | N | G | G | Wild type, same as SEQ ID NO: 69 |
|  | H2A P4 | E | I | D | P | W | N | G | G | SEQ ID NO: 79 |
|  | H2A P5 | E | I | D | P | N | N | G | G | Wild type, same as SEQ ID NO: 69 |
|  | H2A P6 | E | I | D | P | R | N | G | G | SEQ ID NO: 80 |
|  | H2A P7 | E | I | D | P | N | N | G | R | SEQ ID NO: 81 |
|  | H2A P8 | E | I | D | P | R | N | G | G | SEQ ID NO: 82 |
|  | H2A P9 | E | I | D | P | W | N | G | G | SEQ ID NO: 83 |
|  | H2A P10 | E | I | D | P | N | N | G | G | Wild type, same as SEQ ID NO: 69 |
|  | H2A P11 | E | I | F | P | N | N | G | G | SEQ ID NO: 84 |
|  | H2A P12 | E | I | F | P | N | N | G | G | SEQ ID NO: 85 |
|  | H2A P13 | E | I | W | P | N | N | G | G | SEQ ID NO: 86 |
|  | H2A P14 | E | I | A | P | N | N | G | G | SEQ ID NO: 87 |
|  | H2A P15 | E | I | D | P | N | R | G | G | SEQ ID NO: 88 |
|  | H2A P16 | E | I | W | P | N | N | G | G | SEQ ID NO: 89 |
|  | H2A P17 | E | I | D | P | N | N | G | W | SEQ ID NO: 90 |

TABLE 6

Sequence variation in the second half of 8A10 CDRH2 region obtained from CDR mutation library (part B)
H2B LIBRARY

| Type | Name of Clone | Sequence 58/9 | 59/10 | 60/11 | 61/12 | 62/13 | 63/14 | 64/15 | 65/16 | 66/17 | Notes — Position relative to SEQ ID NO: 10 Consensus position |
|---|---|---|---|---|---|---|---|---|---|---|---|
|  | Consensus | X | X | X | N | Q | X | F | X | X | SEQ ID NO: 5 (second half) |
|  | 8A10 (Wild type) | T | N | Y | N | Q | K | F | K | G | SEQ ID NO: 91 |
| RANDOM | H2B R1 | T | N | Y | N | Q | K | F | K | G | Wild type, same as SEQ ID NO: 91 |
|  | H2B R2 | T | R | Y | N | Q | K | F | K | G | SEQ ID NO: 92 |

TABLE 6-continued

Sequence variation in the second half of 8A10 CDRH2 region obtained from CDR mutation library (part B)
H2B LIBRARY

| Type | Name of Clone | Sequence | | | | | | | | | Notes Position relative to SEQ ID NO: 10 Consensus position |
|---|---|---|---|---|---|---|---|---|---|---|---|
| | | 58 9 | 59 10 | 60 11 | 61 12 | 62 13 | 63 14 | 64 15 | 65 16 | 66 17 | |
| | H2B R3 | T | N | T | N | Q | K | F | K | G | SEQ ID NO: 93 |
| | H2B R4 | A | N | Y | N | Q | K | F | K | G | SEQ ID NO: 94 |
| | H2B R5 | T | N | Y | N | Q | K | F | S | G | SEQ ID NO: 95 |
| | H2B R6 | T | N | Y | N | Q | N | F | K | G | SEQ ID NO: 96 |
| | H2B R7 | T | A | Y | N | Q | K | F | K | G | SEQ ID NO: 97 |
| | H2B R8 | T | N | Y | N | Q | K | F | K | L | SEQ ID NO: 98 |
| POSITIVES | H2B P1 | T | N | Y | N | Q | K | F | K | G | Wild type, same as SEQ ID NO: 91 |
| | H2B P2 | T | N | Y | N | Q | K | F | K | G | Wild type, same as SEQ ID NO: 91 |
| | H2B P3 | T | N | Y | N | Q | K | F | K | G | Wild type, same as SEQ ID NO: 91 |

TABLE 7

Sequence variation in 8A10 CDRH3 region obtained from CDR mutation library
H3 LIBRARY

| Type | Name of Clone | Sequence | | | | | | Notes Position relative to SEQ ID NO: 10 Consensus position |
|---|---|---|---|---|---|---|---|---|
| | | 97 1 | 98 2 | 99 3 | 100 4 | 101 5 | 102 6 | |
| | Consensus | A | R | X | X | W | G | SEQ ID NO: 6 |
| | 8A10 (Wild type) | A | R | G | V | W | G | SEQ ID NO: 99 |
| RANDOM | H3 R1 | A | R | G | V | W | G | Wild type, same as SEQ ID NO: 99 |
| | H3 R2 | A | R | G | V | W | G | Wild type, same as SEQ ID NO: 99 |
| | H3 R3 | A | R | G | V | W | G | Wild type, same as SEQ ID NO: 99 |
| | H3 R4 | A | R | G | V | W | G | Wild type, same as SEQ ID NO: 99 |
| | H3 R5 | A | R | G | V | W | G | Wild type, same as SEQ ID NO: 99 |
| | H3 R6 | A | A | R | V | W | G | SEQ ID NO: 100 |
| | H3 R7 | A | R | G | V | W | G | Wild type, same as SEQ ID NO: 99 |
| | H3 R8 | A | R | G | V | W | G | Wild type, same as SEQ ID NO: 99 |
| | H3 R9 | A | R | G | P | W | G | SEQ ID NO: 101 |
| | H3 R10 | A | R | P | V | W | G | SEQ ID NO: 102 |

TABLE 7-continued

Sequence variation in 8A10 CDRH3 region obtained from CDR mutation library
H3 LIBRARY

| Type | Name of Clone | Sequence 97 1 | 98 2 | 99 3 | 100 4 | 101 5 | 102 6 | Notes Position relative to SEQ ID NO: 10 Consensus position |
|---|---|---|---|---|---|---|---|---|
| POSITIVES | H3 P1 | A | R | G | S | W | G | SEQ ID NO: 103 |
|  | H3 P2 | A | R | G | V | W | G | Wild type, same as SEQ ID NO: 99 |
|  | H3 P3 | A | R | G | V | W | G | Wild type, same as SEQ ID NO: 99 |

Fab concentration was quantified by Quant ELISA. Antigen-specific binding of the Fab variants was performed using the binding ELISA, described above. The binding of select 8A10-derived Fab variants are illustrated in FIGS. 6A-6G. As illustrated, the 8A10-derived Fab variants generally exhibited comparable and, at times, increased binding affinity for the paclitaxel antigen as compared to the reference 8A10 Fab.

Additionally, cultures sequences of the 3C6 CDR libraries were randomly selected and sequenced. The sequences are set forth in Tables 8-15.

TABLE 8

Sequence variation in the first half of 3C6 CDRL1 region obtained from CDR mutation library (part A)
L1A LIBRARY

| Type | Name of Clone | Sequence 24 1 | 25 2 | 26 3 | 27 4 | 28 5 | 29 6 | 30 7 | 31 8 | Notes Position relative to SEQ ID NO: 140 Consensus position |
|---|---|---|---|---|---|---|---|---|---|---|
|  | Consensus | X | S | X | Q | X | L | X | H | SEQ ID NO: 133 (first half) |
|  | 3C6 (Wild type) | R | S | R | Q | S | L | V | H | SEQ ID NO: 144 |
| RANDOM | L1A R1 | R | S | R | Q | M | L | V | H | SEQ ID NO: 145 |
|  | L1A R5 | R | S | R | Q | S | L | L | H | SEQ ID NO: 146 |
|  | L1A R2 | H | S | R | Q | S | L | V | H | SEQ ID NO: 147 |
|  | L1A R3 | R | S | G | Q | S | L | V | H | SEQ ID NO: 148 |
|  | L1A R4 | R | S | N | Q | S | L | V | H | SEQ ID NO: 149 |
| POSITIVE | L1A P1 | R | S | R | Q | G | L | V | H | SEQ ID NO: 246 |

TABLE 9

Sequence variation in the second half of 3C6 CDRL1 region obtained from CDR mutation library (part B)
L1B LIBRARY

| Name of Clone | Sequence 32 9 | 33 10 | 34 11 | 35 12 | 36 13 | 37 14 | 38 15 | 39 16 | Notes Position relative to SEQ ID NO: 140 Consensus position |
|---|---|---|---|---|---|---|---|---|---|
| Consensus | X | X | G | N | X | Y | X | H | SEQ ID NO: 133 (second half) |
| 3C6 (Wild type) | S | N | G | N | T | Y | L | H | SEQ ID NO: 150 |
| L1B R1 | S | N | G | N | S | Y | L | H | SEQ ID NO: 151 |

TABLE 9-continued

Sequence variation in the second half of 3C6 CDRL1 region obtained from CDR mutation library (part B)
L1B LIBRARY

| Name of Clone | Sequence | | | | | | | | Notes |
|---|---|---|---|---|---|---|---|---|---|
| | 32 9 | 33 10 | 34 11 | 35 12 | 36 13 | 37 14 | 38 15 | 39 16 | Position relative to SEQ ID NO: 140 Consensus position |
| L1B R2 | S | N | G | N | T | Y | L | H | Wild type, same as SEQ ID NO: 150 |
| L1B R3 | I | N | G | N | T | Y | L | H | SEQ ID NO: 152 |
| L1B R5 | S | N | G | N | T | Y | W | H | SEQ ID NO: 153 |
| L1B R4 | S | V | G | N | T | Y | L | H | SEQ ID NO: 154 |

TABLE 10

Sequence variation in 3C6 CDRL2 region obtained from CDR mutation library
L2 LIBRARY

| Name of Clone | Sequence | | | | | | | Notes |
|---|---|---|---|---|---|---|---|---|
| | 55 1 | 56 2 | 57 3 | 58 4 | 59 5 | 60 6 | 61 7 | Position relative to SEQ ID NO: 140 Consensus position |
| Consensus | X | V | S | X | X | X | S | SEQ ID NO: 134 |
| 3C6 (Wild type) | K | V | S | N | R | F | S | SEQ ID NO: 155 |
| L2 R3 | N | V | S | N | R | F | S | SEQ ID NO: 156 |
| L2 R1 | K | V | S | R | R | F | S | SEQ ID NO: 157 |
| L2 R2 | K | V | S | N | R | R | S | SEQ ID NO: 158 |
| L2 R4 | K | V | S | N | R | F | S | Wild type, same as SEQ ID NO: 155 |
| L2 R5 | K | V | S | N | L | F | S | SEQ ID NO: 159 |

TABLE 11

Sequence variation in 3C6 CDRL3 region obtained from CDR mutation library
L3 LIBRARY

| Name of Clone | Sequence | | | | | | | | | Notes |
|---|---|---|---|---|---|---|---|---|---|---|
| | 94 1 | 95 2 | 96 3 | 97 4 | 98 5 | 99 6 | 100 7 | 101 8 | 102 9 | Position relative to SEQ ID NO: 140 Consensus position |
| Consensus | S | X | S | T | H | X | X | P | X | SEQ ID NO: 135 |
| 3C6 (Wild type) | S | Q | S | T | H | V | P | P | T | SEQ ID NO: 160 |
| L3 R5 | S | Q | S | T | H | V | S | P | T | SEQ ID NO: 161 |
| L3 R2 | S | Q | S | T | H | V | P | P | R | SEQ ID NO: 162 |
| L3 R3 | S | Q | S | T | H | G | P | P | T | SEQ ID NO: 163 |
| L3 R4 | S | P | S | T | H | V | P | P | T | SEQ ID NO: 164 |
| L3 R1 | S | Q | S | T | H | V | S | P | T | SEQ ID NO: 165 |

TABLE 12

Sequence variation in 3C6 CDRH1 region obtained from CDR mutation library
H1 LIBRARY

| Name of Clone | \<th colspan="10">Sequence</th> | Notes |
|---|---|---|---|---|---|---|---|---|---|---|---|
| | 26 | 27 | 28 | 29 | 30 | 31 | 32 | 33 | 34 | 35 | Position relative to SEQ ID NO: 142 |
| | 1 | 2 | 3 | 4 | 5 | 6 | 7 | 8 | 9 | 10 | Consensus position |
| Consensus | X | D | S | I | T | X | G | Y | X | X | SEQ ID NO: 136 |
| 3C6 (Wild type) | G | D | S | I | T | S | G | Y | W | N | SEQ ID NO: 166 |
| H1 R1 | P | D | S | I | T | S | G | Y | W | N | SEQ ID NO: 167 |
| H1 R2 | G | D | S | I | T | S | G | Y | W | R | SEQ ID NO: 168 |
| H1 R3 | G | D | S | I | T | S | G | Y | F | N | SEQ ID NO: 169 |
| H1 R5 | G | D | S | I | T | S | G | Y | W | K | SEQ ID NO: 170 |
| H1 R4 | G | D | S | I | T | I | G | Y | W | N | SEQ ID NO: 171 |

TABLE 13

Sequence variation in the first half of 3C6 CDRH2 region obtained from CDR mutation library (part A)
H2A LIBRARY

| Name of Clone | | | | Sequence | | | | | Notes |
|---|---|---|---|---|---|---|---|---|---|
| | 50 | 51 | 52 | 53 | 54 | 55 | 56 | 57 | Position relative to SEQ ID NO: 142 |
| | 1 | 2 | 3 | 4 | 5 | 6 | 7 | 8 | Consensus position |
| Consensus | X | I | S | Y | X | G | X | X | SEQ ID NO: 137 (first half) |
| 3C6 (Wild type) | Y | I | S | Y | S | G | S | T | SEQ ID NO: 173 |
| H2A R5 | F | I | S | Y | S | G | S | T | SEQ ID NO: 174 |
| H2A R1 | Y | I | S | Y | R | G | S | T | SEQ ID NO: 175 |
| H2A R2 | Y | I | S | Y | S | G | S | I | SEQ ID NO: 176 |
| H2A R3 | Y | I | S | Y | S | G | D | T | SEQ ID NO: 177 |
| H2A R4 | Y | I | S | Y | T | G | S | T | SEQ ID NO: 178 |

TABLE 14

Sequence variation in the second half of 3C6 CDRH2 region obtained from CDR mutation library (part B)
H2B LIBRARY

| Name of Clone | | | | Sequence | | | | | Notes |
|---|---|---|---|---|---|---|---|---|---|
| | 58 | 59 | 60 | 61 | 62 | 63 | 64 | 65 | Position relative to SEQ ID NO: 142 |
| | 9 | 10 | 11 | 12 | 13 | 14 | 15 | 16 | Consensus position |
| Consensus | Y | X | X | P | X | L | K | X | SEQ ID NO: 137 (second half) |
| 3C6 (Wild type) | Y | Y | N | P | S | L | K | S | SEQ ID NO: 179 |
| H2B R1 | Y | Y | K | P | S | L | K | S | SEQ ID NO: 180 |
| H2B R2 | Y | Y | N | P | F | L | K | S | SEQ ID NO: 181 |
| H2B R3 | Y | F | N | P | S | L | K | S | SEQ ID NO: 182 |

TABLE 14-continued

Sequence variation in the second half of 3C6 CDRH2 region obtained from CDR mutation library (part B)
H2B LIBRARY

| Name of Clone | Sequence | | | | | | | | Notes |
|---|---|---|---|---|---|---|---|---|---|
| | 58<br>9 | 59<br>10 | 60<br>11 | 61<br>12 | 62<br>13 | 63<br>14 | 64<br>15 | 65<br>16 | Position relative to SEQ ID NO: 142<br>Consensus position |
| H2B R4 | Y | Y | N | P | S | L | K | N | SEQ ID NO: 183 |
| H2B R5 | Y | Y | N | P | S | L | K | S | Wild type, same as SEQ ID NO: 179 |

TABLE 15

Sequence variation in 3C6 CDRH3 region obtained from CDR mutation library
H3 LIBRARY

| Type | Name of Clone | Sequence | | | | | Notes |
|---|---|---|---|---|---|---|---|
| | | 98<br>1 | 99<br>2 | 100<br>3 | 101<br>4 | 102<br>5 | Position relative to SEQ ID NO: 142<br>Consensus position |
| | Consensus | X | X | X | X | Y | SEQ ID NO: 138 |
| | 3C6 (Wild type) | G | D | G | A | Y | SEQ ID NO: 184 |
| RANDOM | H3 R2 | G | D | G | D | Y | SEQ ID NO: 185 |
| | H3 R5 | G | D | T | A | Y | SEQ ID NO: 186 |
| | H3 R1 | A | D | G | A | Y | SEQ ID NO: 187 |
| | H3 R4 | G | W | G | A | Y | SEQ ID NO: 188 |
| | H3 R3 | E | D | G | A | Y | SEQ ID NO: 189 |
| POSITIVE | H3 P1 | G | D | G | Q | Y | SEQ ID NO: 247 |
| | H3 P5 | G | D | G | G | Y | SEQ ID NO: 248 |

Figure 9:
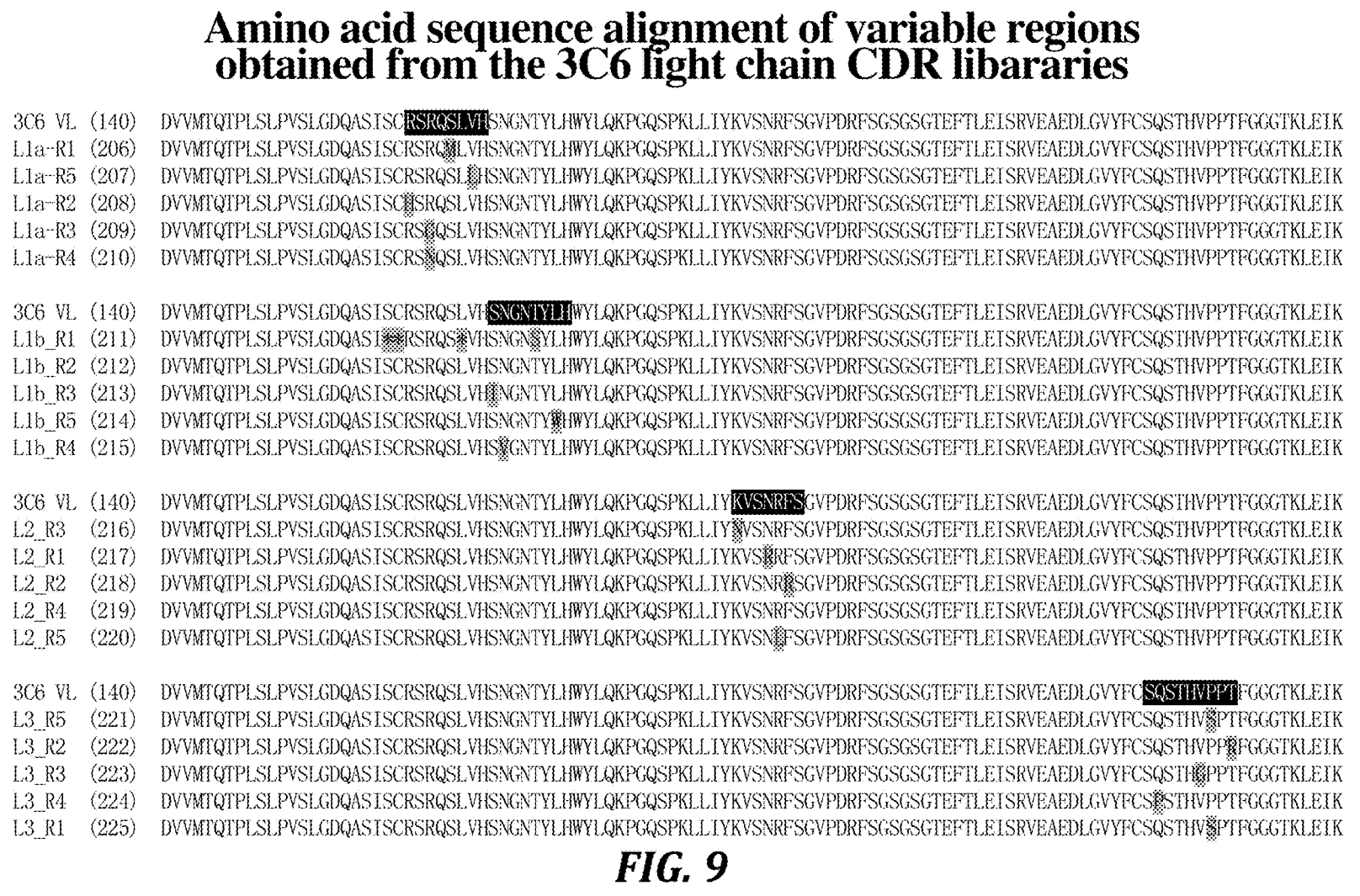
Figure 10:
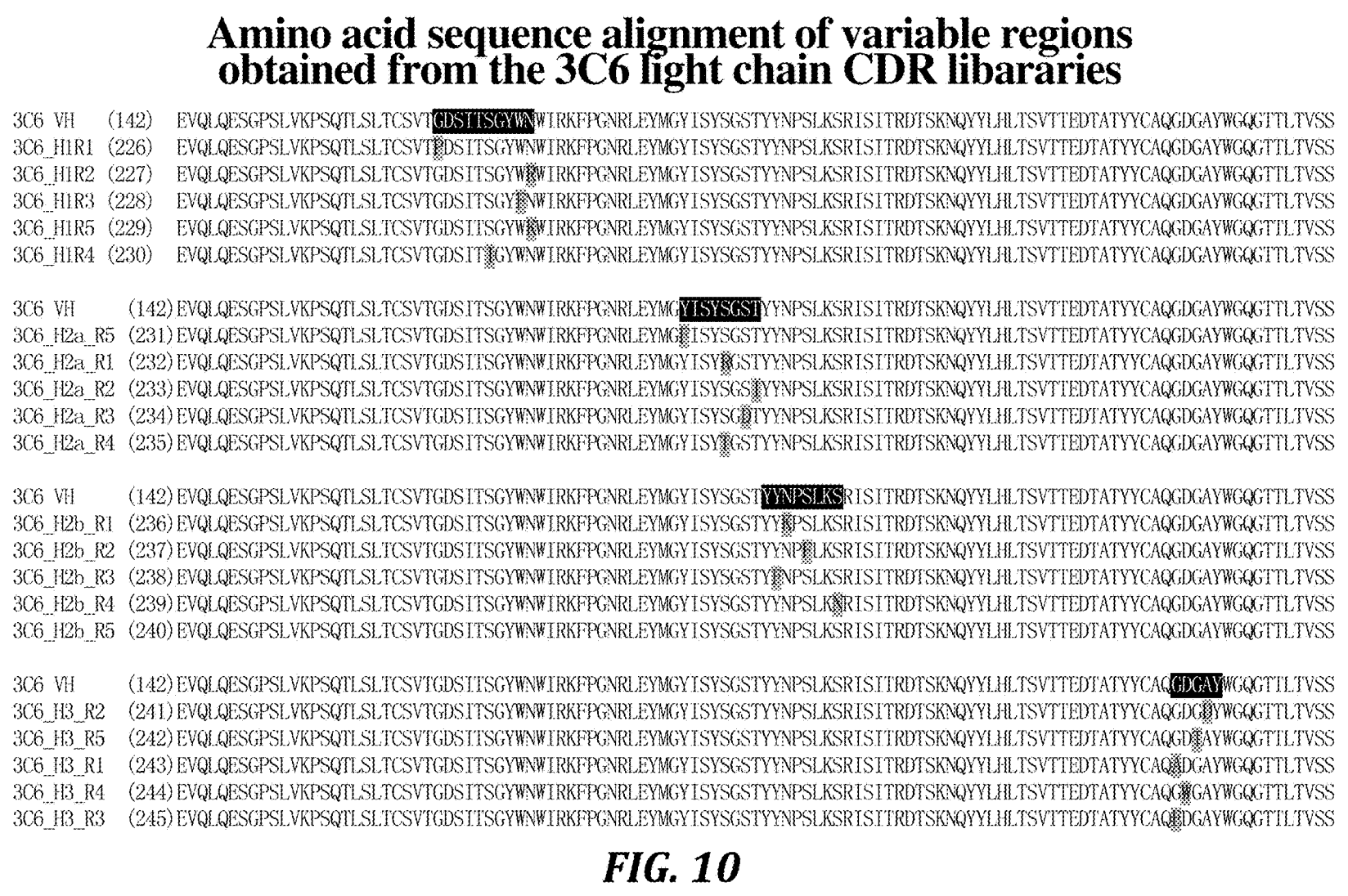
Figure 11A:
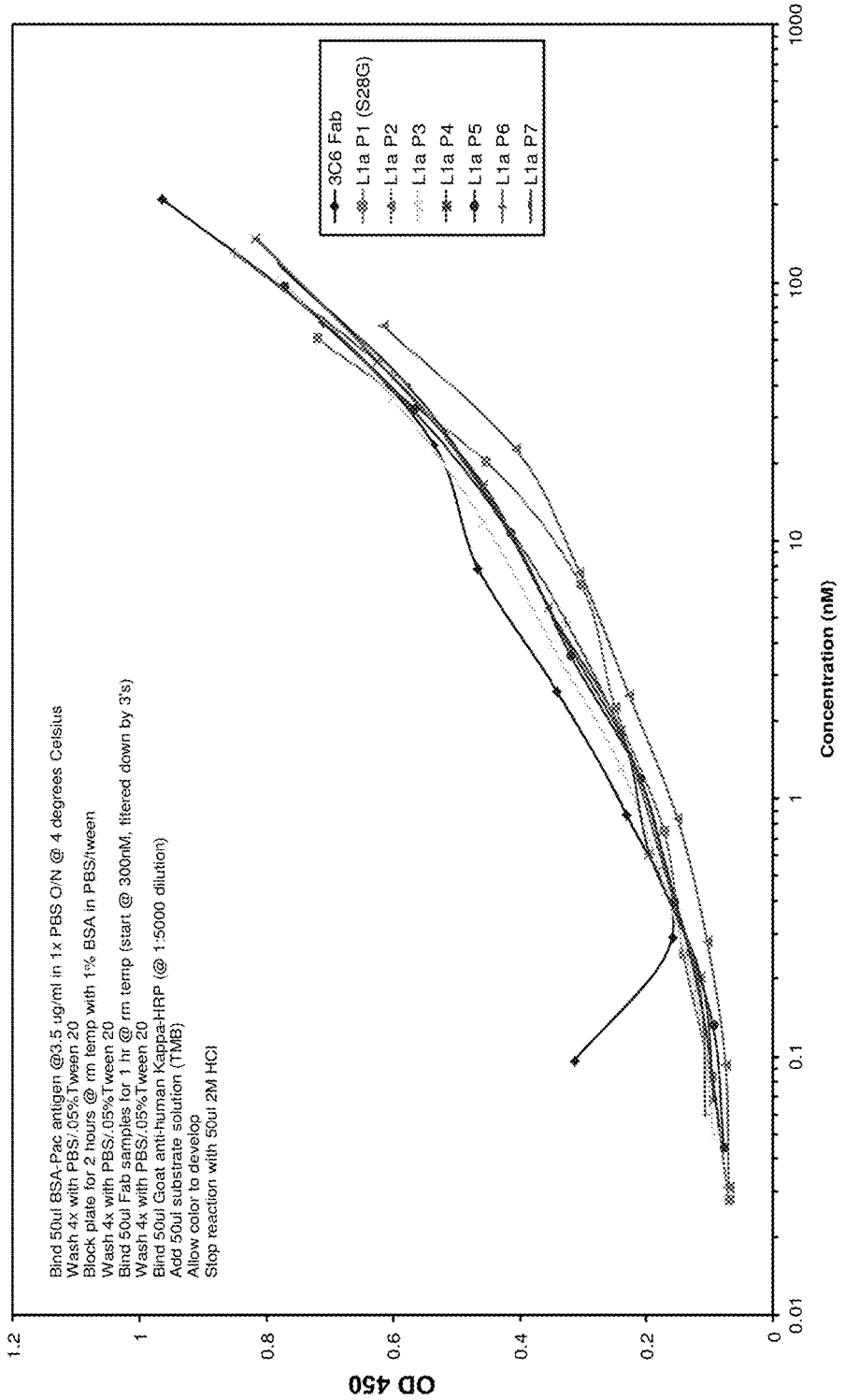
FIGS. 11A-11B graphically illustrate ELISA assays demonstrating the binding of select 3C6 derived Fab variants (i.e., with single CDR amino acid variations) to BSA-paclitaxel.
Figure 11B:
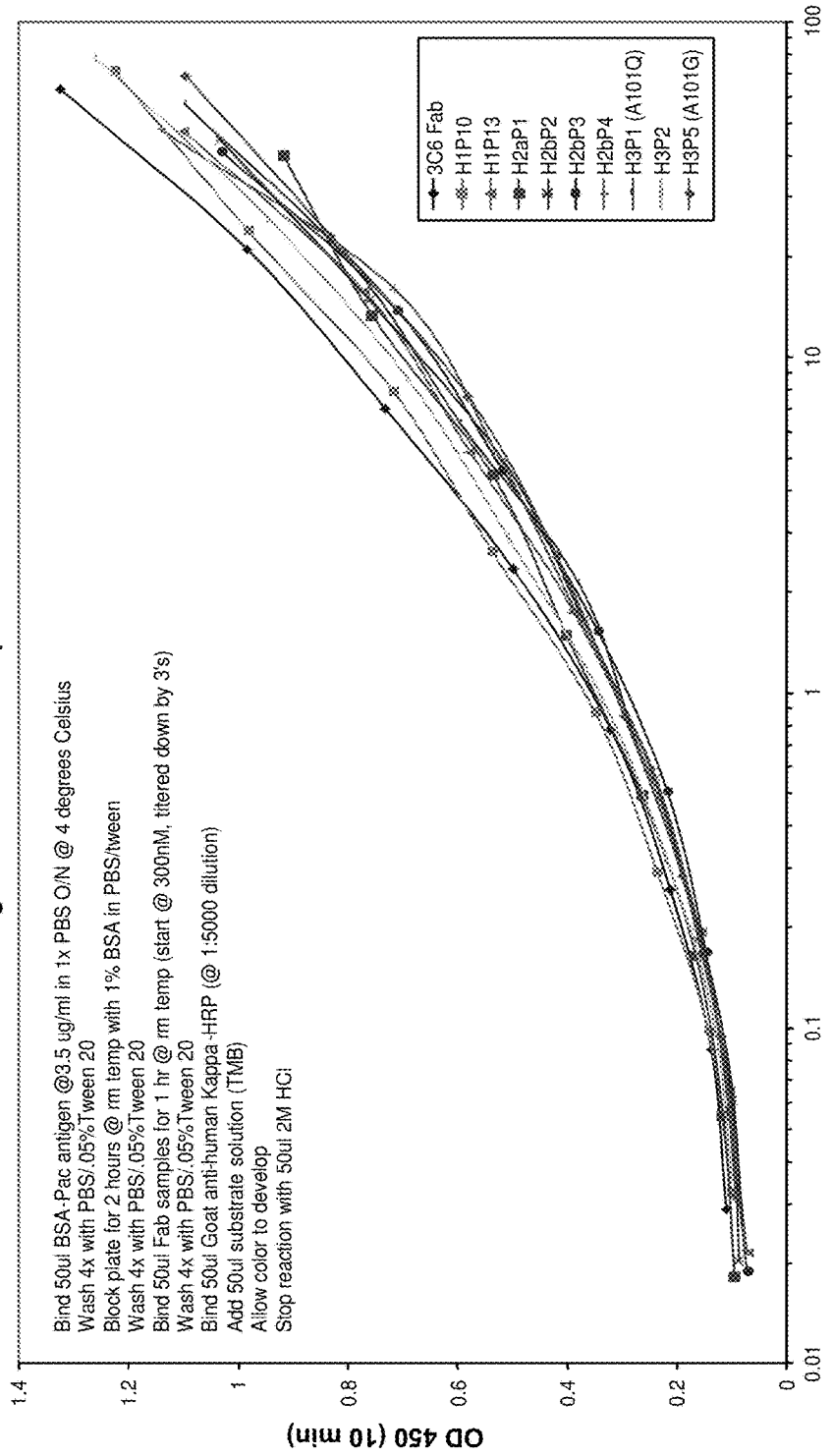

Sequence alignments of the entire variable light and heavy chains for the selected 3C6 variants are illustrated in FIGS. 9 and 10, respectively. The binding of select 3C6-derived Fab variants are illustrated in FIGS. 11A and 11B. As illustrated, the 3C6-derived Fab variants generally exhibited comparable and, at times, increased binding affinity for the paclitaxel antigen as compared to the reference 3C6 Fab.

These results demonstrate that the individual CDR variant libraries were able to produce single mutations at the targeted CDR domains to achieve production of alternative affinity reagents derived from reference antibodies, e.g., 8A10 and 3C6, which are known to bind to paclitaxel.

Step 3: 8A10 combinatorial library construction and screening

A. Generation of Combinatorial Library

An additional step in the affinity maturation process involved randomly combining the "best" mutations from the single CDR libraries. These CDR mutations generated from the single CDR library screenings were used as the basis for a "combinatorial" library. The CDR mutations that were included in the combinatorial library were chosen based on their activities in multiple antigen-specific ELISAs.

It is noted that another factor that can be considered in choosing the mutations for such a combinatorial library is the replacement of potentially problematic residues such as Asn, Met, and Cys. Specifically, an Asn residue can be potentially subjected to deamidation, particularly when it is followed by a small R-group such as Gly or His. Such deamidation can negatively impact the affinity of the antibody. The Met residue can cause unnecessary oxidation event which may potentially decrease the activity of the antibody depending on the location of modification. Also, the Cys residue may be problematic by forming unwanted disulfide bond with another Cys residue, resulting in the change of antibody structure.

The present combinatorial library was generated on a background of Clone 8A10_1, the parental Fab clone. The chosen CDR mutations were randomly introduced using oligonucleotide mutagenesis. The size of combinatorial library was controlled to generate about 1,000 or fewer mutants to facilitate the screening process.

B. Screening of Combinatorial Library

The combinatorial library was screened extensively (>5 times of potential variants) by a filter lift assay with varying conditions, as generally described above for the individual CDR variant libraries. Again, the concentration of biotinylated BSA-paclitaxel and washing time was varied to optimize the screen. The positive clones were isolated and their sequences were determined by DNA sequencing. In this particular screen, only mutations in the CDR 1 and CDR 2 domains of each of the light and heavy chains were selected for screening.

The sequences of select, representative hits from the combinatorial library are set forth in Tables 16 and 17 for the light and heavy chain sequences, respectively. The position numbers are provided with respect to the entire disclosed variable domains of the light and heavy chains, respectively.

TABLE 8

Light chain sequence variation in 8A10 combinatorial library
8A10 combinatorial library

| Position relative to SEQ ID NO: 8 Fab | Light Chain CDR | | | | | | | | | | | | | | | | | | | |
|---|---|---|---|---|---|---|---|---|---|---|---|---|---|---|---|---|---|---|---|---|
| | L1 | | | | | | | | | | | | L2 | | | | | | | |
| | 24 | 25 | 26 | 27 | 28 | 29 | 30 | 31 | 32 | 33 | 34 | Seq ID NO: | 50 | 51 | 52 | 53 | 54 | 55 | 56 | Seq ID NO: |
| Wild Type | K | P | S | Q | N | V | G | S | A | V | T | 11 | S | A | S | N | R | Y | T | 31 |
| CP2 | K | P | S | Q | K | V | G | S | R | V | T | 104 | S | A | I | N | R | Y | T | 111 |
| CP3 | K | P | S | Q | R | V | G | S | R | V | T | 105 | S | T | I | N | R | Y | T | 112 |
| CP4 | K | P | S | Q | K | V | G | S | A | V | T | 106 | S | T | N | N | R | Y | T | 113 |
| CP5 | K | P | S | Q | N | V | G | S | A | V | T | 11 | S | A | S | N | R | Y | T | 31 |
| CP6 | K | P | S | Q | K | V | G | S | A | V | T | 107 | S | T | I | R | R | Y | T | 114 |
| CP7 | K | P | S | Q | K | V | G | S | R | V | T | 108 | S | A | N | N | R | Y | T | 115 |
| CP8 | K | P | S | Q | K | V | G | S | R | V | T | 109 | S | T | N | N | R | Y | T | 116 |
| CP9 | K | P | S | Q | K | V | G | S | A | V | T | 110 | S | A | N | R | R | Y | T | 117 |

TABLE 9

Heavy chain sequence variation in 8A10 combinatorial library

8A10 combinatorial library

| Position relative to SEQ ID NO: 10 | 26 | 27 | 28 | 29 | 30 | 31 | 32 | 33 | 34 | 35 | Seq ID NO: | 50 | 51 | 52 | 53 | 54 | 55 | 56 | 57 | 58 | 59 | 60 | 61 | 62 | 63 | 64 | 65 | 66 | Seq ID NO: |
|---|---|---|---|---|---|---|---|---|---|---|---|---|---|---|---|---|---|---|---|---|---|---|---|---|---|---|---|---|---|
| Fab | | | | H1 | | | | | | | | | | | | | | CDR | | | | H2 | | | | | | | |
| Wild Type | G | Y | T | F | T | D | S | T | M | N | 58 | E | I | D | P | N | N | G | G | T | N | Y | N | Q | K | F | K | G | 69 |
| CP2 | G | Y | R | F | T | D | S | T | M | N | 118 | E | I | W | P | N | N | G | G | T | N | Y | N | Q | K | F | K | G | 125 |
| CP3 | G | Y | R | F | T | D | S | T | M | N | 119 | E | I | H | P | N | N | G | G | T | N | Y | N | Q | K | F | K | G | 126 |
| CP4 | G | Y | R | F | T | D | S | T | M | N | 120 | E | I | F | P | N | N | G | G | T | N | Y | N | Q | K | F | K | G | 127 |
| CP5 | G | Y | T | F | T | D | S | T | M | N | 58 | E | I | D | P | N | N | G | G | T | N | Y | N | Q | K | F | K | G | 128 |
| CP6 | G | Y | R | F | T | D | S | T | M | N | 121 | E | I | F | P | N | N | G | G | T | N | Y | N | Q | K | F | K | G | 129 |
| CP7 | G | Y | R | F | T | D | S | T | M | N | 122 | E | I | W | P | N | N | G | G | T | N | Y | N | Q | K | F | K | G | 130 |
| CP8 | G | Y | R | F | T | D | S | T | M | N | 123 | E | I | W | P | N | N | G | G | T | N | Y | N | Q | K | F | K | G | 131 |
| CP9 | G | Y | F | F | T | D | S | T | M | N | 124 | E | I | F | P | N | N | G | G | T | N | Y | N | Q | K | F | K | G | 132 |

Alignments of the variable regions for the whole light and heavy chain regions for the reference 8A10 Fab and the select combinatorial positive clones are illustrated in FIG. 8, with positions exhibiting divergent sequence are indicated.

C. Verification of Final Combinatorial "Hits" Using the Antigen-specific ELISA

Figure 7:
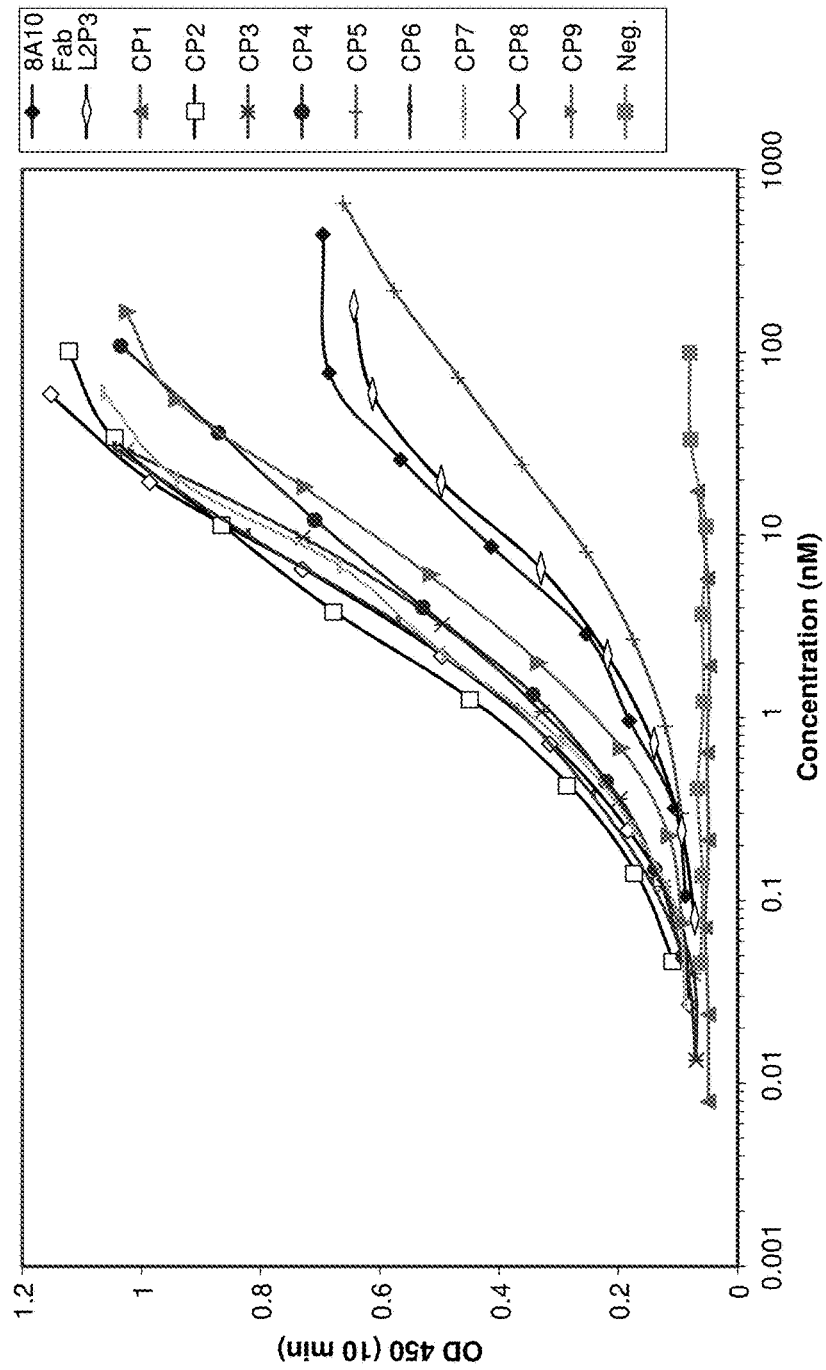
FIG. 7 graphically illustrates an ELISA assay demonstrating the binding of select 8A10 derived Fab variants obtained from the combinatorial library to BSA-paclitaxel.

Clones that were chosen as final "hits" were isolated and tested for direct binding and competitive inhibition with paclitaxel antigen, as described above. A phage-infected culture of *E. coli* of each selected "hit" was harvested and the periplasmic contents were released by osmotic shock (periprep). Fab concentrations were quantified by Quant ELISA and antigen-specific binding of the Fab was performed using the binding ELISA, as described above. The direct binding of select Fabs obtained in the combinatorial library is illustrated in FIG. 7. As illustrated, the majority of the combinatorial Fab variants exhibited increased paclitaxel binding as compared to the reference 8A10 Fab.

CONCLUSION

As described above, affinity reagents containing variant CDR sequences from a reference anti-paclitaxel 8A10 and 3C6 mAb were generated. The selected hits from the 8A10 libraries were further demonstrated to have comparable or enhanced binding affinity for paclitaxel. Furthermore, individual 8A10 mutations that were discovered in the screen were combined to further enhance the binding affinity, thus demonstrating that the numerous combinations of the disclosed sequence variants can be combined in useful reagents to bind, detect, and isolate paclitaxel.

While the preferred embodiment of the invention has been illustrated and described, it will be appreciated that various changes can be made therein without departing from the spirit and scope of the invention.

INDEX OF SEQUENCES

The following is an index of the sequences set forth in the Sequence Listing submitted herewith. The sequences are referred to by their respective SEQ ID NOS as listed in the Sequence Listing 1. Consensus amino acid sequence for 8A10 CDRL1
2. Consensus amino acid sequence for 8A10 CDRL2
3. Consensus amino acid sequence for 8A10 CDRL3
4. Consensus amino acid sequence for 8A10 CDRH1
5. Consensus amino acid sequence for 8A10 CDRH2
6. Consensus amino acid sequence for 8A10 CDRH3
7. Nucleic acid encoding 8A10 VLC region
8. Amino acid sequence of 8A10 VLC region
9. Nucleic acid encoding 8A10 VHC region
10. Amino acid sequence of 8A10 VHC region
11. Amino acid sequence of 8A10 CDRL1
12. Amino acid sequence of 8A10 CDRL1 variant
13. Amino acid sequence of 8A10 CDRL1 variant
14. Amino acid sequence of 8A10 CDRL1 variant
15. Amino acid sequence of 8A10 CDRL1 variant
16. Amino acid sequence of 8A10 CDRL1 variant
17. Amino acid sequence of 8A10 CDRL1 variant
18. Amino acid sequence of 8A10 CDRL1 variant
19. Amino acid sequence of 8A10 CDRL1 variant
20. Amino acid sequence of 8A10 CDRL1 variant
21. Amino acid sequence of 8A10 CDRL1 variant
22. Amino acid sequence of 8A10 CDRL1 variant
23. Amino acid sequence of 8A10 CDRL1 variant
24. Amino acid sequence of 8A10 CDRL1 variant
25. Amino acid sequence of 8A10 CDRL1 variant
26. Amino acid sequence of 8A10 CDRL1 variant
27. Amino acid sequence of 8A10 CDRL1 variant
28. Amino acid sequence of 8A10 CDRL1 variant
29. Amino acid sequence of 8A10 CDRL1 variant
30. Amino acid sequence of 8A10 CDRL1 variant
31. Amino acid sequence of 8A10 CDRL2
32. Amino acid sequence of 8A10 CDRL2 variant
33. Amino acid sequence of 8A10 CDRL2 variant
34. Amino acid sequence of 8A10 CDRL2 variant
35. Amino acid sequence of 8A10 CDRL2 variant
36. Amino acid sequence of 8A10 CDRL2 variant
37. Amino acid sequence of 8A10 CDRL2 variant
38. Amino acid sequence of 8A10 CDRL2 variant
39. Amino acid sequence of 8A10 CDRL2 variant
40. Amino acid sequence of 8A10 CDRL2 variant
41. Amino acid sequence of 8A10 CDRL2 variant
42. Amino acid sequence of 8A10 CDRL2 variant
43. Amino acid sequence of 8A10 CDRL2 variant
44. Amino acid sequence of 8A10 CDRL2 variant
45. Amino acid sequence of 8A10 CDRL3
46. Amino acid sequence of 8A10 CDRL3 variant
47. Amino acid sequence of 8A10 CDRL3 variant
48. Amino acid sequence of 8A10 CDRL3 variant
49. Amino acid sequence of 8A10 CDRL3 variant
50. Amino acid sequence of 8A10 CDRL3 variant
51. Amino acid sequence of 8A10 CDRL3 variant
52. Amino acid sequence of 8A10 CDRL3 variant
53. Amino acid sequence of 8A10 CDRL3 variant
54. Amino acid sequence of 8A10 CDRL3 variant
55. Amino acid sequence of 8A10 CDRL3 variant
56. Amino acid sequence of 8A10 CDRL3 variant
57. Amino acid sequence of 8A10 CDRL3 variant
58. Amino acid sequence of 8A10 CDRH1
59. Amino acid sequence of 8A10 CDRH1 variant
60. Amino acid sequence of 8A10 CDRH1 variant
61. Amino acid sequence of 8A10 CDRH1 variant
62. Amino acid sequence of 8A10 CDRH1 variant
63. Amino acid sequence of 8A10 CDRH1 variant
64. Amino acid sequence of 8A10 CDRH1 variant
65. Amino acid sequence of 8A10 CDRH1 variant
66. Amino acid sequence of 8A10 CDRH1 variant
67. Amino acid sequence of 8A10 CDRH1 variant
68. Amino acid sequence of 8A10 CDRH2
69. Amino acid sequence of 8A10 CDRH2 segment A
70. Amino acid sequence of 8A10 CDRH2 segment A variant
71. Amino acid sequence of 8A10 CDRH2 segment A variant
72. Amino acid sequence of 8A10 CDRH2 segment A variant
73. Amino acid sequence of 8A10 CDRH2 segment A variant
74. Amino acid sequence of 8A10 CDRH2 segment A variant
75. Amino acid sequence of 8A10 CDRH2 segment A variant
76. Amino acid sequence of 8A10 CDRH2 segment A variant
77. Amino acid sequence of 8A10 CDRH2 segment A variant
78. Amino acid sequence of 8A10 CDRH2 segment A variant
79. Amino acid sequence of 8A10 CDRH2 segment A variant
80. Amino acid sequence of 8A10 CDRH2 segment A variant 81. Amino acid sequence of 8A10 CDRH2 segment A variant
82. Amino acid sequence of 8A10 CDRH2 segment A variant
83. Amino acid sequence of 8A10 CDRH2 segment A variant
84. Amino acid sequence of 8A10 CDRH2 segment A variant
85. Amino acid sequence of 8A10 CDRH2 segment A variant
86. Amino acid sequence of 8A10 CDRH2 segment A variant
87. Amino acid sequence of 8A10 CDRH2 segment A variant
88. Amino acid sequence of 8A10 CDRH2 segment A variant
89. Amino acid sequence of 8A10 CDRH2 segment A variant
90. Amino acid sequence of 8A10 CDRH2 segment A variant
91. Amino acid sequence of 8A10 CDRH2 segment B
92. Amino acid sequence of 8A10 CDRH2 segment B variant
93. Amino acid sequence of 8A10 CDRH2 segment B variant
94. Amino acid sequence of 8A10 CDRH2 segment B variant
95. Amino acid sequence of 8A10 CDRH2 segment B variant
96. Amino acid sequence of 8A10 CDRH2 segment B variant
97. Amino acid sequence of 8A10 CDRH2 segment B variant
98. Amino acid sequence of 8A10 CDRH2 segment B variant
99. Amino acid sequence of 8A10 CDRH3
100. Amino acid sequence of 8A10 CDRH3 variant
101. Amino acid sequence of 8A10 CDRH3 variant
102. Amino acid sequence of 8A10 CDRH3 variant
103. Amino acid sequence of 8A10 CDRH3 variant
104. Amino acid sequence of CDRL1 of 8A10 combinatorial variant CP2
105. Amino acid sequence of CDRL1 of 8A10 combinatorial variant CP3
106. Amino acid sequence of CDRL1 of 8A10 combinatorial variant CP4
107. Amino acid sequence of CDRL1 of 8A10 combinatorial variant CP6
108. Amino acid sequence of CDRL1 of 8A10 combinatorial variant CP7
109. Amino acid sequence of CDRL1 of 8A10 combinatorial variant CP8
110. Amino acid sequence of CDRL1 8A10 of combinatorial variant CP9
111. Amino acid sequence of CDRL2 of 8A10 combinatorial variant CP2
112. Amino acid sequence of CDRL2 8A10 of combinatorial variant CP3
113. Amino acid sequence of CDRL2 of 8A10 combinatorial variant CP4
114. Amino acid sequence of CDRL2 of 8A10 combinatorial variant CP6
115. Amino acid sequence of CDRL2 of 8A10 combinatorial variant CP7
116. Amino acid sequence of CDRL2 of 8A10 combinatorial variant CP8
117. Amino acid sequence of CDRL2 of 8A10 combinatorial variant CP9
118. Amino acid sequence of CDRH1 of 8A10 combinatorial variant CP2
119. Amino acid sequence of CDRH1 of 8A10 combinatorial variant CP3
120. Amino acid sequence of CDRH1 of 8A10 combinatorial variant CP4
121. Amino acid sequence of CDRH1 of 8A10 combinatorial variant CP6
122. Amino acid sequence of CDRH1 of 8A10 combinatorial variant CP7
123. Amino acid sequence of CDRH1 of 8A10 combinatorial variant CP8
124. Amino acid sequence of CDRH1 of 8A10 combinatorial variant CP9
125. Amino acid sequence of CDRH2 of 8A10 combinatorial variant CP2
126. Amino acid sequence of CDRH2 of 8A10 combinatorial variant CP3
127. Amino acid sequence of CDRH2 of 8A10 combinatorial variant CP4
128. Amino acid sequence of CDRH2 of 8A10 combinatorial variant CP5
129. Amino acid sequence of CDRH2 of 8A10 combinatorial variant CP6
130. Amino acid sequence of CDRH2 of 8A10 combinatorial variant CP7
131. Amino acid sequence of CDRH2 of 8A10 combinatorial variant CP8
132. Amino acid sequence of CDRH2 of 8A10 combinatorial variant CP9
133. Consensus amino acid sequence for 3C6 CDRL1
134. Consensus amino acid sequence for 3C6 CDRL2
135. Consensus amino acid sequence for 3C6 CDRL3
136. Consensus amino acid sequence for 3C6 CDRH1
137. Consensus amino acid sequence for 3C6 CDRH2
138. Consensus amino acid sequence for 3C6 CDRH3
139. Nucleic acid encoding 3C6 VLC region
140. Amino acid sequence of 3C6 VLC region
141. Nucleic acid encoding 3C6 VHC region
142. Amino acid sequence of 3C6 VHC region
143. Amino acid sequence of 3C6 CDRL1
144. Amino acid sequence of 3C6 CDRL1 segment A
145. Amino acid sequence of 3C6 CDRL1 segment A variant
146. Amino acid sequence of 3C6 CDRL1 segment A variant
147. Amino acid sequence of 3C6 CDRL1 segment A variant
148. Amino acid sequence of 3C6 CDRL1 segment A variant
149. Amino acid sequence of 3C6 CDRL1 segment A variant
150. Amino acid sequence of 3C6 CDRL1 segment B
151. Amino acid sequence of 3C6 CDRL1 segment B variant
152. Amino acid sequence of 3C6 CDRL1 segment B variant
153. Amino acid sequence of 3C6 CDRL1 segment B variant
154. Amino acid sequence of 3C6 CDRL1 segment B variant
155. Amino acid sequence of 3C6 CDRL2
156. Amino acid sequence of 3C6 CDRL2 variant
157. Amino acid sequence of 3C6 CDRL2 variant
158. Amino acid sequence of 3C6 CDRL2 variant
159. Amino acid sequence of 3C6 CDRL2 variant
160. Amino acid sequence of 3C6 CDRL3
161. Amino acid sequence of 3C6 CDRL3 variant
162. Amino acid sequence of 3C6 CDRL3 variant
163. Amino acid sequence of 3C6 CDRL3 variant 164. Amino acid sequence of 3C6 CDRL3 variant
165. Amino acid sequence of 3C6 CDRL3 variant
166. Amino acid sequence of 3C6 CDRH1
167. Amino acid sequence of 3C6 CDRH1 variant
168. Amino acid sequence of 3C6 CDRH1 variant
169. Amino acid sequence of 3C6 CDRH1 variant
170. Amino acid sequence of 3C6 CDRH1 variant
171. Amino acid sequence of 3C6 CDRH1 variant
172. Amino acid sequence of 3C6 CDRH2
173. Amino acid sequence of 3C6 CDRH2 segment A
174. Amino acid sequence of 3C6 CDRH2 segment A variant
175. Amino acid sequence of 3C6 CDRH2 segment A variant
176. Amino acid sequence of 3C6 CDRH2 segment A variant
177. Amino acid sequence of 3C6 CDRH2 segment A variant
178. Amino acid sequence of 3C6 CDRH2 segment A variant
179. Amino acid sequence of 3C6 CDRH2 segment B
180. Amino acid sequence of 3C6 CDRH2 segment B variant
181. Amino acid sequence of 3C6 CDRH2 segment B variant
182. Amino acid sequence of 3C6 CDRH2 segment B variant
183. Amino acid sequence of 3C6 CDRH2 segment B variant
184. Amino acid sequence of 3C6 CDRH3
185. Amino acid sequence of 3C6 CDRH3 variant
186. Amino acid sequence of 3C6 CDRH3 variant
187. Amino acid sequence of 3C6 CDRH3 variant
188. Amino acid sequence of 3C6 CDRH3 variant
189. Amino acid sequence of 3C6 CDRH3 variant
190. Amino acid sequence of 8A10 VLC region variant
191. Amino acid sequence of 8A10 VLC region variant
192. Amino acid sequence of 8A10 VLC region variant
193. Amino acid sequence of 8A10 VLC region variant
194. Amino acid sequence of 8A10 VLC region variant
195. Amino acid sequence of 8A10 VLC region variant
196. Amino acid sequence of 8A10 VLC region variant
197. Amino acid sequence of 8A10 VLC region variant
198. Amino acid sequence of 8A10 VHC region variant
199. Amino acid sequence of 8A10 VHC region variant
200. Amino acid sequence of 8A10 VHC region variant
201. Amino acid sequence of 8A10 VHC region variant
202. Amino acid sequence of 8A10 VHC region variant
203. Amino acid sequence of 8A10 VHC region variant
204. Amino acid sequence of 8A10 VHC region variant
205. Amino acid sequence of 8A10 VHC region variant
206. Amino acid sequence of 3C6 VLC region variant
207. Amino acid sequence of 3C6 VLC region variant
208. Amino acid sequence of 3C6 VLC region variant
209. Amino acid sequence of 3C6 VLC region variant
210. Amino acid sequence of 3C6 VLC region variant
211. Amino acid sequence of 3C6 VLC region variant
212. Amino acid sequence of 3C6 VLC region variant
213. Amino acid sequence of 3C6 VLC region variant
214. Amino acid sequence of 3C6 VLC region variant
215. Amino acid sequence of 3C6 VLC region variant
216. Amino acid sequence of 3C6 VLC region variant
217. Amino acid sequence of 3C6 VLC region variant
218. Amino acid sequence of 3C6 VLC region variant
219. Amino acid sequence of 3C6 VLC region variant
220. Amino acid sequence of 3C6 VLC region variant
221. Amino acid sequence of 3C6 VLC region variant
222. Amino acid sequence of 3C6 VLC region variant
223. Amino acid sequence of 3C6 VLC region variant
224. Amino acid sequence of 3C6 VLC region variant
225. Amino acid sequence of 3C6 VLC region variant
226. Amino acid sequence of 3C6 VHC region variant
227. Amino acid sequence of 3C6 VHC region variant
228. Amino acid sequence of 3C6 VHC region variant
229. Amino acid sequence of 3C6 VHC region variant
230. Amino acid sequence of 3C6 VHC region variant
231. Amino acid sequence of 3C6 VHC region variant
232. Amino acid sequence of 3C6 VHC region variant
233. Amino acid sequence of 3C6 VHC region variant
234. Amino acid sequence of 3C6 VHC region variant
235. Amino acid sequence of 3C6 VHC region variant
236. Amino acid sequence of 3C6 VHC region variant
237. Amino acid sequence of 3C6 VHC region variant
238. Amino acid sequence of 3C6 VHC region variant
239. Amino acid sequence of 3C6 VHC region variant
240. Amino acid sequence of 3C6 VHC region variant
241. Amino acid sequence of 3C6 VHC region variant
242. Amino acid sequence of 3C6 VHC region variant
243. Amino acid sequence of 3C6 VHC region variant
244. Amino acid sequence of 3C6 VHC region variant
245. Amino acid sequence of 3C6 VHC region variant
246. Amino acid sequence of 3C6 CDRL1 segment A variant
247. Amino acid sequence of 3C6 CDRH3 variant
248. Amino acid sequence of 3C6 CDRH3 variant

The invention claimed is:

1. A monoclonal antibody or antibody fragment, comprising one of the following combinations of complementary determining region sequences:

(1) a light chain complementary determining region CDR1 with the amino acid sequence set forth in SEQ ID NO: 104,
a light chain complementary determining region CDR2 with the amino acid sequence set forth in SEQ ID NO:111,
a light chain complementary determining region CDR3 with the amino acid sequence set forth in SEQ ID NO:3,
a heavy chain complementary determining region CDR1 with the amino acid sequence set forth in SEQ ID NO: 118,
a heavy chain complementary determining region CDR2 with the amino acid sequence set forth in SEQ ID NO: 125, and
a heavy chain complementary determining region CDR3 with the amino acid sequence set forth in SEQ ID NO:6;

(2) a light chain complementary determining region CDR1 with the amino acid sequence set forth in SEQ ID NO: 105,
a light chain complementary determining region CDR2 with the amino acid sequence set forth in SEQ ID NO: 112,
a light chain complementary determining region CDR3 with the amino acid sequence set forth in SEQ ID NO:3,
a heavy chain complementary determining region CDR1 with the amino acid sequence set forth in SEQ ID NO: 119,
a heavy chain complementary determining region CDR2 with the amino acid sequence set forth in SEQ ID NO: 126, and
a heavy chain complementary determining region CDR3 with the amino acid sequence set forth in SEQ ID NO:6;

(3) a light chain complementary determining region CDR1 with the amino acid sequence set forth in SEQ ID NO: 106,
a light chain complementary determining region CDR2 with the amino acid sequence set forth in SEQ ID NO: 113,
a light chain complementary determining region CDR3 with the amino acid sequence set forth in SEQ ID NO:3,
a heavy chain complementary determining region CDR1 with the amino acid sequence set forth in SEQ ID NO: 120,
a heavy chain complementary determining region CDR2 with the amino acid sequence set forth in SEQ ID NO: 127, and
a heavy chain complementary determining region CDR3 with the amino acid sequence set forth in SEQ ID NO:6;

(4) a light chain complementary determining region CDR1 with the amino acid sequence set forth in SEQ ID NO: 107,
a light chain complementary determining region CDR2 with the amino acid sequence set forth in SEQ ID NO: 114,
a light chain complementary determining region CDR3 with the amino acid sequence set forth in SEQ ID NO:3,
a heavy chain complementary determining region CDR1 with the amino acid sequence set forth in SEQ ID NO: 121,
a heavy chain complementary determining region CDR2 with the amino acid sequence set forth in SEQ ID NO: 129, and
a heavy chain complementary determining region CDR3 with the amino acid sequence set forth in SEQ ID NO:6;

(5) a light chain complementary determining region CDR1 with the amino acid sequence set forth in SEQ ID NO: 108,
a light chain complementary determining region CDR2 with the amino acid sequence set forth in SEQ ID NO: 115, a light chain complementary determining region CDR3 with the amino acid sequence set forth in SEQ ID NO:3,
a heavy chain complementary determining region CDR1 with the amino acid sequence set forth in SEQ ID NO: 122,
a heavy chain complementary determining region CDR2 with the amino acid sequence set forth in SEQ ID NO: 130, and
a heavy chain complementary determining region CDR3 with the amino acid sequence set forth in SEQ ID NO:6;
(6) a light chain complementary determining region CDR1 with the amino acid sequence set forth in SEQ ID NO: 109,
a light chain complementary determining region CDR2 with the amino acid sequence set forth in SEQ ID NO: 116,
a light chain complementary determining region CDR3 with the amino acid sequence set forth in SEQ ID NO:3,
a heavy chain complementary determining region CDR1 with the amino acid sequence set forth in SEQ ID NO: 123,
a heavy chain complementary determining region CDR2 with the amino acid sequence set forth in SEQ ID NO: 131, and
a heavy chain complementary determining region CDR3 with the amino acid sequence set forth in SEQ ID NO:6; and
(7) a light chain complementary determining region CDR1 with the amino acid sequence set forth in SEQ ID NO: 110,
a light chain complementary determining region CDR2 with the amino acid sequence set forth in SEQ ID NO: 117,
a light chain complementary determining region CDR3 with the amino acid sequence set forth in SEQ ID NO:3,
a heavy chain complementary determining region CDR1 with the amino acid sequence set forth in SEQ ID NO: 124,
a heavy chain complementary determining region CDR2 with the amino acid sequence set forth in SEQ ID NO: 132, and
a heavy chain complementary determining region CDR3 with the amino acid sequence set forth in SEQ ID NO:6;
wherein the monoclonal antibody or antibody fragment binds to paclitaxel.

2. The monoclonal antibody or antibody fragment of claim 1, wherein the antibody or antibody fragment comprises an A9R substitution with respect to SEQ ID NO:11, and further comprises one or more of the following amino acid substitutions: N5R and N5K with respect to SEQ ID NO:11, A2T, S31I, S3N and N4R, with respect to SEQ ID NO:31, T3R, with respect to SEQ ID NO:58, and D3F and D3W, with respect to SEQ ID NO:68.

3. The monoclonal antibody or antibody fragment of claim 1 wherein light chain CDR1 comprises an amino acid sequence selected from SEQ ID NOS:104, 105, 108 and 109.

4. The monoclonal antibody or antibody fragment of claim 1, wherein the light chain CDR2 comprises an amino acid sequence selected from SEQ ID NOS:111-116.

5. The monoclonal antibody or antibody fragment of claim 1, wherein the heavy chain CDR1 CDR2 comprises an amino acid sequence of SEQ ID NO:125.

6. The monoclonal antibody or antibody fragment of claim 1 wherein the heavy chain CDR2 comprises an amino acid sequence of SEQ ID NO:126.

7. The monoclonal antibody or antibody fragment of claim 1 wherein the antibody or antibody fragment comprises at least one amino acid difference in a non-CDR amino acid sequence from a corresponding non-CDR amino acid sequence of the 8A10 antibody.

8. A method of detecting paclitaxel in a sample, comprising:
contacting the sample with an antibody or antibody fragment, as described in claim 1, in an immunoassay,
detecting the formation of a complex between the monoclonal antibody or antibody fragment and paclitaxel,
wherein the formation of a complex is indicative of the presence of paclitaxel in the sample.

9. The method of claim 8, wherein the immunoassay is a lateral flow format.

10. The method of claim 8, wherein the sample is a biological sample.

11. The method of claim 10, wherein the biological sample is from a subject that previously received an administration of paclitaxel or paclitaxel-based therapeutic.

12. The method of claim 11, wherein the subject is a human.

13. The method of claim 8, further comprising quantifying the amount of paclitaxel in the sample, wherein the quantification step comprises determining a level of complex formation between the monoclonal antibody or antibody fragment and paclitaxel, and comparing the level to a level of complex formation obtained from one or more samples with known concentration or concentrations of paclitaxel.

* * * * *

UNITED STATES PATENT AND TRADEMARK OFFICE
CERTIFICATE OF CORRECTION

PATENT NO. : 9,964,551 B2  
APPLICATION NO. : 15/289016  
DATED : May 8, 2018  
INVENTOR(S) : Trieu et al.

Page 1 of 1

It is certified that error appears in the above-identified patent and that said Letters Patent is hereby corrected as shown below:

| Column | Line | Error |
|---|---|---|
| 172 (Claim 2, Line 6) | 4 | "A2T, S31I," should read --A2T, S31,-- |
| 172 (Claim 5, Line 2) | 16 | "heavy chain CDR1 CDR2" should read --heavy chain CDR2-- |

Signed and Sealed this  
Second Day of October, 2018

Andrei Iancu  
*Director of the United States Patent and Trademark Office*